US00RE50288E

(19) United States
(12) Reissued Patent
Simioni

(10) Patent Number: US RE50,288 E
(45) Date of Reissued Patent: Feb. 4, 2025

(54) FACTOR IX POLYPEPTIDE MUTANT, ITS USES AND A METHOD FOR ITS PRODUCTION

(71) Applicant: UNIQURE BIOPHARMA B.V., Amsterdam (NL)

(72) Inventor: Paolo Simioni, Padua (IT)

(73) Assignee: UNIQURE BIOPHARMA B.V., Amsterdam (NL)

(21) Appl. No.: 18/153,894

(22) Filed: Jan. 12, 2023

Related U.S. Patent Documents

Reissue of:
(64) Patent No.: 9,249,405
Issued: Feb. 2, 2016
Appl. No.: 13/063,898
PCT Filed: Sep. 15, 2009
PCT No.: PCT/EP2009/061935
§ 371 (c)(1),
(2) Date: May 31, 2011
PCT Pub. No.: WO2010/029178
PCT Pub. Date: Mar. 18, 2010

(30) Foreign Application Priority Data

Sep. 15, 2008 (IT) ..... BO2008A000564
May 6, 2009 (IT) ..... BO2009A000275

(51) Int. Cl.
*A61P 7/04* (2006.01)
*A61K 38/48* (2006.01)
*C12N 9/64* (2006.01)

(52) U.S. Cl.
CPC ..... *C12N 9/644* (2013.01); *A61K 38/4846* (2013.01); *A61P 7/04* (2018.01); *C12Y 304/21022* (2013.01)

(58) Field of Classification Search
CPC .... C12N 9/644; A61K 38/00; A61K 38/4846; C12Y 304/21022; A61P 7/04
See application file for complete search history.

(56) References Cited

U.S. PATENT DOCUMENTS

| | | | | |
|---|---|---|---|---|
| 4,994,371 | A | 2/1991 | Davie et al. | |
| 5,171,569 | A | 12/1992 | Anson et al. | |
| 5,223,408 | A | 6/1993 | Goeddel et al. | |
| 6,046,380 | A | 4/2000 | Clark | |
| 6,227,618 | B1 | 5/2001 | Ligon, Sr. et al. | |
| 6,277,618 | B1 | 8/2001 | Kopetzki et al. | |
| 6,315,995 | B1 | 11/2001 | Pinsky et al. | |
| 6,531,298 | B2 | 3/2003 | Stafford et al. | |
| 6,610,906 | B1 | 8/2003 | Kurachi et al. | |
| 6,759,050 | B1 | 7/2004 | Sista et al. | |
| 7,125,841 | B2 | 10/2006 | Sheehan | |
| 7,341,871 | B2 | 3/2008 | Kurachi et al. | |
| 7,700,734 | B2 | 4/2010 | Lin et al. | |
| 7,888,067 | B2 | 2/2011 | Lin et al. | |
| 8,383,388 | B2 | 2/2013 | Oyhenart et al. | |
| 8,778,870 | B2 | 7/2014 | Madison et al. | |
| 9,249,405 | B2 * | 2/2016 | Simioni | A61K 38/4846 |
| 9,982,248 | B2 * | 5/2018 | Simioni | C12N 9/644 |
| 10,465,180 | B2 | 11/2019 | Simioni | |
| 10,888,628 | B2 | 1/2021 | Wang et al. | |
| 11,452,749 | B2 | 9/2022 | Nijmeijer et al. | |
| 2002/0031799 | A1 | 3/2002 | Stafford et al. | |
| 2002/0166130 | A1 | 11/2002 | Velander et al. | |
| 2004/0102388 | A1 | 5/2004 | High et al. | |
| 2004/0110675 | A1 | 6/2004 | Sheehan | |
| 2004/0110688 | A1 | 6/2004 | Bajaj et al. | |
| 2004/0133930 | A1 | 7/2004 | Cooper et al. | |
| 2004/0146938 | A1 | 7/2004 | Nguyen et al. | |
| 2004/0254106 | A1 | 12/2004 | Carr et al. | |
| 2005/0100982 | A1 | 5/2005 | DeFrees et al. | |
| 2005/0276787 | A1 | 12/2005 | Couto et al. | |
| 2006/0031956 | A1 | 2/2006 | Kurachi et al. | |
| 2006/0040856 | A1 | 2/2006 | DeFrees et al. | |
| 2006/0188482 | A1 | 8/2006 | Kay et al. | |
| 2006/0292117 | A1 | 12/2006 | Loiler et al. | |
| 2007/0093443 | A1 | 4/2007 | Madison et al. | |
| 2007/0172846 | A1 | 7/2007 | Zhang et al. | |
| 2007/0243526 | A1 | 10/2007 | Kay et al. | |
| 2007/0243615 | A1 | 10/2007 | Qu et al. | |
| 2007/0244036 | A1 | 10/2007 | Scheiflinger et al. | |
| 2007/0274908 | A1 | 11/2007 | Pasqualini et al. | |
| 2007/0280906 | A1 | 12/2007 | Petras | |
| 2008/0003202 | A1 | 1/2008 | Guyon et al. | |
| 2008/0102115 | A1 | 5/2008 | Oyhenart et al. | |

(Continued)

FOREIGN PATENT DOCUMENTS

| | | |
|---|---|---|
| BR | 0705943 | 12/2008 |
| EP | 0107278 | 5/1984 |

(Continued)

OTHER PUBLICATIONS

Stafford, Thrombosis Journal, 14 (Suppl. 1): 35, pp. 87-91. (Year: 2016).*

Souid, Pediatric Emergency Medicine, Chapter 130—Disorders of Coagulation, pp. 917-926 (Year: 2008).*

GenBank Accession No. K02402: Human coagulation Factor IX gene, complete cds, 12 pages (Year: 1996).*

"Abnormal Uterine Bleeding", Wikipedia Article, Oct. 14, 2018, 3 pages.

"Agreement between Avigen, Inc. and Bayer Corporation", Form 10-Q Ex-10.43, Feb. 13, 2001, 83 pages.

(Continued)

*Primary Examiner* — D. L. Jones
(74) *Attorney, Agent, or Firm* — Kilpatrick Townsend & Stockton LLP

(57) ABSTRACT

Disclosed are a modified FIX (factor IX) polypeptide comprising a leucine, cysteine, aspartic acid, glutamic acid, histidine, lysine, asparagine, glutamine or tyrosine in position 338; pharmaceutical preparations containing said modified FIX polypeptide; a nucleotide sequence coding for the modified FIX polypeptide; and a method for producing the modified FIX polypeptide.

7 Claims, 3 Drawing Sheets

Specification includes a Sequence Listing.

(56) References Cited

U.S. PATENT DOCUMENTS

| | | | | |
|---|---|---|---|---|
| 2008/0167219 | A1 | 7/2008 | Lin et al. | |
| 2008/0260820 | A1 | 10/2008 | Borrelly et al. | |
| 2008/0305991 | A1* | 12/2008 | DeFrees et al. | 514/8 |
| 2011/0154516 | A1 | 6/2011 | Stafford et al. | |
| 2012/0164130 | A1 | 6/2012 | Brooks et al. | |
| 2015/0283267 | A1 | 10/2015 | Vandendriessche et al. | |
| 2016/0304851 | A1 | 10/2016 | Schuttrumpf et al. | |
| 2016/0375110 | A1 | 12/2016 | High et al. | |
| 2017/0260516 | A1 | 9/2017 | Tan et al. | |
| 2017/0326256 | A1 | 11/2017 | Doering et al. | |
| 2019/0076550 | A1 | 3/2019 | Wang et al. | |

FOREIGN PATENT DOCUMENTS

| | | | | |
|---|---|---|---|---|
| EP | 2048236 | | 4/2009 | |
| EP | 1781782 | | 5/2010 | |
| EP | 2337849 | | 6/2011 | |
| EP | 2368983 | | 8/2016 | |
| EP | 2767587 | | 4/2017 | |
| WO | 9600577 | | 1/1996 | |
| WO | WO 99/03496 | * | 1/1999 | A61K 38/46 |
| WO | 9949880 | | 10/1999 | |
| WO | 0170763 | | 9/2001 | |
| WO | 0204544 | | 5/2002 | |
| WO | 0240544 | | 5/2002 | |
| WO | 02096454 | | 12/2002 | |
| WO | 03020764 | | 3/2003 | |
| WO | 2006/018204 | | 2/2006 | |
| WO | 2006018201 | | 2/2006 | |
| WO | 2006031226 | | 3/2006 | |
| WO | 2006036502 | | 4/2006 | |
| WO | 2006/048777 | | 5/2006 | |
| WO | 2006066066 | | 6/2006 | |
| WO | 2007059876 | | 5/2007 | |
| WO | 2007075976 | | 7/2007 | |
| WO | 2007089632 | | 8/2007 | |
| WO | 2007135182 | | 11/2007 | |
| WO | 2007/149406 | | 12/2007 | |
| WO | 2007149852 | | 12/2007 | |
| WO | 2008/092643 | | 8/2008 | |
| WO | 2008118507 | | 10/2008 | |
| WO | 2008119815 | | 10/2008 | |
| WO | 2008127654 | | 10/2008 | |
| WO | 2009051717 | | 4/2009 | |
| WO | 2009130198 | | 10/2009 | |
| WO | 2009140015 | | 11/2009 | |
| WO | WO 2009/137254 | * | 11/2009 | A61K 38/36 |
| WO | 2010012451 | | 2/2010 | |
| WO | 2010029178 | | 3/2010 | |
| WO | 2010151736 | | 12/2010 | |
| WO | 2011014890 | | 2/2011 | |
| WO | 2016146757 | | 9/2016 | |
| WO | 2017024060 | | 2/2017 | |
| WO | 2020016318 | | 1/2020 | |

OTHER PUBLICATIONS

"Annex to Examining Division Summons for Divisional Application EP3252157", Dec. 17, 2018, 3 pages.
"Annual Report Pursuant to Section 13 or 15(D) of the Securities Exchange Act of 1934", United States Securities and Exchange Commission, Form 20-F, Accessed from Internet on Feb. 23, 2022, 255 pages.
"Avigen Dropping AAV Gene Therapy", LexisNexis, Feb. 22, 2022, 2 pages.
"BeneFIX Coagulation Factor IX (Recombinant)", Hoffmann Eitle, Exhibit No. D16, Mar. 12, 2019, 16 pages.
"Cardiovascular Disease", Wikipedia Article, Feb. 17, 2019, 25 pages.
"Current Report Pursuant to Section 13 or 15(D) of the Securities and Exchange Act of 1934", Avigen, Inc., United States Securities and Exchange Commission, Accessed from Internet on Feb. 23, 2022, 6 pages.
"Deposition of Dr. Lili Wang", Errata Sheet, Sep. 15, 2020, pp. 251-252.
"Deposition of Dr. Lili Wang, Ph.D.", Errata Sheet, Feb. 9, 2021, 5 pages.
"Fields Virology", Knipe & Howley Eds., 5th Edition, 2007, 33 pages.
"Freeline Presents Long-Term Follow-Up Data from Phase 1/2 B-Amaze Trial in Hemophilia B at the 2021 ASH Annual Meeting and Announces Early Initiation of Phase 1/2 B-Lieve Dose-Confrmation Trial", Globe Newswire, Dec. 13, 2021, 9 pages.
"Guidance for Human Somatic Cell Therapy and Gene Therapy", U.S. Department of Health and Human Services Food and Drug Administration, Center for Biologics Evaluation and Research, Mar. 1998, 30 pages.
"Hematologic Disease", Wikipedia Article, Dec. 30, 2018, 4 pages.
"Hemophilia", UniQure, Available online at <http://uniqure.com/gene-therapy/hemophilia.php>, Accessed from Internet on: Jan. 9, 2021, 4 pages.
"Human Coagulation Factor IX Gene, Complete Cds", GenBank Reference Sequence: K02402.1, Apr. 30, 1996, 12 pages.
"Human Gene Therapy for Hemophilia, Guidance for Industry", U.S. Depart of Health and Human Services, Food and Drugs Administration, 2020, 17 pages.
"Hydrophobicity Scales", Rockefeller University, Available Online at: http://web.archive.org/web/20200222103717/http://prowl.rockefell er.edu/aainfo/hydro.htm, Feb. 22, 2020, 2 pages.
"Investigational Medicinal Product Dossier", AAV5-hFIXco-Padua, Version 4.0, (IMPD) (redacted), Oct. 24, 2019, 14 pages.
"Investigator's Brochure (IB)", AAV5-hFIXco and AAV-hFIXco-Padua, Version 1.0, (IB) (redacted), Feb. 13, 2020, 46 pages.
"IPR2020-00388", Coagulation cascade drawing by Dr. Lili Wang, Sep. 15, 2020, 1 page.
"IPR2020-00388", Affidavit of Elizabeth Rosenberg, Gao PDF Version, Aug. 7, 2020, 10 pages.
"IPR2020-00388", Declaration of Lili Wang, Exhibit 1003 of Petition for Inter Partes review of U.S. Pat. No. 9,249,405, Jan. 3, 2020, 105 pages.
"IPR2020-00388", Affidavit of Duncan Hall, submitted as Exhibit 1093, Jan. 11, 2021, 11 pages.
"IPR2020-00388", Affidavit of Elizabeth Rosenberg, Schuettrumpf TOC, Aug. 7, 2020, 12 pages.
"IPR2020-00388", Patent Owners Objections to Petition Evidence, Jul. 27, 2020, 12 pages.
"IPR2020-00388", Affidavit of Rachel J. Watters, Aug. 6, 2020, 13 pages.
"IPR2020-00388", Declaration of Rachel J. Watters, Submitted as Exhibit 1086, Jan. 7, 2021, 14 pages.
"IPR2020-00388", Declaration of Lili Wang, Exhibit 1003 of Petition for Inter Partes review of U.S. Pat. No. 9,249,405, Jan. 13, 2021, 146 pages.
"IPR2020-00388", Revised Declaration of Dr. Christopher Doering, Dec. 2, 2020, 149 pages.
"IPR2020-00388", Declaration of Dr. Christopher Doering, Oct. 13, 2020, 149 pages.
"IPR2020-00388", Affidavit of Elizabeth Rosenberg, Gao TOC, Aug. 7, 2020, 15 pages.
"IPR2020-00388", Declaration of Star Andrews, Aug. 8, 2020, 15 pages.
"IPR2020-00388", Affidavit of Elizabeth Rosenberg, Gao HTML Version, Aug. 7, 2020, 16 pages.
"IPR2020-00388", Preliminary Guidance, Patent Owner's Motion to Amend, Feb. 3, 2021, 16 pages.
"IPR2020-00388", Definition of Individual at Dictionary.com, Apr. 15, 2020, 2 pages.
"IPR2020-00388", Transcript of Telephonic Hearing held, Feb. 23, 2021, 20 pages.
"IPR2020-00388", Transcript of Teleconference, Oct. 1, 2020, 25 pages.
"IPR2020-00388", Affidavit of Elizabeth Rosenberg, Schuettrumpf HTML Version, Aug. 7, 2020, 27 pages.
"IPR2020-00388", Declaration of James L. Mullins, Ph.D., Aug. 10, 2020, 280 pages.

(56) References Cited

OTHER PUBLICATIONS

"IPR2020-00388", Deposition of Lili Wang, Feb. 9, 2021, 293 pages.
"IPR2020-00388", Email from Patent and Trial Appeal Board to Dov Grossman and Justin Krieger, submitted as Exhibit 2069, Mar. 3, 2021, 3 pages.
"IPR2020-00388", Patent Owner's Notice of Withdrawal of Motion to Amend, Mar. 4, 2021, 3 pages.
"IPR2020-00388", Affidavit of Duncan Hall, submitted as Exhibit 1084, Jan. 11, 2021, 32 pages.
"IPR2020-00388", Decision Granting Institution of Inter Partes Review, Jul. 13, 2020, 32 pages.
"IPR2020-00388", Deposition of Lee Pedersen, Sep. 17, 2020, 321 pages.
"IPR2020-00388", Deposition of Lili Wang, Sep. 15, 2020, 330 pages.
"IPR2020-00388", Patent Owner's Revised Non-Contingent Motion to Amend, Dec. 2, 2020, 34 pages.
"IPR2020-00388", Patent Owners Non-Contingent Motion to Amend, Oct. 13, 2020, 34 pages.
"IPR2020-00388", Petitioner's Opoosition to Patent Owner's Revised Non-Contingent Motion to Amend, Jan. 13, 2021, 35 pages.
"IPR2020-00388", Deposition Transcript of Dr. Christopher Doering, Dec. 3, 2020, 355 pages.
"IPR2020-00388", Disclaimer of Claims 6 and 9-13 in U.S. Pat. No. 9,249,405, Apr. 16, 2020, 4 pages.
"IPR2020-00388", Revised Declaration of Elizabeth Heijink redacted, Dec. 7, 2020, 4 pages.
"IPR2020-00388", Patent Owner's Motion to Terminate Proceeding, Mar. 4, 2021, 4 pages.
"IPR2020-00388", Transcript of Telephonic Meeting, Nov. 24, 2020, 43 pages.
"IPR2020-00388", Declaration of James L. Mullins, Ph.D. re: EX1017, EX1083, and EX1082, Jan. 13, 2021, 472 pages.
"IPR2020-00388", Affidavit of Elizabeth Rosenberg, Hasbrouck Online TOC, Aug. 7, 2020, 5 pages.
"IPR2020-00388", Affidavit of Elizabeth Rosenberg, Schuettrumpf PDF, Aug. 7, 2020, 5 pages.
"IPR2020-00388", Email from Justin Krieger to Patent Trial and Appeal Board, Exhibit 1094, Mar. 5, 2021, 5 pages.
"IPR2020-00388", Order Conduct of the Proceeding, Oct. 2, 2020, 5 pages.
"IPR2020-00388", Patent Owner Preliminary Response, Apr. 17, 2020, 51 pages.
"IPR2020-00388", Selected File History of U.S. Pat. No. 10,465,180, as Exhibit 2014, Apr. 17, 2020, 51 pages.
"IPR2020-00388", Deposition Transcript of Dr. Elizabeth Heijink (Dec. 10, 2020) (Redacted), 2020, 6 pages.
"IPR2020-00388", submitted as Exhibit 2070, Disclaimer in Patent under 37 C.F.R. 1.321(a), Mar. 4, 2021, 6 pages.
"IPR2020-00388", Order Conduct of the Proceeding, Nov. 27, 2020, 6 pages.
"IPR2020-00388", Declaration of Elisabeth Heijink, Oct. 13, 2020, 6 pages.
"IPR2020-00388", Patent Examination Policy—MPEP Staff—35 USC 112 1st Para—Enablement of Chemical/Biotechnical Applications, Apr. 17, 2020, 71 pages.
"IPR2020-00388", Declaration of Lee Pedersen, Ph.D., executed Jan. 3, 2020, Exhibit 1002 of Petition for Inter Partes review of U.S. Pat. No. 9,249,405, Jan. 3, 2020, 73 pages.
"IPR2020-00388", Petition for Inter Partes Review of U.S. Pat. No. 9,249,405, Jan. 4, 2020, 75 pages.
"IPR2020-00388", Affidavit of Elizabeth Rosenberg, Advanced Online Publication of Hasbrouck, Aug. 7, 2020, 9 pages.
"IPR2020-00388", Petitioner's Opposition to Patent Owner's Motion to Terminate, Mar. 16, 2021, 9 pages.
"IPR2021-00925", Patent Owner's Response to Petitioner's Notice Regarding Multiple Petitions in IPR2021-00925 and IPR2021-00926, Aug. 21, 2021, 8 pages.
"IPR2021-00925", Patent Owner Preliminary Response, Aug. 21, 2021, 80 pages.
"IPR2021-00925", Patent Owner Preliminary Response, Aug. 23, 2021, 80 pages.
"IPR2021-00926", Patent Owner's Response to Petitioner's Notice Regarding Multiple Petitions in IPR2021-00925 and IPR2021-00926, Aug. 21, 2021, 8 pages.
"IPR2021-00926", Patent Owner Preliminary Response, Aug. 21, 2021, 80 pages.
"IPR2021-00926", Patent Owner Preliminary Response, Aug. 23, 2021, 80 pages.
"IPR2021-00928", Email from Patent and Trial Appeal Board to Dov Grossman, (Exhibit 2087), Jul. 21, 2021, 2 pages.
"IPR2021-00928", Third Party Submission, File History of U.S. Pat. No. 10,465,180, (Exhibit 2080), Mar. 14, 2019, 25 pages.
"IPR2021-00928", Information Disclosure Statement, File History for U.S. Pat. No. 9,249,405, (Exhibit 2010), Mar. 31, 2014, 3 pages.
"IPR2021-00928", Patent Owner Preliminary Response, Aug. 24, 2021, 83 pages.
"Long-Acting Factor VIIa had Longer Duration of Action in Hemophilic A Mice", ISTH 2009 Daily, XXII Congress International Society on Thrombosis and Haemostasis, 2009, 12 pages.
"National Case Law on Peer Reviewed Documents", Jan. 23, 2019, 2 pages.
"*Pacific Coast Building Products, Inc.* v. *Certain Teed Gypsum, Inc.*", 816 Fed. Appx. 454, 459 (Fed. Cir. 2020) (unpublished), 2020, 6 pages.
"Pfizer Initiates Pivotal Phase 3 Program for Investigational Hemophilia B Gene Therapy", Spark Therapeutics Press Release, Available online at https://sparktx.com/press_releases/pfizer-initiates-pivotal-phase-3-program-for-investigational-hemophilia-b-gene-therapy/, Jul. 16, 2018, pp. 1-6.
"Press Release: Spark Therapeutics to Present with Pfizer Inc. Preclinical Data on Their Lead SPK-FIX Product Candidate for Hemophilia B at the 2015 International Society of Thrombosis and Haemostasis Congress in June", LexisNexis, Jun. 18, 2015, 5 pages.
"STN—The Choice of Patent Experts", CAS Registry Fact Sheet, 2014, 1 page.
"Supplementary Table 1. Inclusion/exclusion Criteria", Supplementary Data, uniQure 2128, 2006, 1 page.
"Textbook of Hemophilia", Third Edition, 2014, 25 pages.
"The Value of Treatment Advances in Hemophilia", Pfizer, Value of Medicine, Available Online at: https://cdn.pfizer.com/pfizercom/health/VoM, Dec. 2016, 5 pages.
"UniQure Announces Achievement of Target Patient Dosing in HOPE-B Pivotal Trial of AMT-061 (Etranacogene Dezaparvovec) in Hemophilia B", UniQure, Available Online at: https:piplelinereview.com/index.php/2020032774138/DNA-RNA-and-Cells/, Mar. 27, 2020, 2 pages.
"UniQure Announces FDA Removes Clinical Hold on Hemophilia B Gene Therapy Program", UniQure Press Release, Available online at : https://tools.eurolandir.com/tools/Pressreleases/GetPressRelease/?ID=3902770&lang=en-GB&companycode=nl-qure&v=, 2021, pp. 1-3.
"Uniqure Announces First Patient Treated in Pivotal Trial", UniQure, Available Online at: https://drug-dev.com/uniqure-announces-first-patient-treated-in-pivotal-trial/, Oct. 13, 2020, 34 pages.
"What is Gene Therapy?", U.S. Food & Drug Admin, Available Online at: https://www.fda.gov/vaccines-blood-biologics/cellular-gene-therapy-products/what-gene-therapy, Accessed from Internet on Jan. 9, 2021, 2 pages.
Court File No. T-2118-22, Between Pfizer Canada ULC and Pfizer Inc. and Uniqure BioPharma B.V., Written Representations of the Plaintiffs (Defendant's Motion for a Stay), Before the Federal Court, Mar. 23, 2023, 28 pages.
U.S. Appl. No. 13/063,898 , "Final Office Action", Dec. 31, 2014, 21 pages.
U.S. Appl. No. 13/063,898 , "Non-Final Office Action", Apr. 3, 2014, 14 pages.
U.S. Appl. No. 13/063,898 , "Notice of Allowance", Nov. 12, 2015, 4 pages.
U.S. Appl. No. 13/063,898 , "Notice of Allowance", Sep. 28, 2015, 7 pages.

(56) References Cited

OTHER PUBLICATIONS

U.S. Appl. No. 14/981,981 , "Non-Final Office Action", Dec. 7, 2017, 13 pages.
U.S. Appl. No. 15/650,070 , "Non-Final Office Action", Dec. 15, 2017, 15 pages.
U.S. Appl. No. 15/650,070 , "Notice of Allowance", Apr. 10, 2018, 5 pages.
U.S. Appl. No. 15/989,665 , "Non-Final Office Action", Apr. 8, 2019, 7 pages.
U.S. Appl. No. 15/989,665 , "Notice of Allowance", Oct. 7, 2019, 2 pages.
U.S. Appl. No. 15/989,665 , "Notice of Allowance", Jul. 31, 2019, 5 pages.
U.S. Appl. No. 16/589,851 , "Non-Final Office Action", Dec. 20, 2021, 23 pages.
U.S. Appl. No. 16/707,414 , "Non-Final Office Action", Mar. 11, 2021, 16 pages.
U.S. Appl. No. 16/787,456 , "Non-Final Office Action", Jul. 8, 2021, 19 pages.
U.S. Appl. No. 17/213,848 , "Advisory Action", Dec. 21, 2021, 9 pages.
U.S. Appl. No. 17/213,848 , "Final Office Action", Sep. 13, 2021, 18 pages.
U.S. Appl. No. 17/213,848 , "Non-Final Office Action", Jul. 7, 2022, 12 pages.
U.S. Appl. No. 17/213,848 , "Non-Final Office Action", May 28, 2021, 16 pages.
U.S. Appl. No. 17/213,897 , "Advisory Action", Dec. 21, 2021, 6 pages.
U.S. Appl. No. 17/213,897 , "Final Office Action", Sep. 14, 2021, 19 pages.
U.S. Appl. No. 17/213,897 , "Non-Final Office Action", Jun. 1, 2021, 18 pages.
U.S. Appl. No. 17/213,897 , "Non-Final Office Action", Jul. 12, 2022, 23 pages.
U.S. Appl. No. 17/447,372 , "Non-Final Office Action", Jun. 21, 2023, 31 pages.
U.S. Appl. No. 17/643,326 , "Non-Final Office Action", May 15, 2023, 18 pages.
U.S. Appl. No. 60/999,035 , "U.S. Provisional Patent Application No.", Human Factory IX Variants With an Extended Half Life, Oct. 15, 2007, 42 pages.
Ahmad et al., "The Role of the First Growth Factor Domain of Human Factor IXa in Binding to Platelets and in Factor X Activation", The Journal of Biological Chemistry, vol. 267, No. 12, Apr. 25, 1992, pp. 8571-8576.
Altschul et al., "Basic Local Alignment Search Tool", Journal of Molecular Biology, vol. 215, No. 3, Oct. 5, 1990, pp. 403-410.
Altschul et al., "Gapped Blast and PSI-Blast: A New Generation of Protein Database Search Programs", Nucleic Acids Research, vol. 25, No. 17, Sep. 1, 1997, pp. 3389-3402.
Ameri et al., "Myocardial Fibrosis in Mice with Over-Expression of Human Blood Coagulation Factor IX", Blood, vol. 101, No. 5, Apr. 2003, 10 pages.
Anson et al., "The Gene Structure of Human Anti-Haemophilic Factor IX", The EMBO Journal, vol. 3, No. 5, May 1984, pp. 1053-1060.
Armentano et al., "Expression of Human Factor IX in Rabbit Hepatocytes by Retrovirus-Mediated Gene Transfer: Potential for Gene Therapy of Hemophilia B", Proceedings of the National Academy of Sciences of the United States of America, vol. 87, No. 16, Aug. 1990, pp. 6141-6145.
Armstrong , "UniQure Turns the Screw on Spark and Pfizer", Evaluate Vantage, Feb. 2019, 2 pages.
Aucoin et al., "Critical Assessment of Current Adeno-Associated Viral Vector Production and Quantification Methods", Biotechnology Advances, vol. 26, No. 1, Jan.-Feb. 2008, pp. 73-88.
Bajaj et al., "Factor IXa: Factor Villa Interaction. Helix 330-338 of Factor Ixa Interacts with Residues 558-565 and Spatially Adjacent Regions of the a2 Subunit of Factor Villa", The Journal of Biological Chemistry, vol. 276, No. 19, May 11, 2001, pp. 16302-16309.
Bassett et al., "Recent Developments in Hemophilia: Gene Therapy", MedPage Today, Available Online At https://www.medpagetoday.com/recent-developments/hemophilia/78500, Mar. 11, 2019, 5 pages.
Benefix , "Coagulation Factor IX (Recombinant) label", 2006, 2 pages.
Betts et al., "Amino Acid Properties and Consequences of Substitutions", Bioinformatics for Geneticists, Feb. 21, 2003, 28 pages.
Bezemer et al., "F9 Malmo, Factor IX And Deep Vein Thrombosis", Haematologica, vol. 94, No. 5, May 2009, pp. 693-699.
Bond et al., "Biochemical Characterization of Recombinant Factor IX", Seminars in Hematology, vol. 35, No. 2, 1998, pp. 11-17.
Bottema et al., "The Pattern of Spontaneous Germ-Line Mutation: Relative Rates of Mutation at or Near CpG Dinucleotides in the Factor IX Gene", Human Genetics, vol. 91, No. 5, Jun. 1993, pp. 496-503.
Bowen , "Haemophilia A and Haemophilia B: Molecular Insights", Molecular Pathology, vol. 55, No. 2, 2002, pp. 127-144.
Bowie et al., "Deciphering the Message in Protein Sequences: Tolerance to Amino Acid Substitutions", Science, vol. 247, No. 4948, Mar. 16, 1990, pp. 1306-1310.
Branca , "Gene Therapy: Cursed or Inching Towards Credibility?", Nature Biotechnology, vol. 23, No. 5, May 2005, pp. 519-521.
Branden et al., "Introduction to Protein Structure", Garland Publishing, 2012, 73 pages.
Brandstetter et al., "X-Ray Structure of Clotting Factor IXa: Active Site and Module Structure Related to Xase Activity and Hemophilia B", Proceedings of the National Academy of Sciences, vol. 92, No. 21, Oct. 10, 1995, pp. 9796-9800.
Brickhous et al., "Recombinant Human Factor IX: Replacement Therapy, Prophylaxis, and Pharmacokinetics in Canine Hemophilia B", Blood, vol. 88, No. 7, Oct. 1, 1996, pp. 2603-2610.
Brown et al., "Development of a Clinical Candidate AAV3 Vector for Gene Therapy of Hemophilia B", Human Gene Therapy, vol. 31, Nos. 19-20, Oct. 2020, pp. 1114-1123.
Brownlee , "The Molecular Genetics of Haemophilia A and B", Journal of Cell Science, No. 4, 1986, pp. 445-458.
Brunetti-Pierri et al., "Bioengineered Factor IX Molecules with Increased Catalytic Activity Improve the Therapeutic Index of Gene Therapy Vectors for Hemophilia B", Human Gene Therapy, vol. 20, No. 5, May 2009, pp. 479-485.
Bueler , "Adeno-Associated Viral Vectors for Gene Transfer and Gene Therapy", Journal of Biological Chemistry, vol. 380, No. 6, Jun. 1999, pp. 613-622.
Cancio et al., "Developments in the Treatment of Hemophilia B: Focus on Emerging Gene Therapy", The Application of Clinical Genetics, vol. 6, 2013, pp. 91-101.
Cantore et al., "Hyperfunctional Coagulation Factor IX Improves the Efficacy of Gene Therapy in Hemophilic Mice", Blood, vol. 120, No. 23, Nov. 29, 2012, pp. 4517-4520.
Case IPR2021-00925 , "Declaration of Cindy Kan in Support of Exhibits 2025, 2075, 2076, 2088", Before the Patent Trial and Appeal Board, Dec. 16, 2021, 5 pages.
Case IPR2021-00925 , "Declaration of Dr. Christopher Doering Under 37 C.f.r. § 1.68", Before the Patent Trial and Appeal Board, Mar. 3, 2022, 403 pages.
Case IPR2021-00925 , "Declaration of James M. Lyons in Support of Motion for Admission Pro Hac Vice", Before the Patent Trial and Appeal Board, Dec. 20, 2021, 4 pages.
Case IPR2021-00925 , "Declaration of Joshua L. Stern in Support of Motion for Admission Pro Hac Vice", Before the Patent Trial and Appeal Board, Dec. 20, 2021, 4 pages.
Case IPR2021-00925 , "Declaration of P. Clint Spiegel, Ph.D.", Before the Patent Trial and Appeal Board, Mar. 3, 2022, 100 pages.
Case IPR2021-00925 , "Deposition of Lee Grant Pedersen, Ph.D. Conducted Virtually", Planet Depos, Before the Patent Trial and Appeal Board, Feb. 22, 2022, 141 pages.
Case IPR2021-00925 , "Final Written Decision Determining All Challenged Claims Unpatentable 35 U.S.C. § 318(a)", Before the Patent Trial and Appeal Board, Nov. 15, 2022, 50 pages.

(56) References Cited

OTHER PUBLICATIONS

Case IPR2021-00925 , "Notice of Joint Stipulation to Modify the Scheduling Order", Before the Patent Trial and Appeal Board, Dec. 22, 2021, 4 pages.
Case IPR2021-00925 , "Patent Owner's Motion for Admission Pro Hac Vice of James M. Lyons", Before the Patent Trial and Appeal Board, Dec. 20, 2021, 12 pages.
Case IPR2021-00925 , "Patent Owner's Motion for Admission Pro Hac Vice of Joshua L. Stern", Before the Patent Trial and Appeal Board, Dec. 20, 2021, 12 pages.
Case IPR2021-00925 , "Patent Owner's Notice of Deposition of Lee Pedersen, Ph.D.", Before the Patent Trial and Appeal Board, Feb. 2, 2022, 3 pages.
Case IPR2021-00925 , "Patent Owner's Notice of Deposition of Lili Wang, Ph.D.", Before the Patent Trial and Appeal Board, Feb. 2, 2022, 3 pages.
Case IPR2021-00925 , "Patent Owner's Objections to Evidence Pursuant to 37 CFR 42.64", Before the Patent Trial and Appeal Board, Dec. 2, 2021, 14 pages.
Case IPR2021-00925 , "Patent Owner's Second Update to Mandatory Notices Under 37 C.F.R. § 42.8", Before the Patent Trial and Appeal Board, Dec. 20, 2021, 5 pages.
Case IPR2021-00925 , "Petitioner's Motion to Submit Supplemental Information Pursuant to 37 C.f.r § 42.123(A)", Before the Patent Trial and Appeal Board, Jan. 6, 2022, 8 pages.
Case IPR2021-00925 , "Petitioner's Objections to Evidence", Before the Patent Trial and Appeal Board, Mar. 10, 2022, 28 pages.
Case IPR2021-00925 , "Petitioner's Objections to Patent Owner's Preliminary Response Evidence", Before the Patent Trial and Appeal Board, Dec. 2, 2021, 12 pages.
Case IPR2021-00925 , "Transcript of Lili Wang, Ph.D.", Planet Depos, Before the Patent Trial and Appeal Board, Feb. 16, 2022, 191 pages.
Case IPR2021-00925 , "Videotaped Videoconference Deposition of Lee Pedersen, Ph.D.", Before the Patent Trial and Appeal Board, Sep. 17, 2020, 321 pages.
Case IPR2021-00926 , "Final Written Decision Determining All Challenged Claims Unpatentable 35 U.S.C. § 318(a)", Before the Patent Trial and Appeal Board, Nov. 15, 2022, 60 pages.
Case IPR2021-00926 , "Notice of Joint Stipulation to Modify the Scheduling Order", Before the Patent Trial and Appeal Board, Dec. 22, 2021, 4 pages.
Case IPR2021-00926 , "Patent Owner Response", Before the Patent Trial and Appeal Board, Mar. 3, 2022, 89 pages.
Case IPR2021-00926 , "Patent Owner's Motion for Admission Pro Hac Vice of James M. Lyons", Before the Patent Trial and Appeal Board, Dec. 20, 2021, 12 pages.
Case IPR2021-00926 , "Patent Owner's Motion for Admission Pro Hac Vice of Joshua L. Stern", Before the Patent Trial and Appeal Board, Dec. 20, 2021, 13 pages.
Case IPR2021-00926 , "Patent Owner's Notice of Deposition of Lee Pedersen, PH.D.", Before the Patent Trial and Appeal Board, Feb. 2, 2022, 3 pages.
Case IPR2021-00926 , "Patent Owner's Notice of Deposition of Lili Wang, PH.D.", Before the Patent Trial and Appeal Board, Feb. 2, 2022, 3 pages.
Case IPR2021-00926 , "Patent Owner's Objections to Evidence Pursuant to 37 C.F.R. § 42.64", Before the Patent Trial and Appeal Board, Dec. 2, 2021, 13 pages.
Case IPR2021-00926 , "Patent Owner's Second Update to Mandatory Notices Under 37 C.F.R. § 42.8", Before the Patent Trial and Appeal Board, Dec. 20, 2021, 5 pages.
Case IPR2021-00926 , "Petitioner's Motion to Submit Supplemental Information Pursuant to 37 C.F.R § 42.123(a)", Before the Patent Trial and Appeal Board, Jan. 6, 2022, 8 pages.
Case IPR2021-00926 , "Petitioner's Objections to Evidence", Before the Patent Trial and Appeal Board, Mar. 10, 2022, 28 pages.
Case IPR2021-00926 , "Petitioner's Objections to Patent Owner's Preliminary Response Evidence", Before the Patent Trial and Appeal Board, Dec. 2, 2021, 11 pages.
Case IPR2021-00928 , "Final Written Decision Determining All Challenged Claims Unpatentable 35 U.S.C. § 318(a)", Before the Patent Trial and Appeal Board, Nov. 15, 2022, 50 pages.
Case IPR2021-00928 , "Notice of Joint Stipulation to Modify the Scheduling Order", Before the Patent Trial and Appeal Board, Dec. 22, 2021, 4 pages.
Case IPR2021-00928 , "Patent Owner Response", Before the Patent Trial and Appeal Board, Mar. 3, 2022, 85 pages.
Case IPR2021-00928 , "Patent Owner's Motion for Admission Pro Hac Vice of James M. Lyons", Before the Patent Trial and Appeal Board, Dec. 20, 2021, 12 pages.
Case IPR2021-00928 , "Patent Owner's Motion for Admission Pro Hac Vice of Joshua L. Stern", Before the Patent Trial and Appeal Board, Dec. 20, 2021, 13 pages.
Case IPR2021-00928 , "Patent Owner's Notice of Deposition of Lee Pedersen, PH.D.", Before the Patent Trial and Appeal Board, Feb. 2, 2022, 3 pages.
Case IPR2021-00928 , "Patent Owner's Notice of Deposition of Lili Wang, PH.D.", Before the Patent Trial and Appeal Board, Feb. 2, 2022, 3 pages.
Case IPR2021-00928 , "Patent Owner's Objections to Evidence Pursuant to 37 C.F.R. § 42.64", Before the Patent Trial and Appeal Board, Dec. 2, 2021, 13 pages.
Case IPR2021-00928 , "Patent Owner's Second Update to Mandatory Notices Under 37 C.F.R. § 42.8", Before the Patent Trial and Appeal Board, Dec. 20, 2021, 5 pages.
Case IPR2021-00928 , "Petitioner's Motion to Submit Supplemental Information Pursuant to 37 C.F.R § 42.123(a)", Before the Patent Trial and Appeal Board, Jan. 6, 2022, 8 pages.
Case IPR2021-00928 , "Petitioner's Objections to Evidence", Before the Patent Trial and Appeal Board, Mar. 10, 2022, 28 pages.
Case IPR2021-00928 , "Petitioner's Objections to Patent Owner's Preliminary Response Evidence", Before the Patent Trial and Appeal Board, Dec. 2, 2021, 12 pages.
Chamberlain , "Acute Hemorrhagic Gastritis", Gastroenterol Clinics of North America, vol. 22, No. 4, Dec. 1993, pp. 843-873.
Chang et al., "Changing Residue 338 in Human Factor IX from Arginine to Alanine Causes an Increase in Catalytic Activity", The Journal of Biological Chemistry, vol. 273, No. 20, May 15, 1998, pp. 12089-12094.
Chang et al., "Identification of Functionally Important Residues of the Epidermal Growth Factor-2 Domain of Factor IX by Alanine-Scanning Mutagenesis Residues ASN89-GLY93 are Critical for Binding Factor VIIIa", Journal of Biological Chemistry, vol. 277, No. 28, Jul. 12, 2002, pp. 25393-25399.
Chang et al., "Residues 330-338 in Catalytic Domain of Factor IX Represent an Interactive Site for Both Factor VIIIa and Factor X", Blood, Abstract #744, The American Society of Hematology Fortieth Annual Meeting, 1998.
Cheung et al., "The Binding of Human Factor IX to Endothelial Cells Is Mediated by Residues 3-11", The Journal of Biological Chemistry, vol. 267, No. 29, Oct. 15, 1992, pp. 20529-20531.
Choi et al., "Production of Recombinant Adeno-Associated Viral Vectors for In Vitro and In Vivo Use", Current Protocols in Molecular Biology, vol. 16, Issue 25, Apr. 2007, pp. 1-25.
Cooley et al., "Dysfunctional Endogenous Fix Impairs Prophylaxis in a Mouse Hemophilia B Model", Blood, vol. 133, No. 22, May 30, 2019, pp. 2445-2451.
Cooley et al., "Prophylactic Efficacy of BeneFIX vs Alprolix in Hemophilia B Mice", Blood, vol. 128, No. 2, Jul. 14, 2016, pp. 286-292.
Coppens et al., "Adults with Haemophilia B Receiving Etranacogene Dezaparvovec in the Hope-B Phase 3 Trial Experience a Stable Increase in Mean Factor IX Activity and Durable Haemostatic Protection after 24 Months' Follow-up", Presented at the 16th Annual Congress of the European Association for Haemophilia and Allied Disorders (EAHAD), Feb. 7-10, 2023, Feb. 2023, 12 pages.
Couzin et al., "As Gelsinger Case Ends, Gene Therapy Suffers Another Blow", Science, vol. 307, No. 5712, Feb. 18, 2005, 2 pages.
Crick, "The Origin of the Genetic Code", Journal of Molecular Biology , vol. 38, No. 3, Dec. 28, 1968, pp. 367-379.
Crystal , "Adenovirus: The First Effective in Vivo Gene Delivery Vector", Human Gene Therapy, vol. 25, No. 1, Jan. 2014, pp. 3-11.

(56) References Cited

OTHER PUBLICATIONS

Dale et al., "From Genes to Genomes: Concepts and Applications of DNA Technology", John Wiley & Sons, 2011, 94 pages.
Davidoff et al., "Purification of Recombinant Adeno-Associated Virus Type 8 Vectors by Ion Exchange Chromatography Generates Clinical Grade Vector Stock", Journal of Virological Methods, vol. 121, No. 2, Nov. 2004, pp. 209-215.
Davie et al., "The Coagulation Cascade: Initiation, Maintenance, and Regulation", Biochemistry, vol. 30, No. 43, Oct. 1991, pp. 10363-10370.
Daya et al., "Gene Therapy Using Adeno-Associated Virus Vectors", Clinical Microbiology Reviews, vol. 21, No. 4, Oct. 2008, pp. 583-593.
Dayhoff et al., "A Model of Evolutionary Change in Proteins", Atlas of Protein Sequence and Structure, vol. 5, 1978, pp. 345-352.
Devereux et al., "A Comprehensive Set of Sequence Analysis Programs for the VAX", Nucleic Acids Research, vol. 12, No. 1, Jan. 11, 1984, pp. 387-395.
Driscoll et al., "A Codon 338 Nonsense Mutation in the Factor IX Gene in Unrelated Hemophilia B Patients: Factor IX338 New York", Blood, vol. 74, No. 2, Sep. 1989, pp. 737-742.
Enayat et al., "Mutation Analysis in F9 Gene of 17 Families with Haemophilia B from Iran", Haemophilia, vol. 10, No. 6, Nov. 2004, pp. 751-755.
EP09748260.8 , "Decision Revoking the European Patent", Mar. 17, 2021, 2 pages.
EP09748260.8 , "Declaration by Dr Tagariello", Dec. 17, 2018, 1 page.
EP09748260.8 , "EPO Submission by the Patentee", May 10, 2016, 10 pages.
EP09748260.8 , "EPO Submission by the Patentee", May 31, 2017, 11 pages.
EP09748260.8 , "Letter from Patentee", Sep. 21, 2015, 12 pages.
EP09748260.8 , "Notice of Opposition—Baxalta GmbH", Mar. 12, 2019, 56 pages.
EP09748260.8 , "Notice of Opposition—Greaves Brewster LLP", Mar. 13, 2019, 12 pages.
EP09748260.8 , "Notice of Opposition—Pfizer Inc.", Mar. 12, 2019, 25 pages.
EP09748260.8 , "Notice of Opposition—Strawman Limited", Dec. 17, 2018, 30 pages.
EP09748260.8 , "Notice of Opposition—Weinzierl Gerhard Dr.", Mar. 12, 2019, 26 pages.
EP09748260.8 , "Office Action", Dec. 14, 2015, 4 pages.
EP09748260.8 , "Office Action", Jan. 26, 2017, 4 pages.
EP09748260.8 , "Preliminary Opinion", Oct. 17, 2019, 12 pages.
EP09748260.8 , "Sequence Alignment", (D12 Opposition Procedure), Feb. 22, 2018, 1 page.
EP09748260.8 , "Sequence Alignment", (D23 Opposition Procedure), Feb. 22, 2018, 1 page.
EP09748260.8 , "Response to Summons to Attend Oral Proceedings—Weinzierl Gerhard Dr.", Apr. 14, 2020, 13 pages.
EP09748260.8 , "Summons to Attend Oral Proceedings", Oct. 17, 2019, 11 pages.
EP09748260.8 , "Written Submission—Strawman Limited", Mar. 11, 2021, 2 pages.
EP17175191.0 , "Decision to Refuse", Jul. 5, 2019, 14 pages.
EP17175191.0 , "Extended European Search Report", Nov. 8, 2017, 10 pages.
EP17175191.0 , "Office Action", Mar. 2, 2018, 14 pages.
EP17175191.0 , "Office Action", May 25, 2018, 4 pages.
EP17175191.0 , "Office Action", Feb. 12, 2018, 8 pages.
EP17175191.0 , "Summons to Attend Oral Proceedings", Nov. 29, 2018, 6 pages.
EP19174517.3 , "Office Action", Apr. 14, 2021, 4 pages.
EP19174517.3 , "Office Action", Apr. 26, 2022, 5 pages.
EP19174517.3 , "Partial European Search Report", Nov. 25, 2019, 16 pages.
EP19174517.3 , "Notice of Opposition", Sep. 27, 2023, 49 pages.
EP2009074826.0 , "Third Party Observation", Jul. 25, 2017, 3 pages.
EP2009074826.0 , "Third Party Observation", Aug. 14, 2017, 8 pages.
Ertl et al., "Impact of AAV Capsid-specific T-Cell Responses on Design and Outcome of Clinical Gene Transfer Trials With Recombinant Adeno-Associated Viral Vectors: An Evolving Controversy", Human Gene Therapy, vol. 28, No. 4, Apr. 2017, pp. 328-337.
Evans et al., "Molecular Cloning of a cDNA Encoding Canine Factor IX", Blood, vol. 74, No. 1, Jul. 1989, pp. 202-212.
Evens et al., "Haemophilia Gene Therapy: From Trailblazer to Gamechanger", Haemophilia, vol. 24, 2018, pp. 50-59.
Fallaux et al., "Who's Afraid of Replication-competent Adenoviruses?", Gene Therapy, vol. 6, No. 5, May 1999, pp. 709-712.
Finn et al., "Factor IX-R338L (FIX Padua) as a Novel Alternative for the Treatment of Canine Severe Hemophilia B", Molecular Therapy, vol. 18, Supplement 1, May 2010, p. S239.
Finn et al., "FIX-R338L (FIX Padua) as a Successful Alternative for the Treatment of Canine Severe Hemophilia B", Blood, vol. 114, No. 22, Nov. 2009, pp. 694-694.
Finn et al., "The Efficacy and the Risk of Immunogenicity of FIX Padua (R338L) in Hemophilia B Dogs Treated by AAV Muscle Gene Therapy", Blood, The Journal of the American Society of Hematology, vol. 120, No. 23, Nov. 29, 2012, pp. 4521-4523.
Flotte et al., "Adeno-Associated Viral Vectors for Gene Therapy", Laboratory Techniques in Biochemistry and Molecular Biology, vol. 31, 2005, 45 pages.
Franchini et al., "Treatment of Hemophilia B: Focus on Recombinant Factor IX", Biologics: Targets and Therapy, vol. 7, No. 1, 2013, pp. 33-38.
French et al., "Complete Correction of Hemophilia B Phenotype by Fix-padua Skeletal Muscle Gene Therapy in an Inhibitor-Prone Dog Model", Blood Advances, vol. 2, No. 5, Mar. 13, 2018, pp. 505-508.
French et al., "What is a Conservative Substitution?", Journal of Molecular Evolution, vol. 19, Mar. 1983, pp. 171-175.
Friedler et al., "Development of a Functional Backbone Cyclic Mimetic of the HIV-1 Tat Arginine-Rich Motif", The Journal of Biological Chemistry, vol. 275, No. 31, Aug. 2000, pp. 23783-23789.
Furie et al., "A Practical Guide to the Evaluation and Treatment of Hemophilia", Blood, vol. 84, No. 1, Jul. 1, 1994, pp. 3-9.
Gao et al., "Clades of Adeno-Associated Viruses Are Widely Disseminated in Human Tissues", Journal of Virology, vol. 78, No. 12, Jun. 2004, pp. 6381-6388.
Gao et al., "Novel Adeno-Associated Viruses from Rhesus Monkeys as Vectors for Human Gene Therapy", Proceedings of the National Academy of Sciences of the United States of America, vol. 99, No. 18, Sep. 3, 2002, pp. 11854-11859.
George et al., "Hemophilia B Gene Therapy with a High-Specific-Activity Factor IX Variant", The New England Journal of Medicine, vol. 377, No. 23 (Exhibit 2079), Dec. 7, 2017, pp. 2215-2227.
Giannelli et al., "Haemophilia B (Sixth Edition): A Database of Point Mutations and Short Additions and Deletions", Nucleic Acids Research, vol. 24, No. 1, Jan. 1, 1996, pp. 103-118.
Giannelli et al., "Haemophilia B: Database of Point Mutations and Short Additions and Deletions", Nucleic Acids Research, vol. 18, No. 14, 1990, pp. 4053-4059.
Goree et al., "Characterization of the Mutations Causing Hemophilia B in 2 Domestic Cats", Journal of Veterinary Internal Medicine, vol. 19, No. 2, Mar.-Apr. 2005, pp. 200-204.
Gostout et al., "Germline Mutations in The Factor Ix Gene: A Comparison Of The Pattern In Caucasians And Non-Caucasians", Human Molecular Genetics, vol. 2, No. 3, Mar. 1993, pp. 293-298.
Graham et al., "The Malmo Polymorphism of Coagulation Factor IX, An Immunologic Polymorphism Due to Dimorphism of Residue 148 That is in Linkage Disequilibrium with Two Other F.IX Polymorphisms", American Journal of Human Genetics, vol. 42, No. 4, Apr. 1988, pp. 573-580.
Green , "Hemophilia B Mutational Analysis", Hemostasis and Thrombosis Protocols, vol. 31, 1999, pp. 159-167.
Gui et al., "Circulating and Binding Characteristics of Wild-Type Factor IX and Certain Gia Domain Mutants in Vivo", Blood, vol. 100, No. 1, 2002, pp. 153-158.

(56) References Cited

OTHER PUBLICATIONS

Hamaguchi et al., "Expression and Characterization of Human Factor IX", The Journal of Biological Chemistry, vol. 266, No. 23, Aug. 15, 1991, pp. 15213-15220.
Hamaguchi et al., "Mutations in the Catalytic Domain of Factor IX That Are Related to the Subclass Hemophilia Bm", Biochemistry, vol. 32, No. 25, Jun. 29, 1993, pp. 6324-6329.
Hasbrouck et al., "AAV-Mediated Gene Transfer for the Treatment of Hemophilia B: Problems and Prospects", Gene Therapy, vol. 15, No. 11, Jul. 2008, pp. 870-875.
Hertzberg et al., "Construction, Expression, and Characterization of a Chimera of Factor IX and Factor X", The Journal of Biological Chemistry, vol. 267, No. 21, Jul. 25, 1992, pp. 14759-14766.
Herzog et al., "Influence of Vector Dose on Factor Ix-specific T and B Cell Responses in Muscle-directed Gene Therapy", Human Gene Therapy, vol. 13, No. 11, Jul. 20, 2002, pp. 1281-1291.
Herzog et al., "Long-Term Correction of Canine Hemophilia B by Gene Transfer of Blood Coagulation Factor IX Mediated by Adeno-Associated Viral Vector", Nature Medicine, vol. 5, No. 1, Jan. 1999, pp. 56-63.
Herzog et al., "Stable Gene Transfer and Expression of Human Blood Coagulation Factor IX After Intramuscular Injection of Recombinant Adeno-associated Virus", Proceedings of the National Academy of Sciences of the United States of America, vol. 94, May 1997, pp. 5804-5809.
High , "The Gene Therapy Journey for Hemophilia: Are We There Yet?", Blood, vol. 120, No. 23, Nov. 29, 2012, pp. 4482-4487.
Hopfner et al., "Converting Blood Coagulation Factor 1Xa into Factor Xa: Dramatic Increase in Amidolytic Activity Identifies Important Active Site Determinants", The European Molecular Biology Organization Journal, vol. 16, No. 22, Nov. 15, 1997, pp. 6626-6635.
IPR2020-00388 , "Judgement Granting Request for Adverse Judgement after Institution of Trial", Mar. 25, 2021, 6 pages.
IPR2021-00925 , "Affidavit of Duncan Hall re: Internet Archive Records regarding Ex. 1062, Monahan; Ex. 1063, Monahan II; submitted as Exhibit 1086", May 4, 2021, 280 pages.
IPR2021-00925 , "Corrected Declaration of James L. Mullins. Ph.D.", Before the Patent Trial and Appeal Board, Jan. 6, 2022, 831 pages.
IPR2021-00925 , "Decision Granting Institution of Inter Partes Review", Nov. 17, 2021, 33 pages.
IPR2021-00925 , "Decision Granting Patent Owner's Unopposed Motions for Admission Pro Hac Vice of Joshua L. Stern and James M. Lyons 37 C.F.R. § 42.10", Before the Patent Trial and Appeal Board, Feb. 8, 2022, 4 pages.
IPR2021-00925 , "Decision Granting Petitioner's Motions for Pro Hac Vice Admission of Kathryn S. Kayali 37 C.F.R. § 42.10", Before the Patent Trial and Appeal Board, Jan. 25, 2022, 4 pages.
IPR2021-00925 , "Declaration of James L. Mullins, Ph.D., Exhibit 1061", May 6, 2021, 1659 pages.
IPR2021-00925 , "Declaration of Kathryn S. Kayali in Support of Motion for Pro Hac Vice Admission Pursuant to 37 C.F.R. § 42.10(C)", Before the Patent Trial and Appeal Board, Jan. 10, 2022, 5 pages.
IPR2021-00925 , "Declaration of Lee Pedersen, Ph.D., Executed May 6, 2021 Exhibit 1094", Jun. 5, 2021, 90 pages.
IPR2021-00925 , "File History of U.S. Appl. No. 14/981,981, Exhibit 1090", May 11, 2021, 2672 pages.
IPR2021-00925 , "File History of U.S. Appl. No. 15/650,070, Exhibit 1091", May 11, 2021, 150 pages.
IPR2021-00925 , "File History of U.S. Appl. No. 15/989,665, Exhibit 1089", May 11, 2021, 137 pages.
IPR2021-00925 , "File History of U.S. Pat. No. 9,249,405, as Exhibit 1010", May 11, 2021, 174 pages.
IPR2021-00925 , "Order Granting Petitioner's Motions for Pro Hac Vice Admission of Kathryn S. Kayali 37 C.F.R. § 42.10", Before the Patent Trial and Appeal Board, Jan. 25, 2022, 4 pages.
IPR2021-00925 , "Order Granting Petitioner's Unopposed Motion for Supplemental Information 37 C.F.R § 42.123(a)", Before the Patent Trial and Appeal Board, Jan. 12, 2022, 4 pages.
IPR2021-00925 , "Patent Owner's Sur-Reply", Sep. 21, 2021, 11 pages.
IPR2021-00925 , "Petition for Inter Partes Review of U.S. Pat. No. 9,982,248", May 11, 2021, 81 pages.
IPR2021-00925 , "Petitioner Pfizer Inc.'s First Updated Mandatory Notices", Before the Patent Trial and Appeal Board, Jan. 11, 2022, 5 pages.
IPR2021-00925 , "Petitioner's Authorized Reply to Patent Owner's Preliminary Response", Sep. 14, 2021, 5 pages.
IPR2021-00925 , "Pfizer Inc.'s Motion for Pro Hac Vice Admission of Kathryn S. Kayali Pursuant to 37 C.F.R. § 42.10(C)", Before the Patent Trial and Appeal Board, Jan. 11, 2022, 18 pages.
IPR2021-00925 , "PTAB email", Sep. 8, 2021, pp. 1-2.
IPR2021-00925 , "Scheduling Order", Nov. 17, 2021, 12 pages.
IPR2021-00925 , "Statutory Disclaimer under 37 CFR § 1.321(a) for U.S. Pat. No. 9,249,405 filed May 31, 2011, Exhibit 1092", May 11, 2021, 4 pages.
IPR2021-00925 , "UniQure N.V. SEC Form 10-K", Petition for Inter Partes Review of U.S. Pat. No. 9,982,248, Exhibit 1049, Mar. 1, 2021, 259 pages.
IPR2021-00926 , "Decision Granting Institution of Inter Partes Review", Nov. 17, 2021, 41 pages.
IPR2021-00926 , "Declaration of Kathryn S. Kayali in Support of Motion for Pro Hac Vice Admission Pursuant to 37 C.F.R. § 42.10(c)", Before the Patent Trial and Appeal Board, Jan. 10, 2022, 5 pages.
IPR2021-00926 , "Patent Owner's Sur-reply", Sep. 21, 2021, 11 pages.
IPR2021-00926 , "Petition for Inter Partes Review of U.S. Pat. No. 9,982,248", May 11, 2021, 80 pages.
IPR2021-00926 , "Petitioner Pfizer Inc.'s First Updated Mandatory Notices", Before the Patent Trial and Appeal Board, Jan. 11, 2022, 5 pages.
IPR2021-00926 , "Petitioner's Authorized Reply to Patent Owner's Preliminary Response", Sep. 14, 2021, 5 pages.
IPR2021-00926 , "Pfizer Inc.'s Motion for Pro Hac Vice Admission of Kathryn S. Kayali Pursuan to 37 C.F.R. § 42.10(c)", Before the Patent Trial and Appeal Board, Jan. 11, 2022, 18 pages.
IPR2021-00926 , "PTAB email", Sep. 8, 2021, pp. 1-2.
IPR2021-00926 , "Scheduling Order", Nov. 17, 2021, 12 pages.
IPR2021-00928 , "Decision Granting Institution of Inter Partes Review", Nov. 17, 2021, 37 pages.
IPR2021-00928 , "Declaration of Kathryn S. Kayali in Support of Motion for Pro Hac Vice Admission Pursuant to 37 C.F.R. § 42.10(c)", Before the Patent Trial and Appeal Board, Jan. 10, 2022, 5 pages.
IPR2021-00928 , "Patent Owner's Sur-Reply", Sep. 21, 2021, 11 pages.
IPR2021-00928 , "Petition for Inter Partes Review of U.S. Pat. No. 10,465,180", May 11, 2021, 76 pages.
IPR2021-00928 , "Petitioner Pfizer Inc.'s First Updated Mandatory Notices", Before the Patent Trial and Appeal Board, Jan. 11, 2022, 5 pages.
IPR2021-00928 , "Petitioner's Authorized Reply to Patent Owner's Preliminary Response", Sep. 14, 2021, 5 pages.
IPR2021-00928 , "Pfizer Inc.'s Motion for Pro Hac Vice Admission of Kathryn S. Kayali Pursuan to 37 C.F.R. § 42.10(c)", Before the Patent Trial and Appeal Board, Jan. 11, 2022, 18 pages.
IPR2021-00928 , "PTAB email", Sep. 8, 2021, pp. 1-2.
IPR2021-00928 , "Scheduling Order", Nov. 17, 2021, 12 pages.
Jacobs et al., "Adeno-Associated Viral Vectors for Correction of Inborn Errors of Metabolism: Progressing Towards Clinical Application", Current Pharmaceutical Design, vol. 17, No. 24, 2011, pp. 2500-2515.
Johson et al., "A Critical View on Conservative Mutations", Protein Engineering, vol. 14, No. 6, Jun. 1, 2001, pp. 397-402.
Kaczmarek , "Current status of Gene Therapy in Haemophilia", Presented at the 16th Annual Congress of the European Associate for Haemophilia and Allied Disorders (EAHAD), Feb. 7-10, 2023, Feb. 9, 2023, 62 pages.

(56) References Cited

OTHER PUBLICATIONS

Karlin et al., "Applications and Statistics for Multiple High-Scoring Segments in Molecular Sequences", Proceedings of the National Academy of Sciences USA, vol. 90, No. 12, Jun. 15, 1993, pp. 5873-5877.
Karlin et al., "Methods for Assessing the Statistical Significance of Molecular Sequence Features by Using General Scoring Schemes", Proceedings of the National Academy of Sciences, vol. 87, No. 6, Mar. 1990, pp. 2264-2268.
Kavakli et al., "Efficacy and Safety of Fidanacogene Elaparvovec in Adults with Moderately Severe to Severe Hemophilia B: the Phase 3 Benegene-2 Gene Therapy Trial", 16th Annual Congress of the European Associate for Haemophilila and Allied Disorders (EAHAD), Feb. 7-10, 2023, Manchester, UK, Feb. 2023, 15 pages.
Kay et al., "Evidence for Gene Transfer and Expression of Factor IX in Haemophilia B Patients Treated With an AAV Vector", Nature Genetics, vol. 24, No. 3, Mar. 2000, pp. 257-261.
Kay et al., "Viral Vectors for Gene Therapy: The Art of Turning Infectious Agents Into Vehicles of Therapeutics", Nature Medicine, vol. 7, No. 1, Jan. 2001, pp. 33-40.
Kettering et al., "The Rates of G:C-->T:A and G:C-->C:G Transversions at CpG Dinucleotides in the Human Factor IX Gene", American Journal of Human Genetics, vol. 54, No. 5, May 1994, pp. 831-835.
Khalilzadeh et al., "Process Development for Production of Recombinant Human Interferon-γ Expressed in *Escherichia coli*", Journal of Industrial Microbiology and Biotechnology, vol. 31, No. 2, Mar. 2004, pp. 63-69.
Kolata , "They Thought Hemophilia Was a 'Lifelong Thing.' They May Be Wrong", Available Online at: <https://www.nytimes.com/2018/08/13/health/hemophilia-gene-therapy.html>, Aug. 13, 2018, pp. 1-4.
Kolkman et al., "Regions 301-303 and 333-339 in the Catalytic Domain of Blood Coagulation Factor IX Are Factor VIII-interactive Sites Involved in Stimulation of Enzyme Activity", Biochemical Journal, vol. 339, No. 2, Apr. 1999, pp. 217-221.
Kowarsch et al., "Correlated Mutations: A Hallmark of Phenotypic Amino Acid Substitutions", Public Library of Science Computational Biology, vol. 6, No. 9, Sep. 16, 2010, pp. 1-13.
Kunkel , "Rapid and Efficient Site-Specific Mutagenesis Without Phenotypic Selection", Proceedings of the National Academy of Sciences of the United States of America, vol. 82, No. 2, Jan. 15, 1985, pp. 488-492.
Kurachi et al., "Isolation and Characterization of a CDNA Coding for Human Factor IX", Proceedings of the National Academy of Sciences of the United States of America, vol. 79, No. 2, Nov. 1982, pp. 6461-6464.
Kurachi et al., "Role of Intron I in Expression of the Human Factor IX Gene", Journal of Biological Chemistry, vol. 270, No. 10, Apr. 1995, pp. 5276-5281.
Lai et al., "Adenovirus and Adeno-Associated Virus Vectors", DNA and Cell Biology, vol. 21, No. 12, 2002, pp. 895-913.
Lillicrap , "Hemophilia Gene Therapy: An Overview", Textbook of Hemophilia, 2nd edition, (Exhibit 2072), 2010, 18 pages.
Lin et al., "Expression and Characterization of Human Factor IX and Factor IX-Factor X Chimeras in Mouse C127 Cells", Journal of Biological Chemistry, vol. 265, No. 1, Jan. 5, 1990, pp. 144-150.
Lin et al., "Generation of A Novel Factor IX with Augmented Clotting Activities in Vitro and in Vivo", Journal of Thrombosis and Haemostasis, vol. 8, No. 8, Aug. 2010, pp. 1773-1783.
Liu et al., "Hemophilic Factor Viii C1- and C2-domain Missense Mutations and Their Modeling to the 1.5-angstrom Human C2-domain Crystal Structure", Hemostasis, Thrombosis, and Vascular Biology, vol. 96, No. 3, Aug. 1, 2000, pp. 979-987.
Lollar , "Pathogenic antibodies to Coagulation factors. Part one: Factor VIII and Factor IX", Journal of Thrombosis and Haemostasis, vol. 2, No. 7, Jul. 2004, pp. 1082-1095.
Lowe , "Factor IX and Thrombosis", British Journal of Haematology, vol. 115, No. 3, 2001, pp. 507-513.
Lozier et al., "The Rhesus Macaque as an Animal Model for Hemophilia B Gene Therapy", Blood, vol. 93, No. 6, Mar. 15, 1999, pp. 1875-1881.
Lu et al., "Gene Therapy for Hemophilia B Mediated by Recombinant Adeno-Associated Viral Vector with hFIXR338A, a High Catalytic Activity Mutation of Human Coagulation Factor IX", Science China Life Sciences, vol. 44, No. 6, Dec. 2001, pp. 585-592.
Ludwig et al., "Identification of a Single Nucleotide C-to-T Transition and Five Different Deletions in Patients with Severe Hemophilia B", The American Journal of Human Genetics, vol. 45, No. 1, Jul. 1989, pp. 115-122.
Lui et al., "Nonsense Suppression in Approaches in Treating Hemophilia", Blood, vol. 112, No. 11, Nov. 2008, 1 page.
Malkov et al., "A Reexamination of the Propensities of Amino Acids Towards a Particular Secondary Structure: Classification of Amino Acids Based on Their Chemical Structure", Journal of Molecular Modeling, vol. 14, Aug. 2008, pp. 769-775.
Manno et al., "AAV-Mediated Factor IX Gene Transfer to Skeletal Muscle in Patients with Severe Hemophilia B", Blood, vol. 101, No. 8, Apr. 2003, pp. 2963-2972.
Manno et al., "Successful Transduction of Liver in Hemophilia by AAV-factor IX and Limitations Imposed by the Host Immune Response", Nature Medicine, vol. 12, No. 3, Mar. 2006, pp. 342-347.
Manno et al., "Supplemental Table 4, Successful Transduction of Liver in Hemophilia by AAV-Factor IX and Limitations Imposed by the Host Immune Response", Nature Medicine, vol. 12, No. 3, Feb. 12, 2006, 1 page.
Mathur et al., "Protease and EGF1 Domains of Factor IXa Play Distinct Roles in Binding to Factor VIIIa. Importance of Helix 330 (Helix 162 in Chymotrypsin) of Protease Domain of Factor IXa in Its Interaction with Factor VIIIa", Journal of Biological Chemistry, vol. 274, No. 26, Jun. 25, 1999, pp. 18477-18486.
Mayfield et al., "Expression and Assembly of a Fully Active Antibody in Algae", Proceedings of the National Academy of Sciences, vol. 100, No. 2, Jan. 21, 2003, pp. 438-442.
McCarty et al., "Integration of Adeno-Associated Virus (AAV) and Recombinant AAV Vectors", Annual Review of Genetics, vol. 38, 2004, pp. 819-845.
McCreary et al., "Human Dose Prediction of a Novel Factor IX Variant Gene Therapy Candidate (AMT-180) Mediating Clotting Independently of Facto VIII", American Society of Gene & Therapy (ASGCT) 23rd Virtual Annual Meeting, 2020, 2020, 1 page.
McGraw et al., "Evidence for a prevalent dimorphism in the activation peptide of human coagulation factor IX", Proceedings of the National Academy of Sciences of the United States of America, vol. 82, May 1985, pp. 2847-2851.
Melao , "UniQure Granted US Patent to Use FIX-Padua for Hemophilia B Gene Therapy", Nov. 6, 2019, 2 pages.
Miao et al., "Inclusion of the Hepatic Locus Control Region, an Intron, and Untranslated Region Increases and Stabilizes Hepatic Factor IX Gene Expression in Vivo but Not in Vitro", Molecular Therapy, vol. 1, No. 6, Jun. 2000, Jun. 2000, pp. 522-532.
Mingozzi et al., "Immune Responses to AAV in Clinical Trials", Current Gene Therapy, vol. 7, 2007, pp. 316-324.
Mingozzi et al., "Modulation of Tolerance to the Transgene Product in a Nonhuman Primate Model of AAV-mediated Gene Transfer to Liver", Gene Therapy, vol. 110, No. 7, Oct. 1, 2007, pp. 2334-2341.
Monahan et al., "Direct Intramuscular Injection With Recombinant AAV Vectors Results in Sustained Expression in a Dog Model of Hemophilia", Gene Therapy, vol. 5, No. 1, Mar. 4, 1998, pp. 40-49.
Monahan et al., "Employing a Gain-of-Function Factor IX Variant R338L to Advance the Efficacy and Safety of Hemophilia B Human Gene Therapy: Preclinical Evaluation Supporting an Ongoing Adeno-Associated Virus Clinical Trial", Human Gene Therapy, vol. 26, No. 2, 2015, pp. 69-81.
Monahan , "Gene Therapy in an Era of Emerging Treatment Options for Hemophilia B.", Journal of Thrombosis and Haemostasis, vol. 13, 2015, pp. S151-S160.
Monahan et al., "Update on a Phase 1/2 Open-Label Trial of BAX335, An Adeno-Associated Virus 8 (AAV8) Vector-Based

(56) References Cited

OTHER PUBLICATIONS

Gene Therapy Program for Hemophilia B: LB010", Journal of Thrombosis and Haemostasis, vol. 13, 2015, p. 87.
Muneta et al., "Large-Scale Production of Porcine Mature interleukin-18 (IL-18) in Silkworms Using a Hybrid Baculovirus Expression System", Journal of Veterinary Medical Science, vol. 65, No. 2, Feb. 2003, pp. 219-223.
Murphy et al., "Gene Therapy for Haemophilia", British Journal of Haematology, vol. 140, No. 5, Mar. 2008, pp. 479-487.
Nakai et al., "AAV Serotype 2 Vectors Preferentially Integrate Into Active Genes in Mice", Nature Genetics, vol. 34, No. 3, Jul. 2003, pp. 297-302.
Nakai et al., "Extrachromosomal Recombinant Adeno-Associated Virus Vector Genomes Are Primarily Responsible for Stable Liver Transduction In Vivo", Journal of Virology, vol. 75, No. 15, Aug. 1, 2001, pp. 6969-6976.
Nathwani et al., "Adenovirus-Associated Virus Vector-Mediated Gene Transfer in Hemophilia B", The New England Journal of Medicine, vol. 365, No. 25, Dec. 22, 2011, pp. 2357-2365.
Nathwani et al., "Haemophilia, The Journey in Search of a Cure. 1960-2020", British Society for Haematology 60th Anniversary Special Issue, vol. 191, No. 4, Nov. 13, 2020, pp. 573-578.
Nathwani et al., "Safe and Efficient Transduction of the Liver After Peripheral Vein Infusion of Self-Complementary AAV Vector Results in Stable Therapeutic Expression of Human Fix in Nonhuman Primates", Blood, vol. 109, No. 4, Feb. 15, 2007, pp. 1414-1421.
Nathwani et al., "Self-Complementary Adeno-Associated Virus Vectors Containing a Novel Liver-Specific Human Factor IX Expression Cassette Enable Highly Efficient Transduction of Murine and Nonhuman Primate Liver", Blood, vol. 107, No. 7, Apr. 1, 2006, pp. 2653-2661.
Nelson et al., "Principles of Biochemistry", Lehninger, Fifth Edition, 2008, 65 pages.
Ng et al., "Predicting Deleterious Amino Acid Substitutions", Genome Research, vol. 11, No. 5, May 2001, pp. 863-874.
Ng et al., "Predicting the Effects of Amino Acid Substitutions on Protein Function", Annual Review of Genomics and Human Genetics, vol. 7, 2006, pp. 61-80.
Nilsson et al., "Twenty-five Years' Experience of Prophylactic Treatment in Severe Haemophilia a and B", Journal of Internal Medicine, vol. 232, No. 1, Jul. 1, 1992, pp. 25-31.
Osborne , ""Padua" to the Metal: UniQure Fixes Sights on Quick Drive to Hemophilia B Try", Available Online at: https://www.bioworld.com/articles/391457-padua-to-the-metal-uniqure-fixes-sights-on-quick-drive-to-hemophilia-b-try?v=preview, Oct. 2017, 3 pages.
Pace et al., "A Helix Propensity Scale Based on Experimental Studies of Peptides and Proteins", Biophysical Journal, vol. 75, No. 1, Jul. 1998, pp. 422-427.
Palmer et al., "Production of Human Factor IX in Animals by Genetically Modified Skin Fibroblasts: Potential Therapy for Hemophilia B", Blood, vol. 73, No. 2, Feb. 1989, pp. 438-445.
PCT/EP2009/061935 , "International Preliminary Report on Patentability", Oct. 28, 2009, 8 pages.
PCT/EP2009/061935 , "International Search Report and Written Opinion", Dec. 22, 2009, 11 pages.
Perera et al., "Modeling Human Zymogen Factor IX", Thrombosis and Haemostasis, vol. 85, No. 4, May 2001, pp. 596-603.
Perrin et al., "Update on Clinical Gene Therapy for Hemophilia", Blood, vol. 133, No. 5, Jan. 31, 2019, pp. 407-414.
Peyvandi et al., "Immunogenicity and Investigational AAV Gene Therapy", Spark Therapeutics, Feb. 8, 2023, 56 pages.
Pham et al., "Large-Scale Transient Transfection of Serum-Free Suspension-Growing HEK293 EBNA1 Cells: Peptone Additives Improve Cell Growth and Transfection Efficiency", Biotechnology and Bioengineering, vol. 84, No. 3, Nov. 2003, pp. 332-342.
Pintao et al., "High levels of protein C are determined by PROCR Haplotype 3", Journal ofThrombosis and Haemostasis, vol. 9, Issue 5, May 2011, pp. 969-976.
Pipe , "Bioengineered Molecules for the Management of Haemophilia: Promise and Remaining Challenges", Haemophilia, vol. 24, 2018, pp. 68-75.
Pipe et al., "Gene Therapy with Etranacogene Dezaparvovec for Hemophilia B", The New England Journal of Medicine, vol. 388, No. 8, Feb. 23, 2023, pp. 706-718.
Pipe et al., "One Year Data From a Phase 2b Trial of AMT-061 (AAV5-Padua Fix Variant), an Enhanced Vector for Gene Transfer in Adult With Sever or Moderate-Severe Hemophilia B", Presented at the 61st American Society of Hematology Annual Meeting & Exposition, Orlando, FL, Dec. 7-10, 2019, 1 page.
Platis et al., "High Yield Expression, Refolding, and Characterization of Recombinant Interferon α2/α8 Hybrids in *Escherichia coli*", Protein Expression and Purification, vol. 31, No. 2, Oct. 2003, pp. 222-230.
Ponder , "Gene Therapy for Hemophilia", Current Opinion in Hematology, vol. 13, No. 5, 2006, pp. 301-307.
Pons-Faudoa et al., "Advanced Implantable Drug Delivery Technologies: Transforming the Clinical Landscape of Therapeutics for Chronic Diseases", Biomedical Microdevices, vol. 21, No. 2, 2019, 46 pages.
Qu et al., "Separation of Adeno-Associated Virus Type 2 Empty Particles From Genome Containing Vectors by Anion-Exchange Column Chromatography", Journal of Virological Methods, vol. 140, Nos. 1-2, Mar. 2007, pp. 183-192.
Quillen Jr. et al., "Continuing Patent Applications and Performance of the U.S. Patent and Trademark Office—Extended", The Federal Circuit Bar Journal, vol. 12, No. 1, Aug. 2002, pp. 35-55.
Ragni , "Safe Passage: A Plea for Safety in Hemophilia Gene Therapy", Molecular Therapy, vol. 6, No. 4, Oct. 2002, pp. 436-440.
Reitsma , "Declaration", Aug. 13, 2021, 12 pages.
Rinde , "The Death of Jesse Gelsinger, 20 Years Later", Science History Institute, Available online at https://www.sciencehistory.org/distillations/the-death-of-jesse-gelsinger-20-years-later, Jun. 4, 2019, pp. 1-17.
Roberts et al., "Current Management of Hemophilia B", Hematology/Oncology Clinics of North America, vol. 7, No. 6, Dec. 1993, pp. 1269-1280.
Rohlena et al., "Residues Phe342-Asn346 of Activated Coagulation Factor IX Contribute to the Interaction with Low Density Lipoprotein Receptor-Related Protein", Journal of Biological Chemistry, vol. 278, No. 11, Mar. 14, 2003, pp. 9394-9401.
Roth et al., "Human Recombinant Factor IX: Safety and Efficacy Studies in Hemophilia B Patients Previously Treated With Plasma-Derived Factor IX Concentrates", Blood, vol. 98, No. 13, Dec. 1, 2001, pp. 3600-3606.
Sabatino et al., "Novel Hemophilia B Mouse Models Exhibiting a Range of Mutations in the Factor IX Gene", Blood, vol. 104, No. 9, Nov. 1, 2004, pp. 2767-2774.
Sambrook et al., "Molecular Cloning", A Laboratory Manual, vol. 2, Third Edition, 2001, 13 pages.
Samelson-Jones et al., "Evolutionary Insights into Coagulation Factor IX Padua and other High-Specific-Activity Variants", Blood Advance, vol. 5, No. 5, Mar. 9, 2021, pp. 1324-1332.
Samelson-Jones et al., "Investigations Into Anticoagulant Resistance and Enhanced Activation as Putative Molecular Mechanisms of the Hyperactivity of Factor IX Padua", Poster ISTH 2015, 2015, 1 page.
Samelson-Jones et al., "Protein-Engineered Coagulation Factors for Hemophilia Gene Therapy", Molecular Therapy-Methods & Clinical Development, vol. 12, Mar. 12, 2019, pp. 184-201.
Schaub et al., "Preclinical Studies of Recombinant Factor IX", Seminars in Hematology, vol. 35, No. 2, Apr. 1998, pp. 28-32.
Schiedner et al., "Genomic DNA Transfer With a High-Capacity Adenovirus Vector Results in Improved in Vivo Gene Expression and Decreased Toxicity", Nature Genetics, vol. 18, No. 2, Feb. 1998, pp. 180-183.
Schuettrumpf et al., "Factor IX Variants Improve Gene Therapy Efficacy for Hemophilia B", Blood, vol. 105, No. 6, Mar. 15, 2005, pp. 2316-2323.
Schuettrumpf et al., "IPR2020-00388", Factor IX variants improve gene therapy efficacy for hemophilia B, Library stamped copy, submitted as Exhibit 1056, 2005, 10 pages.

(56) References Cited

OTHER PUBLICATIONS

Schuettrumpf et al., "The Use of Factor IX Variants Improves AAv-Mediated Gene Therapy for Hemophilia B", 44th Annual Meeting of the American-Society-of-Hematology, Blood, vol. 100, Nov. 2002.
Sibbald , "Death But One Unintended Consequence of Gene-Therapy Trial", JAMC, vol. 164, No. 11, Gelsinger Article, May 2001, 1 page.
Simioni et al., "Evidence of the First X-Linked Thrombophilia Due to a Novel Mutation in Clotting Factor IX Gene Resulting in Hyperfunctional Fix: Factor IX Arginine 338 Leucine (Factor IX Padua)", International Society on Thrombosis and Haemostasis vol. 7 (Suppl. 2), 2009, 1 page.
Simioni et al., "Evidence of the first X-linked thrombophilia due to a novel mutation in clotting factor IX gene resulting in hyperfunctional fix: factor IX arginine 338 leucine (factor IX padua)", J. Thrombosis & Haemostasis, vol. 7 (Suppl. 2), 2009, 316 pages.
Simioni et al., "X-Linked Thrombophilia with a Mutant Factor IX (Factor IX Padua)", The New England Journal of Medicine, vol. 361, No. 17, Oct. 22, 2009, pp. 1671-1675.
Skoko et al., "Expression and Characterization of Human interferon-Beta1 in the Methylotrophic Yeast Pichia Pastoris", Biotechnology and Applied Biochemistry, vol. 38, No. 3, Dec. 2003, pp. 257-265.
Snyder et al., "Persistent and Therapeutic Concentrations of Human Factor IX in Mice After Hepatic Gene Transfer of Recombinant AAV Vectors", Nature Genetics, vol. 16, No. 3, Jul. 1997, pp. 270-276.
Soucie et al., "Occurrence of hemophilia in the United States", American Journal of Hematology, vol. 59, No. 4, Dec. 1998, pp. 288-294.
Spencer et al., "State of The Art: Gene Therapy of Haemophilia", Haemophilia, vol. 22, 2016, pp. 66-71.
Spiegel Jr. et al., "Structure of a Factor VIII C2 Domain-immunoglobulin G4kappa Fab Complex: Identification of an Inhibitory Antibody Epitope on the Surface of Factor VIII", Blood, vol. 98, No. 1, Jul. 1, 2001, pp. 13-19.
Spitzer et al., "Molecular Defect in Factor IXBm Lake Elsinore. Substitution of Ala390 by Val in the Catalytic Domain", Journal of Biological Chemistry, vol. 263, No. 22, Aug. 5, 1988, pp. 10545-10548.
Spitzer et al., "Replacement of Isoleucine-397 by Threonine in the Clotting Proteinase Factor Ixa (Los Angeles and Long Beach Variants) Affects Macromolecular Catalysis but Not L-Tosylarginine Methyl Ester Hydrolysis. Lack of Correlation Between the Ox Brain Prothrombin Ti", Biochemical Journal, vol. 265, No. 1, Jan. 1, 1990, pp. 219-225.
St George , "Gene Therapy Progress and Prospects: Adenoviral Vectors", Gene Therapy, vol. 10, 2003, pp. 1135-1141.
Stryer , "Biochemistry", Fourth Edition, W.H. Freeman and Company, 1995, pp. 18-23.
Taylor , "UniQure Edges Closer to Haemophilia B Gene Therapy Ok", Available Online at: <http://www.pmlive.com/pharma_news/uniqure_edges_closer_to_haemophilia_b_gene_therapy_ok_1277913>, Feb. 2019, 3 pages.
Toomey et al., "Inhibition of Factor IX(a) Is Protective in a Rat Model of Thromboembolic Stroke", Stroke, vol. 33, No. 2, Feb. 2002, pp. 578-585.
"Transcription of Video File: American Society for Microbiology Principles of Virology 4th edition Vincent Racaniello and Dr. Katherine High," Oct. 1, 2014, 50 pages, Digital Evidence Group, Washington, D.C., Video file available online at: https://www.youtube.com/watch?v=S6gDrhTwBO8.
"Transcription of Video File: Progress, Potential, and Possibilities Dr. Katherine High," Aug. 11, 2022, 69 pages, Digital Evidence Group, Washington, D.C., Video file available online at: https://www.youtube.com/watch?v=11YaFf4RrA4.
Tretiakova et al., "Realizing the Promise of Gene Therapy Through Collaboration and Partnering: Pfizer's View", Nature, vol. 564, 2018, pp. Ex.2064-1-Ex.2064-5.
Tsang et al., "A Factor IX Mutation, Verified by Direct Genomic Sequencing, Causes Haemophilia B by a Novel Mechanism", The EMBO Journal, vol. 7, No. 10, Oct. 1988, pp. 3009-3015.
Vandenberghe et al., "Heparin Binding Directs Activation of T Cells Against Adeno-Associated Virus Serotype 2 Capsid", Nature Medicine, vol. 12, No. 8, Aug. 2006, pp. 967-971.
Vandendriessche et al., "Hyperactive Factor IX Padua: A Game-Changer For Hemophilia Gene Therapy", Molecular Therapy, vol. 26, No. 1, 2018, pp. 14-16.
Von Drygalski et al., "Etranacogene Dezaparvovec (AMT-061 Phase 2b): Normal/Near Normal FIX Activity and Bleed Cessation in Hemophilia B", Blood Advances, vol. 3, No. 21, Nov. 12, 2019, pp. 3241-3247.
Vorburger et al., "Adenoviral Gene Therapy", The Oncologist, vol. 7, 2002, pp. 46-59.
Wajih et al., "Increased Production of Functional Recombinant Human Clotting Factor IX by Baby Hamster Kidney Cells Engineered to Overexpress VKORC1, the Vitamin K 2, 3-epoxide-reducing Enzyme of the Vitamin K Cycle", Journal of Biological Chemistry, vol. 280, No. 36, Sep. 9, 2005, pp. 31603-31607.
Wallmark et al., "Population Genetics of the Malmo Polymorphism of Coagulation Factor IX", Hum Hered, vol. 41, 1991, pp. 391-396.
Walter et al., "Successful Expression of Human Factor IX Following Repeat Administration of Adenoviral Vector in Mice", Proceedings of the National Academy of Sciences of the United States of America, vol. 93, No. 7, Apr. 2, 1996, pp. 3056-3061.
Wang et al., "A Factor IX-Deficient Mouse Model for Hemophilia B Gene Therapy", Proceedings of the National Academy of Sciences, vol. 94, No. 21, Oct. 1997, pp. 11563-11566.
Wang et al., "CRISPR/Cas9-Mediated in Vivo Gene Targeting Corrects Hemostasis in Newborn and Adult Factor IX—Knockout Mice", Blood, The Journal of the American Society of Hematology, vol. 133, Issue 26, 2019, pp. 2745-2752.
Wang et al., "Cross-Presentation of Adeno-Associated Virus Serotype 2 Capsids Activates Cytotoxic T Cells but Does Not Render Hepatocytes Effective Cytolytic Targets", Human Gene Therapy, vol. 18, No. 3, Mar. 2007, pp. 185-194.
Wang et al., "Predicting Functional Impact of Single Amino Acid Polymorphisms by Integrating Sequence and Structural Features", Institute of Electrical and Electronics Engineers International Conference on Systems Biology, Sep. 2-4, 2011, pp. 18-26.
Wang et al., "Sustained Correction of Disease in Naive and AAV2-Pretreated Hemophilia B Dogs: AAV2/8-Mediated, Liver-Directed Gene Therapy", Blood, vol. 105, No. 8, Apr. 15, 2005, pp. 3079-3086.
Ware et al., "Genetic Defect Responsible for the Dysfunctional Protein: Factor IX Long Beach", Blood, vol. 72, No. 2, Aug. 1988, pp. 820-822.
Waters , "Degradation of Mutant Proteins, Underlying "Loss of Function" Phenotypes, Plays a Major Role in Genetic Disease", Current Issues in Molecular Biology, vol. 3, 2001, pp. 57-66.
Weber et al., "Development of Methods for the Selective Measurement of the Single Amino Acid Exchange Variant Coagulation Factor IX Padua", Molecular Therapy—Methods & Clinical Development, vol. 10, Sep. 21, 2018, pp. 29-37.
Weitzman et al., "Adeno-Associated Virus Biology", Humana Press, 2012, pp. 1-23.
Wexler , "Promising Interim Results Reported for uniQure's Gene Therapy AMT-061 in Phase 2b Hemophilia B Trial", UniQure, IPR2020-00388, Ex. 2003-5, Nov. 1, 2019, 5 pages.
White et al., "Recombinant Factor IX", Thrombosis and Haemostasis , vol. 78, No. 1, 1997, pp. 261-265.
Wolberg et al., "Characterization of γ-Carboxyglutamic Acid Residue 21 of Human Factor IX", Biochemistry, vol. 35, No. 32, 1996, pp. 10321-10327.
Wright et al., "Identification of Factors that Contribute to Recombinant AAV2 Particle Aggregation and Methods to Prevent its Occurrence During Vector Purification and Formulation", Molecular Therapy, vol. 12, No. 1, Jul. 2005, pp. 171-178.
Wu et al., "Adeno-Associated Virus Serotypes: Vector Toolkit for Human Gene Therapy", Molecular Therapy, vol. 14, Issue 3, Sep. 2006, pp. 316-327.

(56) References Cited

OTHER PUBLICATIONS

Wu et al., "Simplified Gene Synthesis: A One-Step Approach to PCR-Based Gene Construction", Journal of biotechnology, vol. 124, No. 3, Jul. 25, 2006, pp. 496-503.
Xiao , "Virus-Based Vectors for Gene Expression in Mammalian Cells: Adeno-Associated Virus", Chapter 3.4, Gene Transfer and Expression in Mammalian Cells, vol. 38, 2003, pp. 93-108.
Yampolsky et al., "The Exchangeability of Amino Acids in Proteins", Genetics, vol. 170, No. 4, May 11, 2005, pp. 1459-1472.
Yan , "The Current Feature of the Study on Human Coagulation Factor IX Mutant", Hereditas, vol. 27, No. 5, Oct. 2005, pp. 833-838.
Yan et al., "Transgenic Mice Can Express Mutant Human Coagulation Factor IX with Higher Level of Clotting Activity", Biochemical Genetics, vol. 44, Nos. 7-8, Aug. 2006, pp. 349-360.
Yao et al., "Expression of Human Factor IX in Rat Capillary Endothelial Cells: Toward Somatic Gene Therapy for Hemophilia B", Proceedings of the National Academy of Sciences of the United States of America, vol. 88, No. 18, Sep. 15, 1991, pp. 8101-8105.
Yoshitake et al., "Nucleotide Sequence of the Gene for Human Factor IX (Antihemophilic Factor B)", Biochemistry, vol. 24, No. 14, Jul. 1, 1985, pp. 3736-3750.
Young et al., "Three Novel and One C31133T (Arg-338—Stop) Mutations of Antihemophilic Factor IX Gene Detected in Taiwan", Zhonghua Yi Xue Za Zhi Taipei, vol. 57, No. 4, Apr. 1996, pp. 241-246.
Zhong et al., "First Epidermal Growth Factor-Like Domain of Human Blood Coagulation Factor IX is Required for Its Activation by Factor VIIa/Tissue Factor but Not by Factor XIa", Proceedings of the National Academy of Sciences of the United States of America, Biochemistry, vol. 91, No. 9, Apr. 1994, pp. 3574-3578.
U.S. Appl. No. 17/213,848 "Non-Final Office Action", Apr. 22, 2024, 12 pages.
U.S. Appl. No. 17/213,897, "Non-Final Office Action", Apr. 22, 2024, 14 pages.
"BeneFix Summary of Product Characteristics", European Medicines Agency (EMEA) available at http://www.emea.europa.eu/, Aug. 27, 2007, 75 pages.
"FDA Accepts Pfizer's Application for Hemophilia B Gene Therapy Fidanacogene Elaparvovec", Businesswire; available at www.businesswire.com/news/home/20230627431780/en/, Jun. 27, 2023.
"Hemgenix Summary of Product Characteristics", European Medicines Agency available at http://www.ema.europa.eu, 2023, 22 pages.
"Human Coagulation Factor IX Gene Completecds", Database EMBL, accessed Sep. 26, 2023 from ebi.ac.uk/ena/browser/api/embl/K02402.1?lineLimit=1000, 15.
"Judgment Decision for Patent 3581650", *Pfizer Inc.* v. *Uniqure Biopharma B.V.*, Oct. 24, 2024, 40 pages.
"Pfizer Announces Positive Top-Line Results from Phase 3 Study of Hemophilia B Gene Therapy Candiate", Businesswire available at https://www.businesswire.com/news/home/20221229005024/en/, Dec. 29, 2022, 5 pages.
"Screenshot of Session Information", The XXII Congress of the International Society of Thrombosis and Hemostasis, Journal of Thrombosis and Hemostasis, vol. 7, Jul. 16, 2009, 1 page.
"Sequence Listing", Blast result, National Library of Medicine, Mar. 2, 2024, 1 page.
Brunetti, Pierri , et al., "Molecular Therapy", The American Society of Gene Therapy , vol. 16, Supplement 1, May 2008, 1 page.
EP19174517.3 , "Summons to Attend Oral Proceedings Pursuant to Rule 115(1) EPC", Oct. 31, 2024, 25 pages.
Hough, C. , et al., "Gene therapy for hemophilia: an imperative to succeed", Journal of Thrombosis and Haemostasis 3.6 (2005), pp. 1195-1205.
Kofler, Stefan , et al., "Crystallographically mapped ligand binding differs in high and low IgE binding isoforms of birch pollen allergen bet v 1", Journal of molecular biology 422.1 (2012), pp. 109-123.
Kofler, Stefan , et al., "Stabilization of the dimeric birch pollen allergen Bet v 1 impacts its immunological properties", Journal of Biological Chemistry 289.1 (2014), pp. 540-551.
Kuzmin, Dmitry A., et al., "The Clinical Landscape for AAV Gene Therapies", Nature Reviews, Drug Discovery, vol. 20, 2021, 12 pages.
Kyte , et al., "A Simple Method for Displaying the Hydropathic Character of a Protein", Journal of Molecular Biology, vol. 157, No. 1, May 5, 1982, pp. 105-132.
Lehninger, Albert L., et al., "Lehninger Principles of Biochemistry", 5th Edition, New York, W.H. Freeman and Company, 2008, pp. 119-120.
Lehninger, Albert L., et al., "Lehninger Principles of Biochemistry", 5th Ed., New York: W.H. Freeman and Company, 2008, pp. 73.
Lin, Chia-Ni , et al., "Engineered Factor IX with Augmented Clotting Activities in a Hemophilia B Mouse Model", Blood, The American Society of Hematology, Nov. 16, 2008, 2 pages.
Stryer, Lubert, "Biochemistry", W.H. Freeman and Company, Fourth Edition, 2000, 44 pages.
Marks, Lara , "Gene Therapy", What is Biotechnology, retrieved Oct. 20, 2021 from https://www.whatisbiotechnology.org/index.php/science/summary/gene-therapy/, Jan. 2018, pp. 12 pages.
Miesbach, W. , et al., "Five Year Data Confirms Stable Fix Expression and Sustained Reductions in Bleeding and Factor IX Use Following AMT-060 Gene Therapy in Adults with Severe or Moderate-severe Hemophilia B (Abstract)", Res Prac Thromb Haemost. 2021; 5 (suppl 2) accessed Mar. 15, 2024, Mar. 15, 2024, 2 pages.
Mingozzi, Federico , et al., "Induction of immune tolerance to coagulation factor IX antigen by in vivo hepatic gene transfer", The Journal of clinical investigation 111.9 (2003), pp. 1347-1356.
Mount, Jane D., et al., "Sustained phenotypic correction of hemophilia B dogs with a factor IX null mutation by liver-directed gene therapy", Blood, The Journal of the American Society of Hematology 99.8 (2002), pp. 2670-2676.
Pierce, G. F., et al., "Gene Therapy, Bioengineered Clotting Factors and Novel Technologies for Hemophilia Treatment", Journal of Thrombosis and Haemostasis, vol. 5, Jan. 11, 2007, 5 pages.
Pommié, Christelle , et al., "IMGT standardized criteria for statistical analysis of immunoglobulin V-Region amino acid properties", Journal of Molecular Recognition 17.1 (2004), pp. 17-32.
Simioni, Lara , et al., "Abstracts of the XXII Congress of the International Society of Thrombosis and Hemostasis", Extract from Journal of Thrombosis and Haemostasis, vol. 7, Boston MA, 2009, 1 page.
Chang et al., 1998, Changing Residue 338 in Human Factor IX from Arginine to Alanine Causes an Increase in Catalytic Activity, J. Biol. Chem., 273: 12089-12094.*
French et al., 1983, What is a Conservative Substitution?, J Mol Evol, 19: 171-175.*
Dayoff et al., 1978, A Model of Evolutionary Change in Proteins, Atlas of Protein Seq Struc, 5: 345-352.*
Altschul, S., et al., Basic local alignment search tool, J. Mol. Biol. 1990, 215: 403-410.
Yoshitake, S., et al., Nucleotide Sequence of the Gene for Human Factor IX (Antihemophilic Factor B), Biochemistry 1985, 24: 3736-3750.
Green, P.M. Hemophilia B mutational analysis, Methods in Molecular Medicine, 31: Homeostasis and Thrombosis Protocol 1996, 159-167.
Ahmad, S., et al., The Role of the First Growth Factor Domain of Human Factor IX a in Binding to Platelets and in Factor X Activation, Journal of Biological Chemistry 1992, 287: 8571-8576.
Altshcul, S., et al., Gapped BLAST and PSI-BLAST: a new generation of protein database search programs, Nucleic Acids Research 1997, 25: 3389-3402.
Ameri, A., et al., Myocardial fibrosis in mice with overexpression of human blood coagulation factor IX, Blood 2003, 101: 1871-1873.
Bowie, J., et al., Deciphering the message in protein sequences: tolerance to amino acid substitutions, Science 1990, 247: 1306-1310.
Anson, DS et al., The gene structure of human anti-haemophilic factor IX, EMBO Journal 1984, 3: 1053-1060.

(56) References Cited

OTHER PUBLICATIONS

Mathur, A., et al., Protease and EGF1 domains of factor IXa play a distinct roles in binding to factor VIIIa, Journal of Biological Chemistry 1999, 274: 18477-18488.
Yan, J., et al., Transgenic mice can express mutant human coagulation factor IX with higher level of clotting activity, Biochemical Genetics 2006, 44: 349-350.
Schueltrumpf, J., et al., Factor IX variants improve gene therapy efficacy for hemophilia B, Blood 2005, 105: 2316-2323.
Sabatino, D., et al., Novel hemophilia B mouse models exhibiting a range of mutations in the Factor IX gene, Blood 2004, 104: 2767-2774.
Simioni, P., et al., X-linked thrombophilia with a mutant factor IX (Factor IX Padua), New England Journal of Medicine 2009, 1671-1676.
Deveraux, J., et al., A comprehensive set of sequence analysis programs for VAX, Nucleic Acids Research 1984, 12: 387-395.
Friedler, A., et al., Development of a Functional Backbone Cyclic Mimetic of the HIV-1 Tat Arginine-rich Motif*, Journal of Biological Chemistry 2000, 275: 23783-23789.
Gui, T., et al., Circulating and binding characteristics of wild-type factor IX and certain Gla domain mutants in vivo, Blood 2002, 100: 153-158.
Karlin, S., et al., Methods for assessing the statistical significance of molecular sequence features by using general scoring schemes, PNAS 1990, 87: 2264-2268.
Karlin, S., et al., Applications and statistics for multiple high-scoring segments in molecular sequences PNAS 1993, 90: 5873-5877.
Khalilzadeh, R., et al., Process development for production of recombinant human interferon-*c* expressed in *Escherichia coli*, J. Ind. Microbiol. Biotechnol. 2004, 31: 63-69.
Kunkel, T., Rapid and efficient site-specific mutagenesis without phenotypic selection, PNAS 1985, 82: 488-492.
Kurachi, K., et al., Isolation and characterization of a cDNA coding for human factor IX, PNAS 1982, 79: 6461-6464.
Lin, S., et al., Expression and Characterization of Human Factor IX and Factor IXFactor X Chimeras in Mouse Cl27 Cells*, Journal of Biological Chemistry 1990, 265: 144-150.
Lowe, Factor IX and Thrombosis, British Journal of Haematology 2001, 115: 507-513.
Mayfield, S., et al., Expression and assembly of a fully active antibody in algae, PNAS 2003, 100: 438-442.
Muneta, Y., et al., Large-scale production of porcine mature interleukin-18 (IL-18) in silkworms using a hybrid baculovirus expression system, J. Vet. Med. Sci. 2003, 65: 219-223.
Murphy, S., et al., Gene therapy for haemophilia, British Journal of Haematology 2008, 140: 479-487.
Palmer, T., et al., Production of human factor IX in animals by genetically modified skin fibroblasts: potential therapy for Hemophilia B, Blood 1989, 73: 438-445.
Pham, P., et al., Large-Scale Transient Transfection of Serum-Free Suspension-Growing HEK293 EBNA1 Cells: Peptone Additives Improve Cell Growth and Transfection Efficiency, Biotechnology and Bioengineering 2003, 84: 332-342.
Plastis, D., et al., High yield expression, refolding, and characterization of recombinant interferon $\alpha2/\alpha8$ hybrids in *Escherichia coli*, Protein Expression and Purification 2003, 31: 222-230.
Toomey, J., et al., Inhibition of Factor IX(a) Is Protective in a Rat Model of Thromboembolic Stroke, Stroke 2002, 33: 578-585.
Wajih, N., et al., Increased Production of Functional Recombinant Human Clotting Factor IX by Baby Hamster Kidney Cells Engineered to Overexpress VKORC1, the Vitamin K 2,3-Epoxide-reducing Enzyme of the Vitamin K Cycle*, Journal of Biological Chemistry 2005, 280: 31603-31607.
Yao, S., et al., Expression of human factor IX in rat capillary endothelial cells: Toward somatic gene therapy for hemophilia B, PNAS 1991, 88: 8101-8105.
Skoko, N., et al., Expression and characterization of human interferon-$\beta1$ in the methylotrophic yeast *Pichia pastoris*, Biotechnol. Appl. Biochem. 2003, 38: 257-265.
Bond, M., et al., Biochemical characterization of recombinant factor IX, Seminars in Hermatology 1998, 35: 11-17.
PCT International Search Report issued for PCT Application No. PCT/EP2009/061935 filed on Sep. 15, 2009 in the name of Paolo Simioni.
PCT Written Opinion issued for PCT Application No. PCT/EP2009/061935 filed on Sep. 15, 2009 in the name of Paolo Simioni.
PCT International Preliminary Report on Patentability issued for PCT Application No. PCT/EP2009/061935 filed on Sep. 15, 2009 in the name of Paolo Simioni.
Wang, M. et al. *Predicting Functional Impact of Single Amino Acid Polymorphisms by Integrating Sequence and Structural Features*. IEEE International Conference on Systems Biology, 2011, pp. 18-26.
Ng, P.C., et al. *Predicting the Effects of Amino Acid Substitutions on Protein Function*. Annu. Rev. Genomics Hum. Genet., vol. 7, 2006, pp. 61-80.
Ng, P.C. et al. *Predicting Deleterious Amino Acid Substitutions*. Genome Res., vol. 11, 2001, pp. 863-874.
Yampolsky, L. Y. et al. *The Exchangeability of Amino Acids in Proteins*. Genetics, vol. 170, Aug. 2005, pp. 1459-1472.
Kowarsch, A. et al. *Correlated Mutations: A Hallmark of Phenotypic Amino Acid Substitutions*. PLoS Computational Biology, vol. 6(9), e1000923, Sep. 2010, pp. 1-13.
Betts, M.J. et al. *Amino Acid Properties and Consequences of Substitutions*. Bioinformatics for Geneticists. Chapter 14. Edited by Michael Barnes and Ian Gray. 2003, pp. 289-316.
STN—The Choice of Patent Experts. CAS Registry Fact Sheet. Apr. 2014, 1 pg.
Schaub, R. et al. "Preclinical Studies of Recombinant Factor IX" *Seminars in Hematology*, vol. 35, No. 2, Suppl 2 (April), 1998: pp. 28-32.
Franchini, M. et al. "Treatment of hemophilia B: focus on recombinant factor IX" *Biologics: Targets and Therapy* 2013:7 pp. 33-38.

* cited by examiner

```
CTCTCTGACAAAGATACGGTGGGTCCCACTGATGAACTGTGCTGCCACAGTAAATGTAGCCACTATGCCTATCTCCATTCTGAAGATGTGTCACTTCCTGTTTCAGACTCAAATCAGCCA
        10        20        30        40        50        60        70        80        90       100       110       120

CAGTGGCAGAAGCCCACAGAATCAGAGGTGAAATTTAATAATGACCACTGCCCATTCTCTTCACTTGTCCCAAGAGGCCATTGGAAATAGTCCAAAGACCCATTGAGGGAGATGGACATT
       130       140       150       160       170       180       190       200       210       220       230       240

                                                                                                  -48                 -40
                                                                                                   M  G  R  V  N  M  I  M  A  E  S  P
                                                                 ●
ATTTCCCAGAAGTAAATACAGCTCAGCTTGTACTTTGGTACAACTAATCGACCTTACCACTTTCACAACTTGCTAGCAGAGGTTATGCAGCGCGTGAACATGATCATGGCAGAATCACCA
       250       260       270       280       290       300       310       320       330       340       350       360

          -30                                 -20
 G  L  I  T  I  C  L  L  G  Y  L  L  S  A  E  C  T
GGCCTCATCACCATCTGCCTTTTAGGATATCTACTCAGTGCTGAATGTACAGGTTTGTTTCCTTTTTTAAAATACATTGAGTATGCTTGCCTTTTAGATATAGAAATATCTGATGCTGTC
       370       380       390       400       410       420       430       440       450       460       470       480

TTCTTCACTAAATTTTGATTACATGATTTGACAGCAATATTGAAGAGTCTAACAGCCAGCACGCAGGTTGGTAAGTACTGGTTCTTTGTTAGCTAGGTTTTCTTCTTCTTCATTTTTAAA
       490       500       510       520       530       540       550       560       570       580       590       600

-----------------------------------------------------------5400bp-----------------------------------------------------------

AATCTCCATGTGTATACAGTACTGTGGGAACATCACAGATTTTGGCTCCTATGCCCTAAAGAGAAATTGGCTTTCAGATTATTTGGATTAAAAACAAAGACTTTCTTAAGAGATGTAAAA
      6010      6020      6030      6040      6050      6060      6070      6080      6090      6100      6110      6120
                                                                                  -10                                 1
                                                                V  F  L  D  H  E  N  A  N  K  I  L  N  R  P  K  R  Y  N  S  G  K
TTTTCATGATGTTTTCTTTTTTGCTAAAACTAAAGAATTATTCTTTTACATTTCAGTTTTTCTTGATCATGAAAACGCCAACAAAATTCTGAATCGGCCAAAGAGGTATAATTCAGGTAA
      6130      6140      6150      6160      6170      6180      6190      6200      6210      6220      6230      6240
            10                                  20                                  30
  L  E  E  F  V  G  G  N  L  E  R  E  C  M  E  E  K  C  S  F  E  E  A  R  E  V  F  E  N  T  E  R  T
ATTGGAAGAGTTTGTTCAAGGGAACCTTGAGAGAGAATGTATGGAAGAAAAGTGTAGTTTTGAAGAAGCACGAGAAGTTTTTGAAAACACTGAAAGAACAGTGAGTATTTCCACATAATA
      6250      6260      6270      6280      6290      6300      6310      6320      6330      6340      6350      6360

CCCTTCAGATGCAGAGCATAGAATAGAAAATCTTTAAAAAGACACTTCTCTTTAAAATTTTAAAGCATCCATATATATTTATGTATGTTAAATGTTATAAAAGATAGGAAATCAATACCA
      6370      6380      6390      6400      6410      6420      6430      6440      6450      6460      6470      6480
                                                                  40
                                                                T  E  F  W  K  G  Y  V
AAACACTTTAGATATTACCGTTAATTTGTCTTCTTTTATTCTTTATAGACTGAATTTTGGAAGCAGTATGTTGGTAAGCAATTCATTTTATCCTCTAGCTAATATATGAAACATATGAGA
      6490      6500      6510      6520      6530      6540      6550      6560      6570      6580      6590      6600

-----------------------------------------------------------3960bp-----------------------------------------------------------

                                                                                 50                                  60
                                                                D  G  D  G  C  E  S  N  P  C  L  N  G  G  S  C  K  D  D
CAGGGGAGGACCGGGCATTCTAAGCAGTTTACGTGCCAATTCAATTTCTTAACCTATCTCAAAGATGGAGATCAGTGTGAGTCCAATCCATGTTTAAATGGCGGCAGTTGCAAGGATGAC
     10570     10580     10590     10600     10610     10620     10630     10640     10650     10660     10670     10680
            70                                  80
 I  N  S  Y  E  C  W  C  P  F  G  F  E  G  K  N  C  E  L
ATTAATTCCTATGAATGTTGGTGTCCCTTTGGATTTGAAGGAAAGAACTGTGAATTAGGTAAGTAACTATTTTTTGAATACTCATGGTTCAAAGTTTCCCTCTGAAACAAGTTGAAACTG
     10690     10700     10710     10720     10730     10740     10750     10760     10770     10780     10790     10800

-----------------------------------------------------------7320bp-----------------------------------------------------------

AAAATTTCTCTCCCCAACGTATATTGGGGGCAACATGAATGCCCCCAATGTATATTTGACCCATACATGAGTCAGTAGTTCCATGTACTTTTTAGAAATGCATGTTAAATGATGCTGTTA
     18130     18140     18150     18160     18170     18180     18190     18200     18210     18220     18230     18240
                                         90                                  100                                 110
                         D  V  T  C  N  I  K  N~ G  R  C  E  G  F  C  K  N  S  A  D  N  K  V  V  C  S  C  T  E  G  Y  R  L
CTGTCTATTTTGCTTCTTTTAGATGTAACATGTAACATTAAGAATGGCAGATGCGAGCAGTTTTGTAAAAATAGTGCTGATAACAAGGTGGTTTGCTCCTGTACTGAGGGATATCGACTT
     18250     18260     18270     18280     18290     18300     18310     18320     18330     18340     18350     18360
    120
 A  E  N  G  K  S  C  E  P  A
GCAGAAAACCAGAAGTCCTGTGAACCAGCAGGTCATAATCTGAATAAGATTTTTTAAAGAAAATCTGTATCTGAAACTTCAGCATTTTAACAAACCTACATAATTTTAATTCCTACTTGA
     18370     18380     18390     18400     18410     18420     18430     18440     18450     18460     18470     18480

-----------------------------------------------------------2400bp-----------------------------------------------------------

                                                                                                 130                     140
                                                                                                 V  P  F  P  C  G  R  V  S  V  S  G  T
CCTCAATCTCAATTTTTGTAATACATGTTCCATTTGCCAATGAGAAATATCAGGTTACTAATTTTTCTTCTATTTTTCTAGTGCCATTTCCATGTGGAAGAGTTTCTGTTTCACAAACTT
     20890     20900     20910     20920     20930     20940     20950     20960     20970     20980     20990     21000
                         150                                 160                                 170                     180
S  K  L  T  R  A  E  A  V  F  P  D  V  D  Y  V  N  S  T  E  A  E  T  I  L  D  N  I  T  G  S  T  G  S  F  N  D  F  T  R
CTAAGCTCACCCGTGCTGAGGCTGTTTTTCCTGATGTGGACTATGTAAATTCTACTGAAGCTGAAACCATTTTGGATAACATCACTCAAAGCACCCAATCATTTAATGACTTCACTCGGG
     21010     21020     21030     21040     21050     21060     21070     21080     21090     21100     21110     21120
                         190
V  V  G  G  E  D  A  K  P  G  G  F  P  W  G
TTGTTGGTGGAGAAGATGCCAAACCAGGTCAATTCCCTTGGCAGGTACTTTATACTGATGGTGTGTCAAAACTGGAGCTCAGCTGGCAAGACACAGGCCAGGTGGGAGACTGAGGCTATT
     21130     21140     21150     21160     21170     21180     21190     21200     21210     21220     21230     21240

-----------------------------------------------------------9960bp-----------------------------------------------------------

AAAGCTCACATTTCCAGAAACATTCCATTTCTGCCAGCACCTAGAAGCCAATATTTTGCCTATTCCTGTAACCAGCACACATATTTATTTTTTTCTAGATCAAATGTATTATGCAGTAAG
     31090     31100     31110     31120     31130     31140     31150     31160     31170     31180     31190     31200
                                         200                                 210                                 220
                         V  V  L  N  G  K  V  D  A  F  C  G  G  S  I  V  N  E  K  W  I  V  T  A  A  H  C  V  E  T  G  V  K
AGTCTTAATTTTGTTTTCACAGGTTGTTTTGAATGGTAAAGTTGATGCATTCTGTGGAGGCTCTATCGTTAATGAAAAATGGATTGTAACTGCTGCCCACTGTGTTGAAACTGGTGTTAA
     31210     31220     31230     31240     31250     31260     31270     31280     31290     31300     31310     31320
   230
  I  T  V  V  A
AATTACAGTTGTCGCAGGTAAATACACAGAAAGAATAATAATCTGCAGCACCACTAGCTCTTTAATATGATTGGTACACCATATTTTACTAAGGTCTAATAAAATTGTTGTTGAATAAAT
     31330     31340     31350     31360     31370     31380     31390     31400     31410     31420     31430     31440
```

FIG. 2

```
TGGGCTAAAGGCAGAAGGGTCATAATTTCAGAACCCACGTCGCACCGTCCTCCAAGCATCCATAGTTCTTTTGATATACCCCTATTATCACTCATTTCAGTGAGGTACAATTAGTTCTTG
     31450     31460     31470     31480     31490     31500     31510     31520     31530     31540     31550     31560

ATGTAGCCATTTCCATACCAGAAGGCCTTCCCAAAAATCAGTGTCATGTCACCGATCCTTTTATCTCTGGTGCTTGGCACAACCTGTAGCAGGTCCTCAGAAAACAAACATTTGAATTAA
     31570     31580     31590     31600     31610     31620     31630     31640     31650     31660     31670     31680

TGGCCAAATGAGTTTGTGCTCAAAAAAGGGGTGAGGATACTTGAAATTTGGAAAATCTAGGATAATTCATGACTAGTGGATTCATTATCACCAATGAAAGGCTTATAACAGCATGAGTGA
     31690     31700     31710     31720     31730     31740     31750     31760     31770     31780     31790     31800

ACAGAACCATCTCTATGATAGTCCTGAATGGCTTTTTGGTCTGAAAAATATGCATTGGCTCTCATTACATTTAACCAAAATTATCACAATATAAGAATGAGATCTTTAACATTGCCAATT
     31810     31820     31830     31840     31850     31860     31870     31880     31890     31900     31910     31920

                                                                                                  240
                                                                                                  G  E  H  N  I  E  E  T  E  H  T  E
AGGTCAGTGGTCCCAAGTAGTCACTTAGAAAATCTGTGTATGTGAAATACTGTTTGTGACTTAAAATGAAATTTATTTTTAATAGGTGAACATAATATTGAGGAGACAGAACATACAGAG
     31930     31940     31950     31960     31970     31980     31990     32000     32010     32020     32030     32040

          250                                 260                                 270                                 280
 G  K  R  N  V  I  R  I  I  P  H  H  N  Y  N  A  A  I  N  K  Y  N  H  D  I  A  L  L  E  L  D  E  P  L  V  L  N  S  Y  V
CAAAAGCGAAATGTGATTCGAATTATTCCTCACCACAACTACAATGCAGCTATTAATAAGTACAACCATGACATTGCCCTTCTGGAACTGGACGAACCCTTAGTGCTAAACAGCTACGTT
     32050     32060     32070     32080     32090     32100     32110     32120     32130     32140     32150     32160

          290                                 300                                 310                                 320
 T  P  I  C  I  A  D  K  E  Y  T  N  I  F  L  K  F  G  S  G  Y  V  S  G  W  G  R  V  F  H  K  G  R  S  A  L  V  L  G  Y
ACACCTATTTGCATTGCTGACAAGGAATACACGAACATCTTCCTCAAATTTGGATCTGGCTATGTAAGTGGCTGGGGAAGAGTCTTCCACAAAGGGAGATCAGCTTTAGTTCTTCAGTAC
     32170     32180     32190     32200     32210     32220     32230     32240     32250     32260     32270     32280

          330                                 340                                 350                                 360
 L  R  V  P  L  V  D  R  A  T  C  L  R  S  T  K  F  T  I  Y  N  N  M  F  C  A  G  F  H  E  G  G  R  D  S  C  G  G  D  S
CTTAGAGTTCCACTTGTTGACCGAGCCACATGTCTTCGATCTACAAAGTTCACCATCTATAACAACATGTTCTGTGCTGGCTTCCATGAAGGAGGTAGAGATTCATGTCAAGGAGATAGT
     32290     32300     32310     32320     32330     32340     32350     32360     32370     32380     32390     32400

          370                                 380                                 390                                 400
 G  G  P  H  V  T  E  V  E  G  T  S  F  L  T  G  I  I  S  W  G  E  E  C  A  M  K  G  K  Y  G  I  Y  T  K  V  S  R  Y  V
GGGGGACCCCATGTTACTGAAGTGGAAGGGACCAGTTTCTTAACTGGAATTATTAGCTGGGGTGAAGAGTGTGCAATGAAAGGCAAATATGGAATATATACCAAGGTATCCCGGTATGTC
     32410     32420     32430     32440     32450     32460     32470     32480     32490     32500     32510     32520

          410       415
 N  W  I  K  E  K  T  K  L  T
AACTGGATTAAGGAAAAAACAAAGCTCACTTAATGAAAGATGGATTTCCAAGGTTAATTCATTGGAATTGAAAATTAACAGGGCCTCTCACTAACTAATCACTTTCCCATCTTTTGTTAG
     32530     32540     32550     32560     32570     32580     32590     32600     32610     32620     32630     32640

ATTTGAATATATACATTCTATGATCATTGCTTTTTCTCTTTACAGGGGAGAATTTCATATTTTACCTGAGCAAATTGATTAGAAAATGGAACCACTAGAGGAATATAATGTGTTAGGAAA
     32650     32660     32670     32680     32690     32700     32710     32720     32730     32740     32750     32760

TTACAGTCATTTCTAAGGGCCCAGCCCTTGACAAAATTGTGAAGTTAAATTCTCCACTCTGTCCATCAGATACTATGGTTCTCCACTATGGCAACTAACTCACTCAATTTTCCCTCCTTA
     32770     32780     32790     32800     32810     32820     32830     32840     32850     32860     32870     32880

GCAGCATTCCATCTTCCCGATCTTCTTTGCTTCTCCAACCAAAACATCAATGTTTATTAGTTCTGTATACAGTACAGGATCTTTGGTCTACTCTATCACAAGGCCAGTACCACACTCATG
     32890     32900     32910     32920     32930     32940     32950     32960     32970     32980     32990     33000

AAGAAAGAACACAGGAGTAGCTGAGAGGCTAAAACTCATCAAAAACACTACTCCTTTTCCTCTACCCTATTCCTCAATCTTTTACCTTTTCCAAATCCCAATCCCCAAATCAGTTTTTCT
     33010     33020     33030     33040     33050     33060     33070     33080     33090     33100     33110     33120

CTTTCTTACTCCCTCTCTCCCTTTTACCCTCCATGGTCGTTAAAGGAGAGATGGGGAGCATCATTCTGTTATACTTCTGTACACAGTTATACATGTCTATCAAACCCAGACTTGCTTCCA
     33130     33140     33150     33160     33170     33180     33190     33200     33210     33220     33230     33240

TAGTGGGGACTTGCTTTTCAGAACATAGGGATGAAGTAAGGTGCCTGAAAAGTTTGGGGGAAAAGTTTCTTTCAGAGAGTTAAGTTATTTTATATATATAATATATATATAAAATATATA
     33250     33260     33270     33280     33290     33300     33310     33320     33330     33340     33350     33360

ATATACAATATAAATATATAGTGTGTGTGTATGCGTGTGTGTAGACACACACGCATACACACATATAATGGAAGCAATAAGCCATTCTAAGAGCTTGTATGGTTATGGAGGTCTGACT
     33370     33380     33390     33400     33410     33420     33430     33440     33450     33460     33470     33480

AGGCATGATTTGACGAAGGCAAGATTGGCATATCATTGTAACTAAAAAAGCTGACATTGACCCAGACATATTGTACTCTTTCTAAAAATAATAATAATAATGCTAACAGAAAGAAGAGAA
     33490     33500     33510     33520     33530     33540     33550     33560     33570     33580     33590     33600

CCGTTCGTTTGCAATCTACAGCTAGTAGAGACTTTGAGGAAGAATTCAACAGTGTGTCTTCAGCAGTGTTCAGAGCCAAGCAAGAAGTTGAAGTTGCCTAGACCAGAGGACATAAGTATC
     33610     33620     33630     33640     33650     33660     33670     33680     33690     33700     33710     33720

ATGTCTCCTTTAACTAGCATACCCCGAAGTGGAGAAGGGTGCAGCAGGCTCAAAGGCATAAGTCATTCCAATCAGCCAACTAAGTTGTCCTTTTCTGGTTTCGTGTTCACCATGGAACAT
     33730     33740     33750     33760     33770     33780     33790     33800     33810     33820     33830     33840

TTTGATTATAGTTAATCCTTCTATCTTGAATCTTCTAGAGAGTTGCTGACCAACTGACGTATGTTTCCCTTTGTGAATTAATAAACTGGTGTTCTGGTTCATACCTTGGCTTTTTGTGGA
     33850     33860     33870     33880     33890     33900     33910     33920     33930     33940     33950     33960

TTCCATTGATGTGAATCAGTCACCCTGTATTTGATGATGCATGGGACTACTGACAAAATCACTCTGACTCTGACCCTGCCAAGCTGCTGCCTTCTCCTGCCCCAACCTCACCCCCAGCCA
     33970     33980     33990     34000     34010     34020     34030     34040     34050     34060     34070     34080

GGCCTCACTCTTTGCTAGTTCCTTTAGTCTTTTAGTCAATATATTTTTGTCTTCGCATATAAGTATAAATAAACATATTTTTAAATTTCTGGCTGGGCCCAGTGGCTCACGCCTATAATC
     34090     34100     34110     34120     34130     34140     34150     34160     34170     34180     34190     34200
```

FIG. 2 - Continued

FACTOR IX POLYPEPTIDE MUTANT, ITS USES AND A METHOD FOR ITS PRODUCTION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

The present application is the US national stage of International Application PCT/EP2009/061935 filed on Sep. 15, 2009 which, in turn, claims priority to Italian Patent Application BO2008A000564 filed on Sep. 15, 2008 and Italian Patent Application BO2009A000275 filed on May 6, 2009.

FIELD OF THE INVENTION

The present invention relates to a modified FIX (factor IX) polypeptide, a nucleotide sequence, a vector comprising said nucleotide sequence and a method for producing the modified FIX polypeptide.

The present invention also relates to pharmaceutical preparations and uses of modified factor FIX and of the nucleotide sequence.

PRIOR ART

FIX is a vitamin K-dependent glycoprotein belonging to the serine-protease family, and is synthesized in the liver of man and other animals, including mammals, playing a fundamental role in both intrinsic and extrinsic pathways of the coagulation cascade. Human FIX circulates in plasma as a single chain zymogen composed of 415 amino acids. Human FIX has a molecular weight of 56 kD and a plasma concentration of about 5 μg/ml. The zymogen is activated both by activated factor XI (FXIa), and tissue factor complex (TF)—activated factor VII (FVIIa). The structural organization of FIX is similar to that of other vitamin K-dependent coagulation proteins such as factor VII (FVII), factor X (FX) and protein C (PC). The amino-terminal portion of the molecule comprises the "Gla" domain, a region rich in gamma-carboxy-glutamic residues whose carboxylation is dependent on the presence of vitamin K. The main physiological function of FIX, once activated, is to convert factor X (FX) into activated factor X (FXa) in a process that requires the presence of a phospholipid surface, calcium ions and a protein with cofactor effect, namely activated factor VIII (FVIIIa). FXa itself is able to convert prothrombin into thrombin which transforms fibrinogen into soluble fibrin which, on polymerization, forms the clot. The action of FXa is enhanced by the presence of activated factor V (FVa).

The human FIX gene is located on chromosome X in position Xq27.1 and contains 8 exons of lengths varying from 25 base pairs (bp) to 2000 bp. Human FIX mRNA is about 3 kb in length and comprises 205 bases which form the 5' UTR region, 1386 bases which encode the FIX polypeptide and 1392 bases of the 3' UTR region. This mRNA encodes the synthesis of 461 amino acids which form the human FIX precursor. This precursor (SEQ ID NO: 1) comprises the following segments and domains: a hydrophobic signal peptide (amino acids 1-28), a propeptide (amino acids 29-46), a Gla-domain (amino acids 47 to 92), an EGF-like 1 domain (amino acids 93 to 129), an EGF-like 2 domain (amino acids 130 to 171), an activation peptide (amino acids 192 to 226) and a serine-protease domain (amino acids 227 to 461). The mature form of human FIX (SEQ ID NO: 2) loses the hydrophobic signal peptide and the propeptide. Consequently the corresponding amino acid positions of the aforementioned domains become the following: a Gla-domain (amino acids 1 to 46), an EGF-like 1 domain (amino acids 47 to 83), an EGF-like 2 domain (amino acids 84 to 125), an activation peptide (amino acids 146 to 180) and a serine-protease domain (amino acids 181 to 415). SEQ ID NO: 1 (from which SEQ ID NO: 2 is derived) corresponds to the sequence on PubMed ("Protein" category) found by entering accession number AAB59620; this amino acid sequence comprises the signal peptide (46 AA), followed by the amino acid sequence of the mature protein.

A genetic deficiency in FIX can cause a number of coagulation diseases (coagulopathies), for example the haemorrhagic disease known as haemophilia B in affected males (sex linked genetic disease). Haemophilia B can be classified into three classes, each of which is characterized by the presence of different plasma concentrations of FIX. In severe haemophilia B the plasma levels of FIX activity are below 1% of normal; in the moderate form, levels are between 1% and 5%; in the mild form, between 5 and 25% of normal levels. There are also healthy carrier individuals who have medium FIX activity levels, between 25% and 50% of normal, but many carriers can have levels even exceeding 50%. Patients affected by severe haemophilia B present serious haemorrhagic manifestations which can be controlled or avoided by administering FIX concentrates of extractive (from human plasma) or of recombinant origin, currently only available in a single commercial formulation.

Attempts to correct the genetic defect by means of gene therapy have so far been fruitless because of various problems. These include firstly those connected to the low efficiency of expression in man of FIX levels in plasma i.e. around 1%, hence not sufficient to correct the disease; those connected to the immunogenicity of treatment with viral vectors; finally those connected to the side effects of gene therapy itself which include hepatitis, myositis and others.

An increase in plasma FIX to higher than normal levels (normal range of FIX in plasma being 70-120% i.e. 70-120 U/dl, where a unit is the quantity of FIX contained in 1 milliliter of normal plasma, equal to about 5 μg) has been associated with an increased risk in humans of developing thrombotic manifestations in the venous system. In particular, for values above 150 U/dl, a 4.8 fold increase in thrombotic risk has been noted (corrected O. R. 4.8; 95% CI, from 2.3 to 10.1). However, the genetic basis for the increased FIX levels in plasma of these individuals has never been identified.

In vitro mutagenesis studies of mutated recombinant FIX expression have demonstrated the possibility of reproducing the alterations in FIX synthesis and activity encountered in vivo in patients with haemophilia B. Vice-versa, by site-specific mutagenesis in certain positions on the FIX molecule, FIX mutants have been produced with "gain-of-function" (increased activity relative to the normal molecule) by altering their specificity for physiological substrates and/or modifying their other functions. In WO 99/03496 is disclosed the recombinant FIX arginine 338 alanine mutant which resulted in a gain-of-function whose activity levels are 2-3 folds higher than that found in wild type FIX. These gain-of-function mutants (in particular with increased protease activity towards the physiological substrate, i.e. FX, or with an increased capacity for interaction with FVIIIa, a cofactor of FIXa) have not as yet been found to exist in nature, nor have they been tested in man. More explicitly, there is no evidence of: 1) the existence of a human carrier of mutated FIX (natural FIX mutant) with gain-of-function characterized by increased functional activity as compared to normal FIX (WT) with any gain-of-function in functional activity; 2) tests conducted in vivo in man with administrations of modified recombinant FIX; 3) tests conducted in vivo in man with administrations of modified recombinant FIX with gain-of-function for the prophylaxis and treatment of patients affected by haemophilia (genetic or acquired) or other coagulopathies; 4) tests conducted in vivo in man with administrations of modified recombinant FIX which show the absence of side effects.

SUMMARY OF THE INVENTION

The object of the present invention is to provide a modified FIX polypeptide, a nucleotide sequence, a vector comprising said nucleotide sequence, and a method for producing the modified FIX polypeptide.

BRIEF DESCRIPTION OF THE DRAWINGS

FIG. 2. Sequence of the eight exon regions of the factor IX gene including the promoter and some 3'-terminal flanking sequence (SEQ ID NO: 9 and SEQ ID NO: 10). The arrows mark splice junctions and the symbol (●) marks the proposed mRNA start point (residue 296). The symbol (▼) marks the position of poly(A) addition site (residue 33 941) in the mRNA. The dashed lines indicate the approximate length of those introns not shown.

Figure 1:
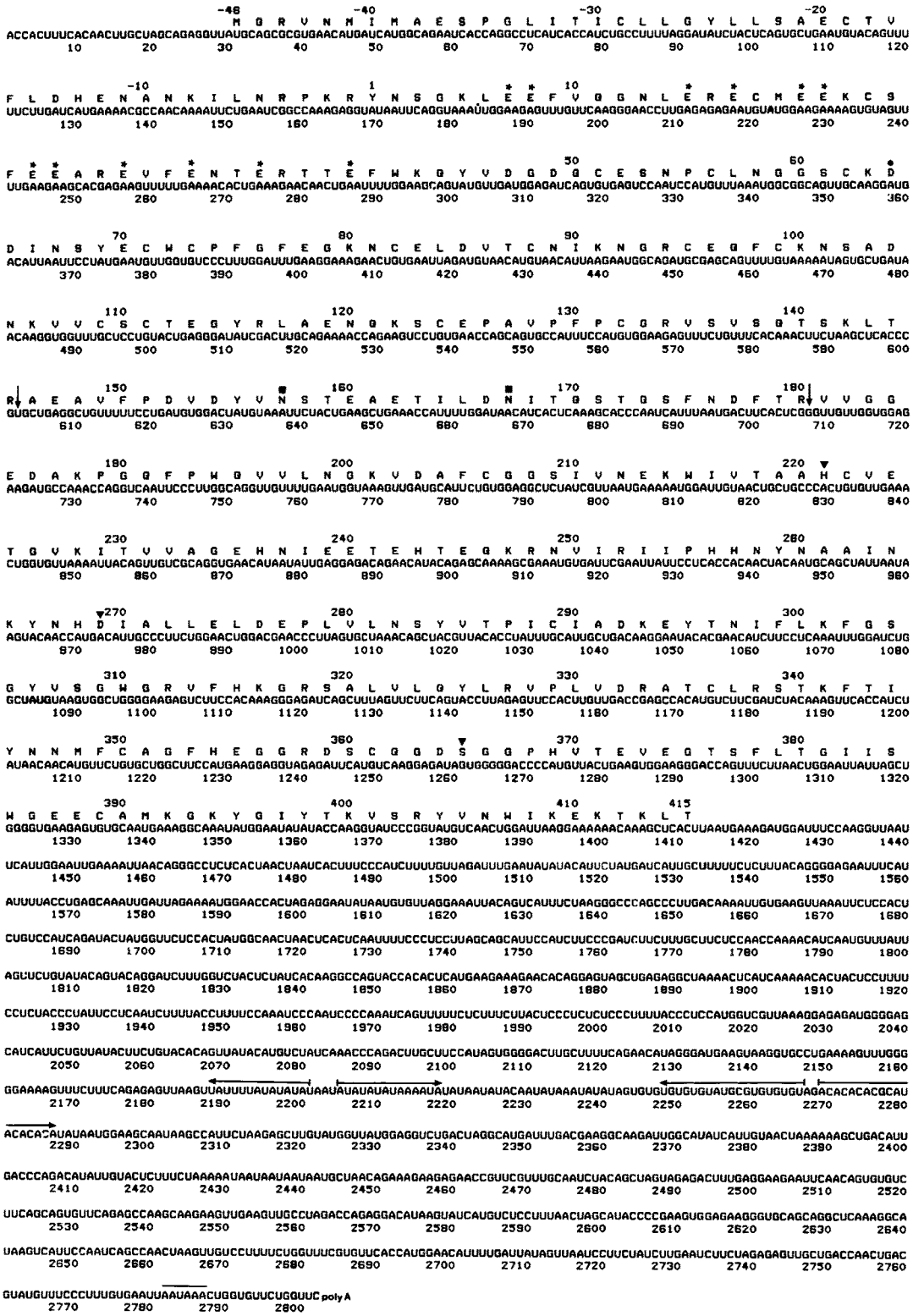
FIG. 1. Sequence of factor IX mRNA (SEQ ID NO: 7) and its encoded protein (SEQ ID NO: 8). The symbols 1-415 define the mature protein and -46 to -1 the precursor region. The latter may be further subdivided into a hydrophobic signal region -46 to -21, and a hydrophilic precursor region -20 to -1 containing three basic amino acids between residues -4 to -1. Vertical arrows indicate the peptide bonds cleaved during activation in clotting. Post-translational modifications are marked (*=12λ-carboxyglutamyl residues, ●=f-hydroxyaspartyl and ■=two Asn-linked carbohydrate residues). The AAUAAA consensus sequence is overlined. His (221), Asp (269) and Ser (365) are marked (▼). Local potential hairpin loops are shown by horizontal arrows.

A further object of the present invention is to provide pharmaceutical preparations and uses for modified factor FIX and the nucleotide sequence.

DETAILED DESCRIPTION OF THE INVENTION

According to the present invention are provided polypeptides, nucleotide sequences, vectors, a method of production, uses of the polypeptides and nucleotide sequences and the pharmaceutical preparations, according to that described in the following independent claims and preferably in any one of the claims that depend directly or indirectly on the independent claims.

The modified FIX polypeptides herein described show a gain-of-function of at least 5 folds higher than that of the wild-type FIX molecule. This increase in the activity level is unexpectedly even higher than that disclosed for the known recombinant FIX arginine 338 alanine mutant.

The contents of the references (articles, textbooks, GenBank sequences etc.) cited in the present text are fully included herein for descriptive completion. In particular, the references (articles, textbooks, GenBank sequences etc.) cited in the present text are incorporated herein for reference.

Unless otherwise explicitly specified, the following terms have the meanings indicated below.

In the present text the term "percentage identity" and "% identity" between two amino acid (peptide) or nucleic acid (nucleotide) sequences means the percentage of identical amino acid or nucleotide residues in corresponding positions in the two optimally aligned sequences.

To determine the "percentage identity" of the two amino acid or nucleic acid sequences, the sequences are aligned together. To achieve an optimal match, gaps can be introduced into the sequence (i.e. deletions or insertions which can also be placed at the sequence ends). Amino acid and nucleotide residues in the corresponding positions are then compared. When a position in the first sequence is occupied by the same amino acid or nucleotide residue that occupies the corresponding position in the second sequence, the molecules are identical in that position. The percentage identity between two sequences is a function of the number of identical positions divided by the sequences [i.e. % identity=(number of identical positions/total number of positions)×100]

According to an advantageous embodiment, the sequences have the same length. Advantageously, the compared sequences do not have gaps (or insertions).

The percentage identity can be obtained by using mathematical algorithms. A non-limiting example of an algorithm used for comparing two sequences is the Karlin and Altschul algorithm [Proc. Natl. Acad. Sci. USA 87 (1990) 2264-2268] modified by Karlin and Altschul [Proc. Natl. Acad. Sci. USA 90 (1993) 5873-5877]. Said algorithm is incorporated in the BLASTn and BLASTp programmes of Altschul [Altschul et al, J. Mol. Bio. 215 (1990) 403-410].

With the purpose of achieving alignments even in the presence of one or more gaps (or insertions) methods may be used which assign a relatively high penalty for each gap (or insertion) and a lower penalty for each additional amino acid or nucleotide residue in the gap (this additional amino acid or nucleotide residue is defined as gap extension). High penalties will obviously lead to the alignments being optimized with the least number of gaps.

An example of a programme able to achieve this type of alignment is the BLAST programme as described in Altschul et al., Nucleic Acids Res. 25 (1997) 3389-3402. For this purpose the BLASTn and BLASTp programmes can be used with the default parameters. When using the BLAST programme the BLOSUM62 matrix is typically employed.

An advantageous and non-limiting example of a programme for achieving an optimal alignment is GCG Wisconsin Bestfit package (University of Wisconsin, USA; Devereux et. al., 1984, Nucleic Acid Research 12:387). The default parameters are again used i.e. for an amino acid sequence they allow a penalty of −12 for a gap and a penalty of −4 for each extension.

In the present text the term "percentage homology" and "% homology" between two amino acid or nucleotide sequences means the percentage of homologous amino acid or nucleotide residues in corresponding positions in the two optimally aligned sequences.

The percentage homology between two sequences is determined in a substantially identical manner to that described above for determining percentage identity except for the fact that homologous positions and not only identical positions are considered in the calculation.

With regard to a nucleotide sequence, two homologous positions present two different nucleotides but which, within their codon, code for the same amino acid. With regard to an amino acid sequence, two homologous positions present two homologous amino acids, that is to say amino acids possessing similar physico-chemical properties, for example amino acids belonging to the same groups such as: aromatic (Phe, Trp, Tyr), acids (Glu, Asp), polar (Gln, Asn), basic (Lys, Arg, His), aliphatic (Ala, Leu, Ile, Val), with a hydroxyl group (Ser, Thr), with a short side chain (Gly, Ala, Ser, Thr, Met). It is expected that substitutions between these homologous amino acids would not change the phenotype of the proteins (conservative amino acid substitutions). Specific examples of conservative is substitutions are known in this technical field and are described in the various literature (e.g. Bowie et al., Science, 247:1306-1310 (1990)).

Further examples of programmes and/or articles relating to the determination of alignments and percentage homologies and/or identities are indicated in, for example, US2008003202, US2007093443, WO06048777.

In the present text the term "corresponding position" means a position in a polypeptide or nucleic acid sequence which, following an alignment, corresponds to (or faces), a precise position in a reference sequence. For example, a position corresponding to a precise position on the FIX polypeptide presenting SEQ ID NO: 2 can be determined by aligning the SEQ ID NO: 2 with a polypeptide of interest; the alignment can be carried out manually or as explained above in relation to percentage identity determination.

In the present text the term "naked chain" means a polypeptide which has not been chemically modified but contains only covalently bound amino acids.

In the present text the term "promoter" means a DNA portion of a gene that controls (activates) the transcription of a nucleotide sequence to which it is operatively linked (but not necessarily flanking it). The promoter includes one or more DNA sequences, which are recognized by RNA polymerase and bind RNA polymerase so that RNA polymerase itself initiates transcription.

In the present text the term "treat" or "treatment" of a pathology means the prophylaxis and/or therapy and/or cure of this pathology. The term prophylaxis means advantageously to at least partially arrest the development of a potential disease and/or to prevent the worsening of symptoms or progression of a disease. Advantageously, the term therapy means a partial or total alleviation of the disease symptoms.

In the present text the term "vector" means an element used to introduce a nucleic acid into a cell for the expression or replication of said nucleic acid. An example of vectors are episomes, which are capable of extra-chromosomal replication. The vectors can also be integrated into host chromosomes. Vectors are often in the form of plasmids, generally circular double-helical DNA.

In the present text "vehicle presenting a nucleic acid" means: a vector which includes nucleic acid; a cell which includes nucleic acid; or a pharmaceutically acceptable excipient combined with the nucleic acid by mixing. Advantageously the vehicle is chosen from a vector or a cell.

According to a first aspect of the present invention, a modified FIX polypeptide is provided comprising an amino acid chosen from the group consisting of: leucine, cysteine, aspartic acid, glutamic acid, histidine, lysine, asparagine, glutamine, tyrosine in a position corresponding to position 338.

According to other embodiments, the amino acid is chosen from the group consisting of: leucine, aspartic acid, glutamine.

According to other embodiments, the amino acid is chosen from the group consisting of: aspartic acid, glutamine.

According to other embodiments, the amino acid is aspartic acid.

According to other embodiments, the amino acid is glutamine.

According to other embodiments, the amino acid is chosen from the group consisting of: aspartic acid, leucine.

According to other embodiments, the amino acid is chosen from the group consisting of: leucine, glutamine.

According to other embodiments, the amino acid is leucine.

The modified FIX polypeptide must be able to carry out its function within the coagulation cascade and can be of synthetic or natural origin, for example human or animal origin.

Examples of FIX polypeptides include (but are not limited to) unmodified wild-type FIX (such as the polypeptide of SEQ ID NO: 2), precursors of said wild-type FIX (such as the polypeptide of SEQ ID NO: 1), natural polymorphic variants (such as: a polypeptide presenting an alanine in a position corresponding to position T148 or to a precursor polypeptide thereof).

In the present text the loci (positions) of the modified or unmodified amino acid sequences are identified by reference to the amino acid numbering in the corresponding positions of an unmodified mature FIX polypeptide, as identified by SEQ ID NO: 2. Corresponding positions can be determined by alignment of unmodified residues (see above). By way of example we report hereinafter the sequences and relative numberings of the mature FIX polypeptide (SEQ ID NO: 2) and of the FIX polypeptide precursor (SEQ ID NO:1).

SEQ ID NO: 1

```
MQRVNMIMAE  SPGLITICLL  GYLLSAECTV  FLDHENANKI
LNRPKRYNSG  KLEEFVQGNL  ERECMEEKCS  FEEAREVFEN
TERTTEFWKQ  YVDGDQCESN  PCLNGGSCKD  DINSYECWCP
FGFEGKNCEL  DVTCNIKNGR  CEQFCKNSAD  NKVVCSCTEG
YRLAENQKSC  EPAVPFPCGR  VSVSQTSKLT  RAEAVFPDVD
YVNSTEAETI  LDNITQSTQS  FNDFTRVVGG  EDAKPGQFPW
QVVLNGKVDA  FCGGSIVNEK  WIVTAAHCVE  TGVKITVVAG
EHNIEETEHT  EQKRNVIRII  PHHNYNAAIN  KYNHDIALLE
LDEPLVLNSY  VTPICIADKE  YTNIFLKFGS  GYVSGWGRVF
HKGRSALVLQ  YLRVPLVDRA  TCLRSTKFTI  YNNMFCAGFH
EGGRDSCQGD  SGGPHVTEVE  GTSFLTGIIS  WGEECAMKGK
YGIYTKVSRY  VNWIKEKTKL  T
```

SEQ ID NO: 2

```
YNSGKLEEFV  QGNLERECME  EKCSFEEARE  VFENTERTTE
FWKQYVDGDQ  CESNPCLNGG  SCKDDINSYE  CWCPFGFEGK
```

-continued

| | | | |
|---|---|---|---|
| NCELDVTCNI | KNGRCEQFCK | NSADNKVVCS | CTEGYRLAEN |
| QKSCEPAVPF | PCGRVSVSQT | SKLTRAETVF | PDVDYVNSTE |
| AETILDNITQ | STQSFNDFTR | VVGGEDAKPG | QFPWQVVLNG |
| KVDAFCGGSI | VNEKWIVTAA | HCVETGVKIT | VVAGEHNIEE |
| TEHTEQKRNV | IRIIPHHNYN | AAINKYNHDI | ALLELDEPLV |
| LNSYVTPICI | ADKEYTNIFL | KFGSGYVSGW | GRVFHKGRSA |
| LVLQYLRVPL | VDRATCL**R**ST | KFTIYNNMFC | AGFHEGGRDS |
| CQGDSGGPHV | TEVEGTSFLT | GIISWGEECA | MKGKYGIYTK |
| VSRYVNWIKE | KTKLT | | |

Likewise, the positions of the modified or unmodified nucleotide sequences are identified, unless otherwise indicated, by reference to the nucleotide numbering in the corresponding positions of the nucleotide sequence identified by accession number K02402 (GenBank). The nucleotide sequence K02402 codes for the FIX polypeptide precursor (SEQ ID NO: 1) and includes some intron regions (in this regard see Anson D S, Choo K H, Rees D J, Giannelli F, Gould K, Huddleston J A, Brownlee G G. The gene structure of human anti-haemophilic factor IX. The EMBO Journal 1984; 3:1053-1060).

Included within the definition of a modified FIX polypeptide are chimeric variants which can be produced by replacing amino acids or entire domains of the FIX with amino acids or sequences of other factors belonging to the coagulation factor family (for example factor VII or factor X).

According to other embodiments, the modified FIX polypeptide presented herein is either a naked chain or exhibits post-transcriptional modifications. Examples of modifications include one or more chemical modifications, which comprise (but are not limited to): glycosylation, acylation, methylation, phosphorylation, sulphation, carboxylation, salification, vitamin C-dependent modifications such as hydrolysis of proline, aspartic acid, lysine, or carboxy-terminal amidation; vitamin K-dependent modifications such as carboxylation of glutamic acid residues; incorporation of selenium to form one or more selenocysteine(s); incorporation of a PEG moiety (polyethylene glycol).

In addition to the possible modifications disclosed herein, the modified FIX polypeptide can contain one or more variants known in the state of the art such as hyperglycosylation, deimmunization and others (see for example: U.S. Pat. No. 6,277,618, U.S. Pat. No. 6,315,995, U.S. Pat. No. 6,531,298, US2004/0102388, US2004/0110675, US2004/0254106, US2005/0100982, US2006/0040856).

Non-limiting examples of modified FIX polypeptide variants can be deduced from one or more of the following references: US2006/040856, Friedler et al (2000) J. Biol Chem. 275:23783-23789, US2004/102388, WO2006/018201, Lim et al. (1990) J. Biol Chem. 265(1):144-150, Cheung et al. (1992) J. Biol. Chem. 267(29): 20529-20531, Gui et al. (2002) Blood 100(1):153-158, Schuettrumpf et al. (2005) Blood 105(6): 2316-2323, US2004/110675, U.S. Pat. No. 6,315,995.

According to some alternative embodiments, the modified FIX polypeptide has at least 50%, 60%, 70%, 80%, 85%, 90%, 94%, 97%, 99%, 100% homology (or, advantageously, identity) with a peptide sequence chosen from the group consisting of: SEQ ID NO: 1 and SEQ ID NO: 2.

Advantageously, the modified FIX polypeptide has at least 60% homology (or, advantageously, identity) with a peptide sequence chosen from the group consisting of: SEQ ID NO: 1 and SEQ ID NO: 2.

Advantageously, the modified FIX polypeptide has at least 80% homology (or, advantageously, identity) with a peptide sequence chosen from the group consisting of: SEQ ID NO: 1 and SEQ ID NO: 2.

Advantageously, the modified FIX polypeptide has at least 90% homology (or, advantageously, identity) with a peptide sequence chosen from the group consisting of: SEQ ID NO: 1 and SEQ ID NO: 2.

Advantageously, the peptide sequence is SEQ ID NO: 2.

According to a second aspect of the present invention, a nucleotide sequence is provided which codes for the FIX polypeptide of the first aspect of the present invention.

According to some alternative embodiments, the nucleotide sequence has at least 50%, 60%, 70%, 80%, 85%, 90%, 94%, 97%, 99%, 100% homology (or, advantageously, identity) with the sequence having accession number K02402 (Gen Bank).

Advantageously, the nucleotide sequence has at least 70% homology (or, advantageously, identity) with the sequence having accession number K02402 (GenBank).

Advantageously, the nucleotide sequence has at least 90% homology (or, advantageously, identity) with the sequence having accession number K02402 (Gen Bank).

Advantageously, the nucleotide sequence has at least 100% homology (or, advantageously, identity) with the sequence having accession number K02402 (Gen Bank).

According to some alternative embodiments, the nucleotide sequence is a RNA sequence and has at least 50%, 60%, 70%, 80%, 85%, 90%, 94%, 97%, 99%, 100% homology (or, advantageously, identity) with the sequence from position 31 to position 1411 (SEQ ID NO: 3) (advantageously from position 169 to position 1411—SEQ ID NO: 5) of the polynucleotide of FIG. 2 in the article by Anson D S, Chao K H, Rees O J, Giannelli F, Gould K, Huddleston J A and Brownlee G G The gene structure of human anti-hemophilic factor IX. The EMBO Journal 1984; 3: 1053-1060, also reported in FIG. 1 of the application. In this case (that is, with reference to SEQ ID NO: 3 and SEQ ID NO: 5, also in the above-mentioned article Anson D S et al.), the position numbers refer to the numbering reported in the aforementioned FIG. 2 of the article Anson D S et al and in the corresponding FIG. 1 of the instant application.

Advantageously, the RNA sequence has at least 80% homology (or advantageously, identity) with the sequence SEQ ID NO: 3 (advantageously, SEQ ID NO: 5). Advantageously, the RNA sequence has at least 90% homology (or, advantageously, identity) with the sequence SEQ ID NO: 3 (advantageously, SEQ ID NO: 5). Advantageously, the RNA sequence has at least 95% homology (or, advantageously, identity) with the sequence SEQ ID NO: 3 (advantageously, SEQ ID NO: 5).

The RNA sequence can be linked, at the head and/or tail, to additional nucleotide chains that are either not translated or translated separately.

According to some alternative embodiments, the nucleotide sequence is a DNA sequence and comprises (in particular, consists of) intron and exon portions, which present an overall sequence (that is to say exon portions without gaps and linked together in order) having at least 50%, 60%, 70%, 80%, 85%, 90%, 94%, 97%, 99%, 100% homology (or, advantageously, identity) with the overall sequence of exon regions in the sequence (SEQ ID NO: 7) of FIG. 4 in the article by Anson D S, Chao K H, Rees O J, Giannelli F, Gould K, Huddleston J A and Brownlee G G. The gene structure of human anti-hemophilic factor IX. The EMBO Journal 1984; 3:1053-1060, corresponding to FIG. 2 of the instant application.

Advantageously, the exon portions are separate from each other and placed in order (arranged relative to each other) as are the respective exon regions in the sequence SEQ ID NO: 7. Advantageously, the overall sequence of the exon portions has at least 80% homology (or, advantageously, identity) with the overall sequence of the exon regions. Advantageously, the overall sequence of the exon portions has at least 90% homology (or, advantageously, identity) with the overall sequence of the exon regions. Advantageously, the overall sequence of the exon portions has at least 95% homology (or, advantageously, identity) with the overall sequence of the exon regions.

According to some embodiments, the nucleotide sequence comprises a thymine in a position corresponding to position 34099 (or in the corresponding position 32318 according to the numbering given in SEQ ID NO: 7; or in the corresponding position 31134 according to the numbering given in the Database of mutations of Hemophilia B (Gianneili et al., Hemophilia B: Database of point mutations and short additions and deletions, Nucleic Acids Research 1990; 18:4053-9); or a uracil in the corresponding position 11180 of SEQ ID NO: 3 or SEQ ID NO: 5).

In other words, the aforementioned nucleotide sequence differs from the sequence having accession number K02402 (GenBank) by at least the fact of bearing a mutation from guanine to thymine in position 34099 (G34099T) or in a corresponding position (for example position 32318 according to the numbering of SEQ ID NO: 7; or from guanine to uracil in the corresponding position 11180 of SEQ ID NO: 3 or SEQ ID NO: 5).

In this case the nucleotide sequence codes for a leucine in a position corresponding to position 338.

According to some embodiments, the nucleotide sequence in the positions corresponding to 34098, 34099 and 34100, presents a triplet chosen from the group consisting of: TTA, UUA, TTG, UUG, CTT, CUU, CTC, CUC, CTA, CUA, CTG, CUG, GAT, GAU, GAC, CAA, CAG. In particular, when the nucleotide sequence is a DNA sequence, the triplet is chosen from the group consisting of TTA, TTG, CTT, CTC, CTA, CTG, GAT, GAC, CAA, CAG.

According to some embodiments, the nucleotide sequence, in the positions corresponding to 34098, 34099 and 34100, presents a triplet chosen from the group consisting of: TTA, UUA, TTG, UUG, CTT, CUU, CTC, CUC, CTA, CUA, CTG, CUG, CAA, CAG. In particular, when the nucleotide sequence is a DNA sequence, the triplet is chosen from the group consisting of TTA, TTG, CTT, CTC, CTA, CTG, CAA, CAG. In these cases, the sequence codes for a leucine or a glutamine in a position corresponding to position 338.

According to some embodiments, the nucleotide sequence, in the positions corresponding to 34098, 34099 and 34100, presents a triplet chosen from the group consisting of: TTA, UUA, TTG, UUG, CTT, CUU, CTC, CUC, CTA, CUA, CTG, CUG. In particular, when the nucleotide sequence is a DNA sequence, the triplet is chosen from the group consisting of TTA, TTG, CTT, CTC, CTA, CTG. Advantageously, the triplet is CTA. In these cases, the sequence codes for a leucine in a position corresponding to position 338.

According to some embodiments, the nucleotide sequence, in the positions corresponding to 34098, 34099 and 34100, presents a triplet chosen from the group consisting of: CAA, CAG. In these cases, the sequence codes for a glutamine in a position corresponding to position 338. Advantageously, the triplet is CAA. To obtain the CAA triplet, an adenine is inserted in place of the guanine in position 34099.

According to some embodiments, the nucleotide sequence, in the positions corresponding to 34098, 34099 and 34100, presents a triplet chosen from the group consisting of: GAT, GAU, GAC, CAA, CAG. In particular, when the nucleotide sequence is a DNA sequence, the triplet is chosen from the group consisting of GAT, GAC, CAA, CAG. In these cases, the sequence codes for an aspartic acid or a glutamine in a position corresponding to position 338.

According to some embodiments, the nucleotide sequence, in the positions corresponding to 34098, 34099 and 34100, presents a triplet chosen from the group consisting of: GAT, GAU, GAC. In particular, when the nucleotide sequence is a DNA sequence, the triplet is chosen from the group consisting of GAT, GAC. In these cases, the sequence codes for an aspartic acid in a position corresponding to position 338. Advantageously, the triplet is GAT. To obtain the GAT triplet, a guanine is inserted in place of the adenine in position 34098, an adenine in place of the guanine in position 34099 and a thymine in place of the adenine in position 34100.

The aforesaid homology (or identity) percentages are calculated without considering the specific mutated positions indicated. In other words, for example, the sequence SEQ ID NO: 2 modified with a leucine in position 338 is considered as having 100% homology (and identity) with the unmodified sequence SEQ ID NO: 2.

According to a third aspect of the present invention, a nucleic acid is provided which comprises a nucleotide sequence according to the second aspect of the present invention.

According to some embodiments, the nucleic acid comprises a promoter in operational linkage with the nucleotide sequence.

According to a fourth aspect of the present invention, a vector is provided comprising a nucleic acid as aforedefined in relation to the third aspect of the present invention. In particular, the vector comprises a nucleotide sequence according to the second aspect of the present invention.

According to some embodiments, the vector is chosen from: a prokaryote vector, a eukaryote vector or a viral vector.

Advantageously, the vector is a viral vector. In particular, the vector is chosen from: an adenovirus, a retrovirus, a herpesvirus, a lentivirus, a poxvirus, a cytomegalovirus.

According to a fifth aspect of the present invention, a method for the production of a modified FIX polypeptide is provided, whereby the modified FIX polypeptide is expressed by means of a nucleic acid according to the third aspect of the present invention.

According to some embodiments the method comprises the steps of: introducing a vector of the fourth aspect of the present invention into a cell; and culturing the cell such that the FIX polypeptide is expressed.

Alternatively, the modified FIX polypeptide can be produced by a host animal or in vitro from the aforementioned nucleotide sequence.

According to a particular aspect of the present invention, the method comprises the steps of: introducing the nucleotide sequence of the second aspect of the present invention into a cell-free system; expressing the modified polypeptide in the cell-free system.

According to a further particular aspect of the present invention, the method allows the modified FIX polypeptide to be expressed in a transgenic animal comprising a nucleic acid in accordance with the third aspect of the present invention (in particular, the nucleotide sequence of the second aspect of the present invention). Useful hosts for expression of the modified FIX polypeptide include: E. coli, yeasts, plants, insect cells, mammalian cells (Pham et al. (2003) Biotechnol. Bioeng. 84:332-42; Bon et al. (1998) Semin Hematol. 35 (2 Suppl 2): 11-17; Wahij et al., J. Biol. Chem. 280 (36) 31603-31607) and transgenic animals.

The hosts can vary as to their levels of protein production and also the types of modifications induced in the modified FIX polypeptide subsequent to transcription. Eukaryote hosts can include yeasts such as Saccharomyces cerevisiae and Pichia pastoris (Skoko et al. (2003) Biotechnol. Appl. Biochem. 38 (Pt 3): 257-65), insect cells (Muneta et al. (2003) J. Vet. Med. Sci. 65(2): 219-23), plants and cells from plants such as tobacco, rice, algae (Mayfield et al. (2003) PNAS 100:438-442) etc. The plants are typically modified by direct transfer of DNA and agrobacterium-mediated transformations. Advantageously usable vectors comprise promoter sequences and transcription termination and control elements.

Yeasts are usually modified by replicating episomal vectors or by a stable chromosomal integration by homologous recombination. Advantageously, promoters are used to regulate gene expression. Examples of promoters include GAL1, GAL7, GALS, CUP1. Proteins produced by yeasts are usually soluble; alternatively, proteins expressed in yeasts can be secreted.

Expression in eukaryotic hosts also includes production in animals, for example in serum, milk and eggs. Transgenic animals for the production of FIX polypeptides are known (for example US2002/0166130 and US2004/0133930) and can be adapted for producing the modified FIX polypeptide as aforedefined.

Prokaryote cells in particular E. coli can be advantageously utilized to produce large quantities of modified FIX polypeptide as aforedefined (Platis et al. (2003) Protein Exp. Purif. 31(2):222-30; Khalizzadeh et al. (2004) J. Ind. Microbiol. Biotechnol. 31(2): 63-69).

The vectors used with E. coli advantageously contain promoters able to induce high levels of protein expression and to express proteins that show some toxicity towards the host cells. Examples of promoters are T7 and SP6 RNA.

Reducing agents such as β-mercaptoethanol can be utilized to solubilise polypeptides which may precipitate in the cytoplasmic environment of E. coli.

According to a sixth aspect of the present invention, a modified FIX polypeptide is also provided in accordance with the first aspect of the present invention, for use as a medicament.

The modified FIX polypeptide can be used for disease treatments either alone or in combination with other active compounds.

The modified FIX polypeptide is useful for treating coagulopathies (congenital or acquired), haematological diseases (congenital or acquired), haemorrhagic disorders (such as haemorrhagic gastritis and/or uterine bleeding), other cardiovascular diseases According to some embodiments, the modified FIX polypeptide is provided for the treatment of at least one coagulopathy.

According to some embodiments, the modified FIX polypeptide is provided for the treatment of haematological diseases.

According to some embodiments, the modified FIX polypeptide is provided for the treatment of haemorrhagic disorders.

According to some embodiments, the modified FIX polypeptide is administered to patients periodically for relatively long time periods or before, during and/or after surgical procedures to reduce and/or prevent haemorrhages.

The use of modified FIX polypeptide for the treatment of coagulopathies is particularly effective.

Advantageously, modified FIX polypeptide is used for the treatment of haemophilia, and in particular haemophilia A and haemophilia B.

According to advantageous embodiments, the modified FIX polypeptide is provided for treating haemophilia B, and advantageously severe and/or moderate haemophilia B.

Advantageously, modified FIX polypeptide is used for the treatment of mammals, in particular human patients.

According to a seventh and an eighth aspect of the present invention, the following are provided: use of the modified FIX polypeptide in accordance with the first aspect of the present invention for preparing a drug (pharmaceutical preparation) advantageously for treating a coagulopathy; and a pharmaceutical preparation comprising the modified FIX polypeptide and, advantageously, at least one pharmaceutically acceptable excipient.

According to some embodiments, the pharmaceutical preparation is for the treatment of a pathology chosen from the group consisting of: coagulopathies (congenital or acquired), haematological diseases (congenital or acquired), haemorrhagic disorders (such as haemorrhagic gastritis and/or uterine bleeding), haemophilia (haemophilia A or haemophilia B). According to specific embodiments, the pharmaceutical preparation is for treating a coagulopathy. According to specific embodiments, the pharmaceutical preparation is for treating haemophilia.

According to a further aspect of the present invention, a method is provided for treating at least one coagulopathy, this method allowing the administration of an effective quantity of a modified FIX polypeptide as aforedefined.

The modified FIX polypeptide can be administered as a pure compound, but is advantageously presented in the form of a pharmaceutical preparation. Non-limiting examples of pharmaceutical preparations if needed for this purpose are explained below.

The modified FIX polypeptide can be formulated for oral, parenteral or rectal administration, or in forms suited to administrations by inhalation or insufflation (either via the mouth or nose). Formulations for oral or parenteral administration are advantageous.

For oral administrations, the pharmaceutical preparations are in the form of, for example, tablets or capsules prepared by known methods with pharmaceutically acceptable excipients such as binders (for example pregelatinized maize starch, polyvinylpyrrolidone, or methyl cellulose); fillers (for example lactose, microcrystalline cellulose or calcium hydrogen phosphate); additives (for example magnesium stearate, talc, silica); disintegrants (for example potato starch); and/or lubricants (for example sodium lauryl sulphate). The tablets can be coated using known methods. Liquid preparations for oral administration have the form, for example, of solutions, syrups or suspensions, or can be in the form of a dry product that can be dissolved in water or another liquid prior to use. Said preparations are prepared by known methods with pharmaceutically acceptable additives such as suspending agents (for example sorbitol, cellulose derivatives, edible hydrogenated fats); emulsifying agents (for example lecithin or acacia); non-aqueous liquids (for example almond oil, oily esters, ethyl alcohol or fractionated vegetable oils); and/or preservatives (for example methyl or propylhydroxybenzoates, sorbic acid or ascorbic acid). The preparations can also contain, in appropriate cases, buffering salts, colouring agents, flavouring agents and/or sweeteners.

Preparations for oral administration are formulated in a known manner, in order to provide a controlled release of the active compound.

The modified FIX polypeptide is formulated, in a known manner, for parenteral administration, by injection or continuous administration. Formulations for injection are, advantageously, in the form of dosage units, for example in ampoules or multi-dose containers containing preservatives. The composition can be in the form of a suspension, in aqueous or oily liquids, and can contain elements of the formulation as dispersing and stabilizing agents. Alternatively, the active compound can be in powder form to be dissolved just before use in a liquid as needed, such as sterile water.

The modified FIX polypeptide can be formulated for rectal administration as suppositories or enemas, for example, containing suppository excipients of known type such as cocoa butter or other glycerides.

The modified FIX polypeptide is also formulated, in a known manner, in extended release compositions. These extended release compositions are, for example, administered by means of an implant (for example subcutaneous or intramuscular) or an intramuscular injection. Therefore, for example, the modified FIX polypeptide is formulated with suitable polymer or hydrophobic materials (such as an emulsion or an oil) or ion exchange resins, or relatively poorly soluble derivatives, such as relatively poorly soluble salts.

For intranasal administration, the modified FIX polypeptide is formulated by administrations via a (known) device, such as in a powder with a suitable vehicle. The dosages of the modified FIX polypeptide will depend on the patient age and condition, and so the precise dosage will have to be decided each time by the 10 physician. The dosage will also depend on the mode of administration and the particular compound selected. Usable doses can be for example comprised between 0.1 μg/kg and 400 μg/kg body weight per day.

According to a further aspect of the present invention, the nucleotide sequence is provided in accordance with the second aspect of the present invention for use as a medicament (advantageously for treating a coagulopathy).

The nucleotide sequence can be used for treating a pathology either alone or in combination with other active compounds.

The nucleotide sequence is useful for treating the pathologies of the sixth aspect of the present invention.

According to particular aspects of the present invention, the following are provided: the use of the aforementioned nucleotide sequence for preparing a drug advantageously for treating a coagulopathy; and a pharmaceutical preparation containing the nucleotide sequence.

Instead of administering the modified FIX polypeptide it is possible to administer the nucleotide sequence which encodes it.

The nucleotide sequence can be inserted into cells or tissues by means of any known method. The nucleotide sequence can be incorporated into a vector for subsequent manipulations.

For example, certain cells could be engineered so as to express the modified FIX polypeptide, by integrating the aforementioned nucleotide sequence into a genomic location operatively linked with the promoter sequences. Said cells can be administered to a patient locally or systemically.

Usable viral vectors include poxvirus, herpesvirus, retrovirus, adenovirus, adeno-associated virus and other viruses suitable for gene therapy.

The vectors can remain as episomal or can be integrated into the chromosomes of the treated individual. Adenovirus serotypes are commercially available from the American Type Culture Collection (ATCC, Rockville).

The viral vectors, in particular adenovirus, are used ex vivo; for example, cells are isolated from a patient and transduced with an adenovirus expressing the modified FIX polypeptide. After a suitable period of culturing, the transduced cells are administered to the patient locally or systemically.

Alternatively, the viruses, in particular adenoviruses, which express the modified FIX polypeptide are isolated and formulated with a pharmaceutically acceptable excipient and administered to the patient. Typically, the adenoviruses are administered at doses of 1 to 1014 particles per kilogram of patient weight, generally from 106 to 1012 particles per kilogram of patient weight.

Additional examples of cell types for the expression and release of the modified FIX polypeptide are fibroblasts and endothelial cells (Palmer et al. (1989) Blood 73:483-445; Yao et al (1991) PNAS 88:8101-8105).

A vehicle which presents the aforementioned nucleotide sequence can be formulated in a similar manner to that described above for the modified FIX polypeptide.

The nucleotide sequence and/or drugs and/or vehicles presenting said nucleotide sequence can be used for treating the pathologies referred to above in relation to the modified FIX peptide.

Advantageously, the aforementioned nucleotide sequence is used for treating mammals, in particular human patients.

According to a further aspect of the present invention, a method is provided for detecting the protein of the first aspect of the present invention and/or the nucleotide sequence of the second aspect of the present invention.

Usable methods are those known in the state of the art, and can be adapted to those polymorphism under study to include for example immunoenzymatic assays, coagulation protein activity tests (including FIX activity), coagulometric and chromogenic tests.

According to some embodiments, the method comprises a step of amplifying by PCR part of a nucleic acid molecule (in which it is required to verify the presence of the nucleotide sequence of the second aspect of the present invention).

Advantageously, the amplification step is preceded by a step of purifying, in particular isolating, the nucleic acid molecule.

Advantageously the amplification step is followed by a sequencing step.

By way of example, the methods of examples 2 and 3 below can be followed to detect the aforesaid nucleotide sequence.

The method for detecting the protein and/or nucleotide sequence can be used to assist in the identification of those individuals who display a high tendency to develop blood diseases such as thrombosis.

Further characteristics of the present invention will ensue from the following description of some examples which are merely illustrative and non-limiting.

Example 1

Routine Laboratory Tests Carried Out on the Proband

Routine laboratory coagulation tests were carried out with regard to thrombophilia screening on an individual (defined as the Proband) exhibiting episodes of deep vein thrombosis but no other health problems.

In particular, the following were carried out: prothrombin time, partial thromboplastin time, factor IX levels, factor VIII and XI levels, antithrombin levels (activity and antigen), protein C levels (coagulometric and chromogenic activity, antigen), protein S levels (total antigen, free antigen and activity), activated protein C resistance, DNA analysis for factor V Leiden, DNA analysis for the prothrombin variant G20210A, antiphospholipid antibodies, plasminogen, fibrinolysis tests. The coagulation tests carried out on the Proband were all found to be within normal limits except for FIX activity (see example 4 below).

Example 2

Isolation of Mutant FIX from Plasma and from the Cell Culture Medium

Isolation of FIX from plasma or from culture medium was achieved by means of the immunoaffinity column technique, using a resin (sepharose 4B) to which the anti-FIX monoclonal antibody AHIX-5041 [Haematologic Technologies, Inc. (Essex Junction, Vt., USA)] was covalently bound (3.5 mg of monoclonal antibody per 3 ml of sepharose resin). Briefly, the column was equilibrated with buffer containing 20 mM Tris, 150 mM NaCl, 1 mM benzamidine (mM=millimolar). Starting from the plasma, vitamin K-dependent factors were precipitated by adding barium chloride. After centrifugation, the sediment was resuspended in a solution containing 0.2 M EDTA. The preparation thus obtained was extensively dialyzed (2 times, for at least 2 hours) in a solution containing 20 mM Tris, 150 mM NaCl. After dialysis, the preparation was permitted to pass through the column at a rate of 0.5 ml/min. After extensive column washing (10 column volumes) with Tris/NaCl buffer, elution was carried out using a solution of acidic glycine (pH 2.45). The eluate pH was immediately neutralized by adding 2 M Tris at pH 7.5. The eluate fractions containing protein (tested by the Bradford protein assay) were pooled and dialyzed against a Tris-NaCl solution, the FIX was then concentrated through a 200 μl microcolumn of fast-flow sepharose Q (ion exchange). The purity of the preparation was evaluated by applying the silver staining technique on the SDS-PAGE gel.

Example 3

Genetic Study of FIX

PCR amplification and direct sequencing of the exons and splice sites of the Proband FIX gene were carried out using standardized techniques and primers as reported in the literature (From: Methods in Molecular Medicine, Vol 31: Hemostasis and Thrombosis Protocols. Edited by D. J. Perry and K. J. Pasi. Humana Press Inc. Totowa, N.J. Chapter 16: Hemophilia B mutational analysis. By Peter Green). Briefly, amplification was carried out by using intron primer pairs flanking each of the eight exons of the FIX gene. The sequencing was undertaken with an ABI PRISM 310 sequencer (Perkin Elmer, Foster City, Calif.) using the ABI PRISM Big Dye Terminator kit for cycle sequencing reactions. The sequence data were analyzed using the Sequencing Analysis 3.0 programme (Perkin Elmer, Calif.). The sequence obtained was compared with the FIX sequence reported on the GenBank database (accession number: K02402).

Analysis of the nucleotide sequence of the Proband FIX gene has documented a single mutation in exon VIII of the FIX gene compared to the normal sequence. The patient was found to be a carrier for a mutation from G to T at position 34099 of the FIX gene (normal sequence of the FIX gene, Gene bank accession number: K02402) (or in the corresponding position 31134 according to the numbering given in the Database of mutations of Hemophilia B (Giannelli et al., Hemophilia B: Database of point mutations and short additions and deletions. Nucleic Acids Research 1990; 18:4053-9) able to change codon 338 from Arginine to Leucine. Therefore the FIX molecule present in the Proband's plasma (mutated FIX) differs from the normal FIX molecule only by the presence of the amino acid substitution in position 338 where there is a Leucine instead of Arginine.

Example 4

In Vitro Mutagenesis, Expression and Purification of Recombinant FIX Containing the Leu 338 Mutation Site-specific mutagenesis was carried out according to standard techniques described by Kunkel (Kunkel T A. Rapid and efficient site-specific mutagenesis without phenotypic selection; Proc Natl Acad Sci, USA 1985, 82:488-492). Sequencing of the cDNA was carried out for assurance that the mutation was correct and that any new mutations had not been introduced. Expression of the recombinant FIX was obtained using "human embryonic kidney cell line 293" and the methods already reported in the literature (Chang J L, Jin J P, Lollar P, et al. Changing residue 338 in human factor IX from arginine to alanine causes an increase in catalytic activity. J. Biol. Chem. 1998; 273:12089-12094). The recombinant FIX was isolated from the supernatant (culture medium) by means of an immunoaffinity column, as aforedescribed. Briefly, the supernatant of the cell culture was collected every 24 hours for 10 days and conserved at −20° C. For the purification the supernatant was thawed out and benzamidine and EDTA were added to a final concentration of 5 milliMoles and 4 milliMoles respectively. After filtration through a Millipore filter, the supernatant was incubated with fast-flow Sepharose Q resin for 12 hours at 4° C. The resin was then re-equilibrated in Tris, NaCl and benzamidine buffer and loaded onto the column. Elution was undertaken with a 0-60 nM calcium gradient. The eluate was then dialyzed in a Tris-NaCl buffer. The preparation was then applied to the immunoaffinity column following the method described in example 2 (in the "in vitro" expression of the recombinant protein). Starting from the culture medium, the procedure was the same as for the plasma, except for the precipitation procedure using BaCl. The culture medium was centrifuged at 4000 g for 20 minutes then subjected to dialysis in Tris-NaCl and loaded onto the immunoaffinity column at a rate of 0.5 ml/min. The remaining steps were the same as those taken for the plasma.

The FIX with the G34099T gene mutation resulting in the 338Leu amino acid substitution, was obtained by in vitro mutagenesis and expression techniques. The level of expression in cell culture was found to be similar to that obtainable with non-mutated recombinant FIX (normal molecule). Specifically, the expression level of the non-mutated recombinant FIX was between 750 and 880 ng/ml while for the recombinant factor IX with the gene mutation G34099T resulting in the 338Leu amino acid substitution, the level was between 590 and 629 ng/ml.

Example 5

Functional Assay of FIX

The functional assay of FIX was carried out on the Proband's plasma with a coagulometric test using Actin (Dade Behring, Marburg, Germany) and FIX deficient plasma (Dade Behring, Marburg, Germany). Briefly for the coagulometric test a variant of the partial thromboplastin time (PTT) was used in a system containing FIX deficient plasma. After adding the calcium chloride the clotting time was measured in seconds. This clotting time was compared to those of a calibration curve obtained by serial dilutions of a pool of normal plasma as reference containing FIX at a quantity of 5 μg/ml (i.e. 100%), and the FIX percentage present in the sample being calculated on 100% of the normal plasma pool (according to common standardized methods).

The normal range for the test had been previously obtained by analyzing, using the same method, 100 healthy individuals of both sexes, aged between 20 and 70 years.

The activity levels of FIX in the Proband were found to be equal to 776% (normal range in 100 healthy individuals, 80-120%).

Example 6

Assay of FIX Antigen

The FIX antigen was determined with the ELISA test using a first anti-FIX monoclonal antibody (Affinity Biologicals, Ontario, Canada) coated (bound) onto the plate for the capture and a second monoclonal antibody labelled with Horseradish peroxidase (HRP) (Affinity Biologicals, Canada) for the detection of FIX. The reference curve was constructed by diluting a pool of normal plasma from 1:100 to 1:3200 in a buffer for the samples, according to standardized procedures. Briefly, the first antibody was bound to the plate after dilution in sodium bicarbonate buffer at basic pH (pH=9.0) at a final concentration of 4 μg/ml. After extensive washing of the plate with Tris-NaCl-Tween20 buffer, the samples, diluted 1:100 and 1:200 in the same buffer, were loaded into the wells and incubated at ambient temperature for 2 hours. After removal of the samples from the wells and extensive washing with the buffer, 100 μl of a solution containing the second antibody conjugated with HRP were added to each of the wells and incubated at ambient temperature for two hours. After further washes, 100 μl of a solution containing tetramethylbenzidine (TMB) were added and the developed color was measured by spectrophotometer with a 450 nanometer filter. The level of FIX antigen was calculated using the reference curve and expressed as a percentage of the pool of normal plasma. The normal test range was previously obtained using the same method by analyzing 100 healthy individuals of both sexes, aged between 20 and 70 years.

FIX antigen levels were found to be equal to 92% (normal range 80-120%). This result (combined with that obtained in example 5) was compatible with the presence of normal quantities of a synthesized circulating FIX, but with its procoagulant function being around 8-9 times greater than the normal FIX molecule.

Example 7

Activity and Antigen Levels of FIX After Reconstitution of a FIX Deficient Plasma with an FIX Extracted from the Proband's Plasma and with Recombinant FIX After isolating FIX from the Proband's plasma, this FIX was used for reconstituting a FIX deficient plasma (Dade-Behring, Milan, Italy) with a final FIX concentration of 5 μg/ml (equal to 100% of normal). The measurements of FIX activity and antigen in the thus reconstituted plasma were 740% and 95% respectively, these being hence comparable with those of the Proband's plasma.

For assaying the activity of the recombinant FIX obtained in accordance with example 4, the same system was used after recomposition of a FIX deficient plasma with a quantity of mutated recombinant FIX (rFIX 338Leu) such as to restore the normal FIX concentration in normal human plasma, i.e. 5 μg/ml (corresponding to 100% of normal) (μg=micrograms). The measurements of recombinant factor IX activity and antigens were 780% and 90% respectively, these being hence comparable with those of the Proband's plasma. This indicates that the recombinant protein thus obtained, containing the amino acid substitution also present in factor IX of the Proband, has a biological activity at least 8-9 times greater than normal factor IX.

Example 8

SDS-PAGE and Immunoblotting of FIX

The SDS-PAGE and immunoblotting (Western blot) of the FIX was carried out on a 5-15% linear gradient gel according to standard procedures. Briefly, the samples containing normal FIX or recombinant FIX were loaded into the polyacrylamide gel wells and subjected to electrophoresis.

The FIX was then subjected to transblotting on a polyvinylidene fluoride (PVDF) membrane using a semidry apparatus (Novablot, GE-Healthcare, Milan, Italy).

The FIX was detected on the PVDF membrane after transblotting using an anti-FIX monoclonal antibody conjugated to HRP (Affinity Biologicals, Ontario, Canada).

SDS-PAGE and immunoblot of a normal FIX polypeptide, a modified FIX polypeptide according to the present invention, a recombinant modified FIX polypeptide according to the present disclosure shows that the FIX isolated from the Proband, the 338Leu recombinant FIX and the normal FIX exhibit the same electrophoretic mobility and the same immunoblot pattern.

Therefore no significant differences (neither quantitative nor qualitative) between normal human FIX, 338 Leu natural mutant human FIX and 338Leu recombinant FIX were found using this technique.

From the aforedescribed, it is clear that the presence of a leucine in a position corresponding to position 338 surprisingly increases the activity of FIX polypeptide by almost eight times.

The present invention proves to be a particular improvement on the state of the art as it provides a modified FIX polypeptide which in vivo in man does not cause any side effects other than an increased coagulation activity.

Example 9

In Vitro Mutagenesis, Expression and Purification of the Recombinant FIX Containing the 338 Asp Mutation (338 Aspartic Acid, 338D)

The site-specific mutagenesis was carried out according to standard techniques described by Kunkel (Kunkel T A. Rapid and efficient site-specific mutagenesis without phenotypic selection; Proc Natl Acad Sci USA 1985, 82: 488-492) by inserting a guanine in place of cytosine in position 34098, and an alanine in place of guanine in position 34099 and a thymine in place of alanine in position 34100 (the mutagenesis was also repeated by inserting a guanine in place of cytosine in position 34098, an adenine in place of guanine in position 34099 and a guanine in place of adenine in position 34100).

Sequencing of the cDNA was carried out for assurance that the mutation was correct and that any new mutations had not been introduced. Expression of the recombinant FIX was obtained using "human embryonic kidney cell line 293" and the methods already reported in the literature (Chang J L, Jin J P, Lollar P, et al. Changing residue 338 in human factor IX from arginine to alanine causes an increase in catalytic activity. J. Biol. Chem. 1998; 273:12089-12094). The recombinant FIX was isolated from the supernatant (culture medium) by means of an immunoaffinity column, as aforedescribed. Briefly, the supernatant of the cell culture was collected every 24 hours for 10 days and conserved at −20° C. For the purification the supernatant was thawed out and benzamidine and EDTA were added to a final concentration of 5 milliMoles and 4 milliMoles respectively. After filtration through a Millipore filter, the supernatant was incubated with fast-flow Sepharose Q resin for 12 hours at 4° C. The resin was then re-equilibrated in Tris, NaCl and benzamidine buffer and loaded onto the column. Elution was undertaken with a 0-60 nM calcium gradient. The eluate was then dialyzed in a Tris-NaCl buffer. The preparation was applied to the immunoaffinity column following the method described in example 2 (in the "in vitro" expression of the recombinant protein). Starting from the culture medium, the procedure was the same as for the plasma, except for the precipitation procedure using BaCl. The culture medium was centrifuged at 4000 g for 20 minutes then subjected to dialysis in Tris-NaCl and loaded onto the immunoaffinity column at a rate of 0.5 ml/min. The remaining steps were the same as those taken for the plasma.

The FIX with the amino acid substitution 338Asp was obtained by in vitro mutagenesis and expression techniques. The level of expression in cell culture was found to be similar to that obtainable with non-mutated recombinant FIX (normal molecule). Specifically, the expression level of the non-mutated recombinant FIX was between 750 and 880 ng/ml while for the recombinant factor IX with the 338Asp amino acid substitution, the level was between 650 and 740 ng/ml.

Example 10

Activity and Antigen Levels of FIX after Reconstitution of a FIX Deficient Plasma with Recombinant FIX with 338Asp Mutation For the assay of the activity of recombinant FIX obtained in accordance with example 9, the same system was used after recomposition of a FIX deficient plasma with a quantity of mutated recombinant FIX (rFIX 338Asp) such as to restore the normal concentration of FIX in normal human plasma, i.e. 5 μg/ml (corresponding to 100% of normal) (μg=micrograms). Measurements of recombinant factor IX activity and antigens were 460% and 98% respectively. This indicates that the recombinant protein thus obtained (FIX 338 Asp), has a biological activity at least 5 times greater than normal factor IX.

Example 11

SDS-PAGE and Immunoblotting of FIX

The SDS-PAGE and immunoblotting (Western blot) of the FIX was carried out on a 5-15% linear gradient gel according to standard procedures. Briefly, the samples containing normal FIX or recombinant FIX were loaded into the polyacrylamide gel wells and subjected to electrophoresis.

The FIX was then subjected to transblotting on a polyvinylidene fluoride (PVDF) membrane using a semidry apparatus (Novablot, GE-Healthcare, Milan, Italy).

The FIX was detected on the PVDF membrane after transblotting using an anti-FIX monoclonal antibody conjugated to HRP (Affinity Biologicals, Ontario, Canada).

The 338Asp recombinant FIX and the normal FIX exhibit the same electrophoretic mobility and the same immunoblot pattern. Therefore no significant differences (neither quantitative nor qualitative) between normal human FIX and 338Asp recombinant FIX were found using this technique.

From the aforedescribed, it is clear that the presence of an Aspartic acid in a position corresponding to position 338 surprisingly increases the activity of FIX polypeptide by almost eight times.

The present invention proves to be a particular improvement on the state of the art as it provides a modified FIX polypeptide which in vivo in man does not cause any side effects other than an increased coagulation activity.

Example 12

In Vitro Mutagenesis, Expression and Purification of Recombinant FIX Containing the 338Gln Mutation (338 Glutamine, 338Q)

Site-specific mutagenesis was carried out according to standard techniques described by Kunkel (Kunkel T A. Rapid and efficient site-specific mutagenesis without phenotypic selection; Proc Natl Acad Sci USA 1985, 82: 488-492) by inserting an adenine in place of guanine in position 34099 (the mutagenesis was also repeated by inserting an adenine in place of guanine in position 34099, and a guanine in place of adenine in position 34100). Sequencing of the cDNA was carried out for assurance that the mutation was correct and that any new mutations had not been introduced. Expression of the recombinant FIX was obtained using "human embryonic kidney cell line 293" and the methods already reported in the literature (Chang J L, Jin J P, Lollar P, et al. Changing residue 338 in human factor IX from arginine to alanine causes an increase in catalytic activity. J. Biol. Chem. 1998; 273:12089-12094). The recombinant FIX was isolated from the supernatant (culture medium) by means of an immunoaffinity column, as aforedescribed. Briefly, the supernatant of the cell culture was collected every 24 hours for 10 days and conserved at −20° C. For the purification the supernatant was thawed out and benzamidine and EDTA were added to a final concentration of 5 milliMoles and 4 milliMoles respectively. After filtration through a Millipore filter, the supernatant was incubated with fast-flow Sepharose Q resin for 12 hours at 4° C. The resin was then re-equilibrated in Tris, NaCl and benzamidine buffer and loaded onto the column. Elution was undertaken with a 0-60 nM calcium gradient. The eluate was then dialyzed in a Tris-NaCl buffer. The preparation was then applied to the immunoaffinity column following the method described in example 2 (in the "in vitro" expression of the recombinant protein). Starting from the culture medium, the procedure was the same as for the plasma, except for the precipitation procedure using BaCl. The culture medium was centrifuged at 4000 g for 20 minutes then subjected to dialysis in Tris-NaCl and loaded onto the immunoaffinity column at a rate of 0.5 ml/min. The remaining steps were the same as those taken for the plasma.

The FIX with the amino acid substitution 33801n was obtained by in vitro mutagenesis and expression techniques. The level of expression in cell culture was found to be similar to that obtainable with non-mutated recombinant FIX (normal molecule). Specifically, the expression level of the non-mutated recombinant FIX was between 750 and 880 ng/ml while for the recombinant factor IX with the 338Gln amino acid substitution, the level was between 600 and 720 ng/ml.

Example 13

Levels of Activity and Antigen of the FIX After Reconstitution of a FIX Deficient Plasma with Recombinant FIX with 338Gln Mutation For the assay of the activity of recombinant FIX obtained in accordance with example 12, the same system was used after recomposition of a FIX deficient plasma with a quantity of mutated recombinant FIX (rFIX 338Gln) such as to restore the normal concentration of FIX in normal human plasma, i.e. 5 μg/ml (corresponding to 100% of normal) (μg=micrograms). Measurements of recombinant factor IX activity and antigens were 1360% and 99% respectively. This indicates that the recombinant protein thus obtained (FIX 338 Gln) has a biological activity at least 13 times greater than normal factor IX.

Example 14

SDS-PAGE and Immunoblotting of FIX

The SDS-PAGE and immunoblotting (Western blot) of the FIX was carried out on a 5-15% linear gradient gel according to standard procedures. Briefly, the samples containing normal FIX or recombinant FIX were loaded into polyacrylamide gel wells and subjected to electrophoresis.

The FIX was then subjected to transblotting on a polyvinylidene fluoride (PVDF) membrane using a semidry apparatus (Novablot, GE-Healthcare, Milan, Italy).

The FIX was detected on the PVDF membrane after transblotting using an anti-FIX monoclonal antibody conjugated to HRP (Affinity Biologicals, Ontario, Canada).

The 338Gln recombinant FIX and the normal FIX exhibited the same electrophoretic mobility and the same immunoblot pattern. Therefore no significant differences (neither quantitative nor qualitative) between normal human FIX and 338Gln recombinant FIX were found using this technique.

From the aforedescribed, it is clear that the presence of a glutamine in a position corresponding to position 338 surprisingly increases the activity of FIX polypeptide by almost thirteen times.

The present invention proves to be a particular improvement on the state of the art as it provides a modified FIX polypeptide which in vivo in humans does not cause any side effects other than an increased coagulation activity.

Therefore evidence is provided that:

1) it has been discovered a naturally occurring FIX mutant (arginine 338 leucine) with a 8-9 fold increased functional activity as compared to FIX wild-type;

2) recombinant modified FIX polypeptides (not known before) with 5 folds (FIX arginine 338 aspartic acid), 8 to 9 folds (FIX arginine 338 leucine), 13 folds (FIX arginine 338 glutamine) increased functional (procoagulant) activity, respectively, as compared to FIX wild-type can be generated.

The use of the mutants of the invention, which show such a specific functional activity of 5 folds or above, and in particular 8 to 9 folds as compared to FIX wild type, for medical use and in particular for the prophylaxis and treatment of Hemophilia B patients; said use of the mutants of the invention has never been considered before and is part of the present invention.

The use of the mutants of the invention, which show such a specific functional activity of 5 folds or above, and in particular 8 to 9 folds as compared to FIX wild type, for gene therapy of Hemophilia B patients has never been considered before and is part of the present invention.

The use of the mutants of the invention, which show a specific functional activity of 5 folds or above, and in particular 8 to 9 folds as compared to FIX wild type, for the prophylaxis and treatment of hemorrhagic coagulopathies other than Hemophilia B or for gene therapy of such diseases has never been considered before and is part of the present invention.

It has to be noted that the use of the mutants of the invention, which show a specific functional activity of 5 folds or above, and in particular of FIX arginine 338 leucine which shows 8 to 9 folds increased functional activity as compared to FIX wild type, is considered optimal for the treatment of patients with hemophilia B because of the presence of an identical naturally occurring mutant in humans (never described before, and is part of the present invention) which does not generate neutralizing antibodies. In addition, the FIX functional activity levels express by FIX arginine 338 leucine, is possibly the best option being higher than that of FIX arginine 338 alanine (previously known and described in WO 99/03496, with a modest increase in activity of 2 to 3 folds that of FIX wild-type) and not too high to cause thrombotic complications in hemophilia B patients or patients with other hemorrhagic coagulopathies.

The invention of FIX arginine 338 leucine, is also the best choice for the use of FIX mutants in gene therapy by using viral vectors, given the actual efficiency and yield of the method for the treatment (partial correction) of Hemophilia B.

According to certain aspects of the present invention there are provided polypeptides, nucleotide sequences, nucleic acids, vectors, methods and uses in accordance with the following points.

1. A modified FIX (factor IX) polypeptide comprising:

an amino acid chosen from the group consisting of: leucine, cysteine, aspartic acid, glutamic acid, histidine, lysine, asparagine, glutamine, tyrosine in a position corresponding to position 338.

2. A polypeptide according to claim 1 wherein the amino acid is chosen from the group consisting of: leucine, aspartic acid, glutamine.

3. A polypeptide according to claim 1 wherein the amino acid is chosen from the group consisting of: aspartic acid, glutamine.

4. A polypeptide according to claim 1 wherein the amino acid is aspartic acid.

5. A polypeptide according to claim 1 wherein the amino acid is glutamine.

6. A polypeptide according to claim 1 wherein the amino acid is leucine.

7. A polypeptide according to one of the previous points, and having a homology of at least 70% with a peptide sequence selected from the group consisting of: SEQ ID NO: 1 and SEQ ID NO: 2.

8. A polypeptide according to one of the previous points, and having a homology of at least 90% with a peptide sequence selected from the group consisting of: SEQ ID NO: 1 and SEQ ID NO: 2.

9. A polypeptide according to one of the previous points, and having a percentage identity of at least 70% with a peptide sequence selected from the group consisting of: SEQ ID NO: 1 and SEQ ID NO: 2.

10. A polypeptide according to one of the previous points, and having a percentage identity of at least 90% with a peptide sequence selected from the group consisting of: SEQ ID NO: 1 and SEQ ID NO: 2.

11. A polypeptide according to one of the previous points wherein the peptide sequence is SEQ ID NO: 2.

12. A nucleotide sequence encoding a FIX polypeptide according to one of the previous points.

13. A nucleotide sequence according to point 12 wherein the nucleotide sequence is a DNA sequence and consists of intron portions and exon portions, the exon portions having an overall sequence with at least 70% homology relative to an overall sequence of exon regions of a SEQ ID NO: 5 sequence.

14. A nucleotide sequence according to point 13 wherein the overall sequence of the exon portions has at least 90% homology with the overall sequence of the exon regions of the SEQ ID NO: 5 sequence.

15. A nucleotide sequence according to one of points 12 to 14 wherein the nucleotide sequence has at least 50% homology with the sequence having the accession number K02402 (GenBank).

16. A nucleotide sequence according to one of points 12 to 15, comprising in positions corresponding to 34098, 34099 and 34100 a triplet chosen from the group consisting of: TTA, UUA, TTG, UUG, CTT, CUU, CTC, CUC, CTA, CUA, CTG, CUG, GAT, GAU, GAC, CAA, CAG.

17. A nucleotide sequence according to point 16, comprising in positions corresponding to 34098, 34099 and 34100 a triplet chosen from the group consisting of: TTA, UUA, TTG, UUG, CTT, CUU, CTC, CUC, CTA, CUA, CTG, CUG, CAA, CAG.

18. A nucleotide sequence according to point 16, comprising in positions corresponding to 34098, 34099 and 34100 a triplet chosen from the group consisting of: TTA, UUA, TTG, UUG, CTT, CUU, CTC, CUC, CTA, CUA, CTG, CUG.

19. A nucleotide sequence according to point 16, comprising in positions corresponding to 34098, 34099 and 34100 a triplet chosen from the group consisting of: CAA, CAG.

20. A nucleotide sequence according to point 16, comprising in positions corresponding to 34098, 34099 and 34100 a triplet chosen from the group consisting of: GAT, GAU, GAC, CAA, CAG.

21. A nucleotide sequence according to point 16, comprising in positions corresponding to 34098, 34099 and 34100 a triplet chosen from the group consisting of: GAT, GAU, GAC.

22. A nucleotide sequence according to one of points 12 to 18, comprising a thymine in a position corresponding to position 34099.

23. A nucleic acid comprising a nucleotide sequence according to one of points 12 to 22.

24. A nucleic acid according to point 23, and comprising a promoter in operational linkage with said nucleotide sequence.

25. A vector comprising a nucleic acid according to point 23 or 24.

26. A method for producing a modified FIX polypeptide, whereby the modified FIX polypeptide is expressed by means of a nucleic acid according to point 23 or 24.

27. A method according to point 26, comprising the steps of: introducing a vector of point 25 into a cell; and culturing the cell such that the FIX polypeptide is expressed.

28. A modified FIX polypeptide according to one of points 1 to 11 for use as a medicament.

29. A modified FIX polypeptide according to one of points 1 to 11 for the treatment of at least one coagulopathy.

30. Use of a modified FIX polypeptide according to one of points 1 to 11 for preparing a drug for the treatment of at least one coagulopathy in a mammal.

31. A nucleotide sequence according to one of points 12 to 22 for use as a medicament.

32. A method for detecting the nucleotide sequence of one of points 12 to 22.

33. A method for detecting the modified FIX polypeptide according to one of points 1 to 11.

34 A method according to point 32 comprising an step of amplification by PCR.

BIBLIOGRAPHY

Ameri A, Kurachi S, Sueishi K, Kuwahara M, Kurachi K. Myocardial fibrosis in mice with overexpression of human blood coagulation factor IX. Blood. 2003 Mar. 1; 101 (5):1871-3. Epub 2002 Oct. 24.

Chang J L, Jin J P, Lollar P, et al. Changing residue 338 in human factor IX from arginine to alanine causes an increase in catalytic activity. J Biol Chem 1998; 273: 12089-12094.

Lowe G D O. Factor IX and thrombosis. British Journal of Haematology, 2001, 115, 507-513.

Kunkel T A. Rapid and efficient site-specific mutagenesis without phenotypic selection. Proc Natl Acad Sci USA 1985, 82:488-492.

Kurachi K, Davie E W. Isolation and characterization of a cDNA coding for human factor IX. Proc Natl Acad Sci USA 1982; 79:6461-6464.

Murphy S L, High K A. Gene therapy for haemophilia. Br J Haematol. 2008 March; 140(5):479-87.

Yoshitake S, Schach B G, Foster D C, et al. Nucleotide Sequence of thr Gene for Human Factor IX (Antihemophilic Factor B). Biochemistry 1985; 24:3736-3750.

Toomey J R, Valocik R E, Koster P F, Gabriel M A, McVey M, Hart T K, Ohlstein E H, Parsons A A, Barone F C. Inhibition of factor IX(a) is protective in a rat model of thromboembolic stroke. Stroke. 2002 February; 33(2): 578-85.

SEQUENCE LISTING

```
Sequence total quantity: 14
SEQ ID NO: 1            moltype = AA  length = 461
FEATURE                 Location/Qualifiers
SIGNAL                  1..56
                        note = SIGNAL PEPTIDE
PEPTIDE                 1..461
                        note = SIGNAL PEPTIDE
SITE                    384
                        note = Arg RESIDUE CORRESPONDING TO 338 OF SEQ ID No. 2
SITE                    384
                        note = RESIDUE MUTATED IN THE CLAIMED INVENTION
source                  1..461
                        mol_type = protein
                        organism = Homo sapiens
SEQUENCE: 1
MQRVNMIMAE SPGLITICLL GYLLSAECTV FLDHENANKI LNRPKRYNSG KLEEFVQGNL  60
ERECMEEKCS FEEAREVFEN TERTTEFWKQ YVDGDQCESN PCLNGGSCKD DINSYECWCP  120
FGFEGKNCEL DVTCNIKNGR CEQFCKNSAD NKVVCSCTEG YRLAENQKSC EPAVPFPCGR  180
VSVSQTSKLT RAEAVFPDVD YVNSTEAETI LDNITQSTQS FNDFTRVVGG EDAKPGQFPW  240
QVVLNGKVDA FCGGSIVNEK WIVTAAHCVE TGVKITVVAG EHNIEETEHT EQKRNVIRII  300
PHHNYNAAIN KYNHDIALLE LDEPLVLNSY VTPICIADKE YTNIFLKFGS GYVSGWGRVF  360
HKGRSALVLQ YLRVPLVDRA TCLRSTKFTI YNNMFCAGFH EGGRDSCQGD SGGPHVTEVE  420
GTSFLTGIIS WGEECAMKGK YGIYTKVSRY VNWIKEKTKL T                      461

SEQ ID NO: 2            moltype = AA  length = 415
FEATURE                 Location/Qualifiers
PEPTIDE                 1..415
SITE                    338
                        note = RESIDUE CORRESPONDING TO 384 OF SEQ ID No. 2
SITE                    338
                        note = RESIDUE MUTATED IN THE CLAIMED INVENTION
source                  1..415
                        mol_type = protein
                        organism = Homo sapiens
SEQUENCE: 2
YNSGKLEEFV QGNLERECME EKCSFEEARE VFENTERTTE FWKQYVDGDQ CESNPCLNGG  60
SCKDDINSYE CWCPFGFEGK NCELDVTCNI KNGRCEQFCK NSADNKVVCS CTEGYRLAEN  120
QKSCEPAVPF PCGRVSVSQT SKLTRAETVF PDVDYVNSTE AETILDNITQ STQSFNDFTR  180
VVGGEDAKPG QFPWQVVLNG KVDAFCGGSI VNEKWIVTAA HCVETGVKIT VVAGEHNIEE  240
TEHTEQKRNV IRIIPHHNYN AAINKYNHDI ALLELDEPLV LNSYVTPICI ADKEYTNIFL  300
KFGSGYVSGW GRVFHKGRSA LVLQYLRVPL VDRATCLRST KFTIYNNMFC AGFHEGGRDS  360
CQGDSGGPHV TEVEGTSFLT GIISWGEECA MKGKYGIYTK VSRYVNWIKE KTKLT       415

SEQ ID NO: 3            moltype = RNA  length = 1381
FEATURE                 Location/Qualifiers
source                  1..1381
                        mol_type = mRNA
                        organism = Homo sapiens
SEQUENCE: 3
tgcagcgcgt gaacatgatc atggcagaat caccaggcct catcaccatc tgccttttag  60
gatatctact cagtgctgaa tgtacagttt ttcttgatca tgaaaacgcc aacaaaattc  120
tgaatcggcc aaagaggtat aattcaggta aattggaaga gtttgttcaa gggaaccttg  180
agagagaatg tatggaagaa aagtgtagtt ttgaagaagc acgagaagtt tttgaaaaca  240
ctgaaagaac aactgaattt tggaagcagt atgttgatgg agatcagtgt gagtccaatc  300
catgtttaaa tggcggcagt tgcaaggatg acattaattc ctatgaatgt tggtgtccct  360
ttggatttga aggaaagaac tgtgaattag atgtaacatg taacattaag aatggcagat  420
gcgagcagtt ttgtaaaaat agtgctgata acaaggtggt ttgctcctgt actgagggat  480
atcgacttgc agaaaaccag aagtcctgtg aaccagcagt gccatttcca tgtggaagag  540
tttctgtttc acaaacttct aagctcaccc gtgctgaggc tgtttttcct gatgtggact  600
atgtaaattc tactgaagct gaaaccattt tggataacat cactcaaagc acccaatcat  660
ttaatgactt cactcgggtt gttggtggag aagatgccaa accaggtcaa ttcccttggc  720
aggttgtttt gaatggtaaa gttgatgcat tctgtggagg ctctatcgtt aatgaaaaat  780
ggattgtaac tgctgcccac tgtgttgaaa ctggtgttaa aattacagtt gtcgcaggtg  840
aacataatat tgaggagaca gaacatacag agcaaaagcg aaatgtgatt cgaattattc  900
ctcaccacaa ctacaatgca gctattaata agtacaacca tgacattgcc cttctggaac  960
tggacgaacc cttagtgcta aacagctacg ttacacctat ttgcattgct gacaaggaat  1020
acacgaacat cttcctcaaa tttggatctg gctatgtaag tggctgggga agagtcttcc  1080
acaaagggag atcagcttta gttcttcagt accttagagt tccacttgtt gaccgagcca  1140
catgtcttcg atctacaaag ttcaccatct ataacaacat gttctgtgct ggcttccatg  1200
aaggaggtag agattcatgt caaggagata gtgggggacc ccatgttact gaagtggaag  1260
ggaccagttt cttaactgga attattagct ggggtgaaga gtgtgcaatg aaaggcaaat  1320
atggaatata taccaaggta tcccggtatg tcaactggat taaggaaaaa acaaagctca  1380
c                                                                  1381

SEQ ID NO: 4            moltype = RNA  length = 1243
FEATURE                 Location/Qualifiers
source                  1..1243
                        mol_type = mRNA
```

```
                        organism = Homo sapiens
SEQUENCE: 4
ataattcagg taaattggaa gagtttgttc aagggaacct tgagagagaa tgtatggaag  60
aaaagtgtag ttttgaagaa gcacgagaag tttttgaaaa cactgaaaga acaactgaat  120
tttggaagca gtatgttgat ggagatcagt gtgagtccaa tccatgttta aatggcggca  180
gttgcaagga tgacattaat tcctatgaat gttggtgtcc ctttggattt gaaggaaaga  240
actgtgaatt agatgtaaca tgtaacatta agaatggcag atgcgagcag ttttgtaaaa  300
atagtgctga taacaaggtg gtttgctcct gtactgaggg atatcgactt gcagaaaacc  360
agaagtcctg tgaaccagca gtgccatttc catgtggaag agtttctgtt tcacaaactt  420
ctaagctcac ccgtgctgag gctgtttttc ctgatgtgga ctatgtaaat tctactgaag  480
ctgaaaccat tttggataac atcactcaaa gcacccaatc atttaatgac ttcactcggg  540
ttgttggtgg agaagatgcc aaaccaggtc aattcccttg gcaggttgtt ttgaatggta  600
aagttgatgc attctgtgga ggctctatcg ttaatgaaaa atggattgta actgctgccc  660
actgtgttga aactggtgtt aaaattacag ttgtcgcagg tgaacataat attgaggaga  720
cagaacatac agagcaaaag cgaaatgtga ttcgaattat tcctcaccac aactacaatg  780
cagctattaa taagtacaac catgacattg cccttctgga actggacgaa cccttagtgc  840
taaacagcta cgttacacct atttgcattg ctgacaagga atacacgaac atcttcctca  900
aatttggatc tggctatgta agtggctggg gaagagtctt ccacaaaggg agatcagctt  960
tagttcttca gtaccttaga gttccacttg ttgaccgagc cacatgtctt cgatctacaa  1020
agttcaccat ctataacaac atgttctgtg ctggcttcca tgaaggaggt agagattcat  1080
gtcaaggaga tagtgggggga ccccatgtta ctgaagtgga agggaccagt ttcttaactg  1140
gaattattag ctggggtgaa gagtgtgcaa tgaaaggcaa atatggaata tataccaagg  1200
tatcccggta tgtcaactgg attaaggaaa aaacaaagct cac                    1243

SEQ ID NO: 5            moltype = DNA  length = 5280
FEATURE                 Location/Qualifiers
misc_feature            600..601
                        note = /note="intron between positions 600-601 not shown,
                         approx length 5400bp" /note="position 601 corresponds to
                         position 6000 in Anson et al paper"
misc_feature            1200..1201
                        note = /note="Intron between position 1200 and 1201, appox
                         length 3960 bp" /note="position 1200 corresponds to
                         position 6600 in Fig. 4 of Anson et al. paper, position
                         1201 corresponds to position 10560
misc_feature            1440..1441
                        note = /note="Intron present between positions 1440 and
                         1441, approx length 7320 bp" /note="position 1440
                         corresponds to 10800 in Fig 4 of Anson et al, position
                         1441 corresponds to 18120 in Fig 4 of Anson et al"
misc_feature            1800..1801
                        note = /note="Intron between positions 1800-1801, approx
                         length 2400 bp" /note="position 1800 corresponds to
                         position 18480 in Fig. 4 of Anson et al., position 1801
                         corresponds to position 20880 of Anson et al
misc_feature            2160..2161
                        note = /note="Intron between 2160 and 2161, approx length
                         9960 bp" /note="position 2160 corresponds to 21240 in Fig
                         4 of Anson et al, position 2161 correspnds to 31080 of Fig
                         4 of Anson et al
misc_feature            3398
                        note = /note="equivalent to position 32318 in Figure 4 of
                         Anson et al paper"
source                  1..5280
                        mol_type = genomic DNA
                        organism = Homo sapiens
CDS                     325..411
                        note = /transl_table=1
CDS                     776..940
                        note = /transl_table=1
CDS                     1129..1152
                        note = /transl_table=1
CDS                     1264..1377
                        note = /transl_table=1
CDS                     1582..1710
                        note = /transl_table=1
CDS                     1881..2084
                        note = /transl_table=1
CDS                     2303..2416
                        note = /transl_table=1
CDS                     3085..3630
                        note = /transl_table=1
SEQUENCE: 5
ctctctgaca aagatacggt gggtcccact gatgaactgt gctgccacag taaatgtagc  60
cactatgcct atctccattc tgaagatgtg tcacttcctg tttcagactc aaatcagcca  120
cagtggcaga agcccacaga atcagaggtg aaatttaata atgaccactg cccattctct  180
tcacttgtcc caagaggcca ttggaaatag tccaaagacc cattgaggga gatggacatt  240
atttcccaga agtaaataca gctcagcttg tactttggta caactaatcg accttaccac  300
tttcacaact tgctagcaga ggttatgcag cgcgtgaaca tgatcatggc agaatcacca  360
```

-continued

```
ggcctcatca ccatctgcct tttaggatat ctactcagtg ctgaatgtac aggtttgttt  420
cctttttaa aatacattga gtatgcttgc cttttagata tagaaatatc tgatgctgtc  480
ttcttcacta aattttgatt acatgatttg acagcaatat tgaagagtct aacagccagc  540
acgcaggttg gtaagtactg gttctttgtt agctaggttt tcttcttctt catttttaaa  600
aatctccatg tgtatacagt actgtgggaa catcacagat tttggctcct atgccctaaa  660
gagaaattgg ctttcagatt atttggatta aaaacaaaga ctttcttaag agatgtaaaa  720
ttttcatgat gttttctttt ttgctaaaac taaagaatta ttcttttaca tttcagtttt  780
tcttgatcat gaaaacgcca acaaaattct gaatcggcca aagaggtata attcaggtaa  840
attggaagag tttgttcaag ggaaccttga gagagaatgt atggaagaaa agtgtagttt  900
tgaagaagca cgagaagttt ttgaaaacac tgaaagaaca gtgagtattt ccacataata  960
cccttcagat gcagagcata gaatagaaaa tctttaaaaa gacacttctc tttaaaattt 1020
taaagcatcc atatatattt atgtatgtta aatgttataa aagataggaa atcaatacca 1080
aaacacttta gatattaccg ttaatttgtc ttcttttatt ctttatagac tgaattttgg 1140
aagcagtatg ttggtaagca attcatttta tcctctagct aatatatgaa acatatgaga 1200
caggggagga ccgggcattc taagcagttt acgtgccaat tcaatttctt aacctatctc 1260
aaagatggag atcagtgtga gtccaatcca tgtttaaatg gcggcagttg caaggatgac 1320
attaattcct atgaatgttg gtgtcccttt ggatttgaag gaaagaactg tgaattaggt 1380
aagtaactat tttttgaata ctcatggttc aaagtttccc tctgaaacaa gttgaaactg 1440
aaaatttctc tccccaacgt atattggggg caacatgaat gcccccaatg tatatttgac 1500
ccatacatga gtcagtagtt ccatgtactt tttagaaatg catgttaaat gatgctgtta 1560
ctgtctattt tgcttctttt agatgtaaca tgtaacatta agaatggcag atgcgagcag 1620
ttttgtaaaa atagtgctga taacaaggtg gtttgctcct gtactgaggg atatcgactt 1680
gcagaaaacc agaagtcctg tgaaccagca ggtcataatc tgaataagat tttttaaaga 1740
aaatctgtat ctgaaacttc agcattttaa caaacctaca taattttaat tcctacttga 1800
cctcaatctc aatttttgta atacatgttc catttgccaa tgagaaatat caggttacta 1860
atttttcttc tatttttcta gtgccatttc catgtggaag agtttctgtt tcacaaactt 1920
ctaagctcac ccgtgctgag gctgtttttc ctgatgtgga ctatgtaaat tctactgaag 1980
ctgaaaccat tttggataac atcactcaaa gcacccaatc atttaatgac ttcactcggg 2040
ttgttggtgg agaagatgcc aaaccaggtc aattcccttg gcaggtactt tatactgatg 2100
gtgtgtcaaa actggagctc agctggcaag acacaggcca ggtgggagac tgaggctatt 2160
aaagctcaca tttccagaaa cattccattt ctgccagcac ctagaagcca atattttgcc 2220
tattcctgta accagcacac atatttattt ttttctagat caaatgtatt atgcagtaag 2280
agtcttaatt ttgttttcac aggttgtttt gaatggtaaa gttgatgcat tctgtggagg 2340
ctctatcgtt aatgaaaaat ggattgtaac tgctgcccac tgtgttgaaa ctggtgttaa 2400
aattacagtt gtcgcaggta aatacacaga aagaataata atctgcagca ccactagctc 2460
tttaatatga ttggtacacc atattttact aaggtctaat aaaattgttg ttgaataaat 2520
tgggctaaag gcagaagggt cataatttca gaacccacgt cgcaccgtcc tccaagcatc 2580
catagttctt ttgatatacc cctattatca ctcatttcag tgaggtacaa ttagttcttg 2640
atgtagccat ttccatacca gaaggccttc ccaaaaatca gtgtcatgtc accgatcctt 2700
ttatctctgg tgcttggcac aacctgtagc aggtcctcag aaaacaaaca tttgaattaa 2760
tggccaaatg agtttgtgct caaaaaaggg gtgaggatac ttgaaatttg gaaaatctag 2820
gataattcat gactagtgga ttcattatca ccaatgaaag gcttataaca gcatgagtga 2880
acagaaccat ctctatgata gtcctgaatg gctttttggt ctgaaaaata tgcattggct 2940
ctcattacat ttaaccaaaa ttatcacaat ataagaatga gatctttaac attgccaatt 3000
aggtcagtgg tcccaagtag tcacttagaa aatctgtgta tgtgaaatac tgtttgtgac 3060
ttaaaatgaa atttattttt aataggtgaa cataatattg aggagacaga acatacagag 3120
caaaagcgaa atgtgattcg aattattcct caccacaact acaatgcagc tattaataag 3180
tacaaccatg acattgccct tctggaactg gacgaaccct tagtgctaaa cagctacgtt 3240
acacctattt gcattgctga caaggaatac acgaacatct tcctcaaatt tggatctggc 3300
tatgtaagtg gctggggaag agtcttccac aaagggagat cagctttagt tcttcagtac 3360
cttagagttc cacttgttga ccgagccaca tgtcttcgat ctacaaagtt caccatctat 3420
aacaacatgt tctgtgctgg cttccatgaa ggaggtagag attcatgtca aggagatagt 3480
gggggacccc atgttactga agtggaaggg accagtttct taactggaat tattagctgg 3540
ggtgaagagt gtgcaatgaa aggcaaatat ggaatatata ccaaggtatc ccggtatgtc 3600
aactggatta aggaaaaaac aaagctcact taatgaaaga tggatttcca aggttaattc 3660
attggaattg aaaattaaca gggcctctca ctaactaatc actttcccat cttttgttag 3720
atttgaatat atacattcta tgatcattgc tttttctctt tacaggggag aatttcatat 3780
tttacctgag caaattgatt agaaaatgga accactagag gaatataatg tgttaggaaa 3840
ttacagtcat ttctaagggc ccagcccttg acaaaattgt gaagttaaat tctccactct 3900
gtccatcaga tactatggtt ctccactatg gcaactaact cactcaattt tccctcctta 3960
gcagcattcc atcttcccga tcttctttgc ttctccaacc aaaacatcaa tgtttattag 4020
ttctgtatac agtacaggat ctttggtcta ctctatcaca aggccagtac cacactcatg 4080
aagaaagaac acaggagtag ctgagaggct aaaactcatc aaaaacacta ctccttttcc 4140
tctaccctat tcctcaatct tttacctttt ccaaatccca atccccaaat cagtttttct 4200
ctttcttact ccctctctcc cttttaccct ccatggtcgt taaaggagag atggggagca 4260
tcattctgtt atacttctgt acacagttat acatgtctat caaacccaga cttgcttcca 4320
tagtggggac ttgcttttca gaacataggg atgaagtaag gtgcctgaaa agtttggggg 4380
aaaagtttct ttcagagagt taagttattt tatatatata atatatatat aaaatatata 4440
atatacaata taaatatata gtgtgtgtgt gtatgcgtgt gtgtagacac acacgcatac 4500
acacatataa tggaagcaat aagccattct aagagcttgt atggttatgg aggtctgact 4560
aggcatgatt tgacgaaggc aagattggca tatcattgta actaaaaaag ctgacattga 4620
cccagacata ttgtactctt tctaaaaata ataataataa tgctaacaga aagaagagaa 4680
ccgttcgttt gcaatctaca gctagtagag actttgagga agaattcaac agtgtgtctt 4740
cagcagtgtt cagagccaag caagaagttg aagttgccta gaccagagga cataagtatc 4800
atgtctcctt taactagcat accccgaagt ggagaagggt gcagcaggct caaaggcata 4860
agtcattcca atcagccaac taagttgtcc ttttctggtt tcgtgttcac catggaacat 4920
tttgattata gttaatcctt ctatcttgaa tcttctagag agttgctgac caactgacgt 4980
atgtttccct ttgtgaatta ataaactggt gttctggttc ataccttggc tttttgtgga 5040
ttccattgat gtgaatcagt caccctgtat ttgatgatgc atgggactac tgacaaaatc 5100
```

```
actctgactc tgaccctgcc aagctgctgc cttctcctgc cccaacctca cccccagcca  5160
ggcctcactc tttgctagtt cctttagtct tttagtcaat atatttttgt cttcgcatat  5220
aagtataaat aaacatattt ttaaatttct ggctgggccc agtggctcac gcctataatc  5280

SEQ ID NO: 6            moltype = AA  length = 8
FEATURE                 Location/Qualifiers
REGION                  1..8
                        note = misc_feature - [CDS]:1129-1152 from SEQ ID NO: 5
source                  1..8
                        mol_type = protein
                        organism = Homo sapiens
SEQUENCE: 6
TEFWKQYV                                                            8

SEQ ID NO: 7            moltype = AA  length = 29
FEATURE                 Location/Qualifiers
REGION                  1..29
                        note = misc_feature - [CDS]:325..411 from SEQ ID NO 5
source                  1..29
                        mol_type = protein
                        organism = Homo sapiens
SEQUENCE: 7
MQRVNMIMAE SPGLITICLL GYLLSAECT                                     29

SEQ ID NO: 8            moltype = AA  length = 38
FEATURE                 Location/Qualifiers
REGION                  1..38
                        note = misc_feature - [CDS]:1264..1377 from SEQ ID NO 5
source                  1..38
                        mol_type = protein
                        organism = Homo sapiens
SEQUENCE: 8
DGDQCESNPC LNGGSCKDDI NSYECWCPFG FEGKNCEL                           38

SEQ ID NO: 9            moltype = AA  length = 43
FEATURE                 Location/Qualifiers
REGION                  1..43
                        note = misc_feature - [CDS]:1582..1710 from SEQ ID NO 5
source                  1..43
                        mol_type = protein
                        organism = Homo sapiens
SEQUENCE: 9
DVTCNIKNGR CEQFCKNSAD NKVVCSCTEG YRLAENQKSC EPA                     43

SEQ ID NO: 10           moltype = AA  length = 55
FEATURE                 Location/Qualifiers
REGION                  1..55
                        note = misc_feature - [CDS]:776..940 from SEQ ID NO 5
source                  1..55
                        mol_type = protein
                        organism = Homo sapiens
SEQUENCE: 10
VFLDHENANK ILNRPKRYNS GKLEEFVQGN LERECMEEKC SFEEAREVFE NTERT        55

SEQ ID NO: 11           moltype = AA  length = 68
FEATURE                 Location/Qualifiers
REGION                  1..68
                        note = misc_feature - [CDS]:1881..2084 from SEQ ID NO 5
source                  1..68
                        mol_type = protein
                        organism = Homo sapiens
SEQUENCE: 11
VPFPCGRVSV SQTSKLTRAE AVFPDVDYVN STEAETILDN ITQSTQSFND FTRVVGGEDA  60
KPGQFPWQ                                                            68

SEQ ID NO: 12           moltype = AA  length = 38
FEATURE                 Location/Qualifiers
REGION                  1..38
                        note = misc_feature - [CDS]:2303..2416 from SEQ ID NO 5
source                  1..38
                        mol_type = protein
                        organism = Homo sapiens
SEQUENCE: 12
VVLNGKVDAF CGGSIVNEKW IVTAAHCVET GVKITVVA                           38

SEQ ID NO: 13           moltype = AA  length = 182
FEATURE                 Location/Qualifiers
REGION                  1..182
                        note = misc_feature - [CDS]:3085..3630 from SEQ ID NO 5
```

-continued

```
source                  1..182
                        mol_type = protein
                        organism = Homo sapiens
SEQUENCE: 13
GEHNIEETEH TEQKRNVIRI IPHHNYNAAI NKYNHDIALL ELDEPLVLNS YVTPICIADK  60
EYTNIFLKFG SGYVSGWGRV FHKGRSALVL QYLRVPLVDR ATCLRSTKFT IYNNMFCAGF  120
HEGGRDSCQG DSGGPHVTEV EGTSFLTGII SWGEECAMKG KYGIYTKVSR YVNWIKEKTK  180
LT                                                                 182

SEQ ID NO: 14           moltype = AA  length = 415
FEATURE                 Location/Qualifiers
source                  1..415
                        mol_type = protein
                        organism = Homo sapiens
SEQUENCE: 14
YNSGKLEEFV QGNLERECME EKCSFEEARE VFENTERTTE FWKQYVDGDQ CESNPCLNGG  60
SCKDDINSYE CWCPFGFEGK NCELDVTCNI KNGRCEQFCK NSADNKVVCS CTEGYRLAEN  120
QKSCEPAVPF PCGRVSVSQT SKLTRAEAVF PDVDYVNSTE AETILDNITQ STQSFNDFTR  180
VVGGEDAKPG QFPWQVVLNG KVDAFCGGSI VNEKWIVTAA HCVETGVKIT VVAGEHNIEE  240
TEHTEQKRNV IRIIPHHNYN AAINKYNHDI ALLELDEPLV LNSYVTPICI ADKEYTNIFL  300
KFGSGYVSGW GRVFHKGRSA LVLQYLRVPL VDRATCLLST KFTIYNNMFC AGFHEGGRDS  360
CQGDSGGPHV TEVEGTSFLT GIISWGEECA MKGKYGIYTK VSRYVNWIKE KTKLT       415
```

The invention claimed is:

[1. A pharmaceutical composition comprising:

a modified recombinant FIX (factor IX) polypeptide comprising at least 70% identity to SEQ ID NO: 2 and a leucine in position 338 of SEQ ID NO: 2; the modified recombinant FIX polypeptide in an amount suitable to provide a daily dosage comprised between 0.1 μg/kg and 400 μg/kg body weight, and at least one pharmaceutically acceptable excipient.]

[2. The pharmaceutical composition according to claim 1, wherein the polypetide comprises at least 90% identity to SEQ ID NO: 2.]

[3. The pharmaceutical composition according to claim 1 formulated for oral, parenteral or rectal administration or suited to administration by inhalation or insufflation.]

[4. A method of treatment, the method comprising administering to an individual in need thereof the pharmaceutical composition according to claim 1.]

[5. The method according to claim 4 wherein the administering is performed to treat at least one coagulopathy in the individual.]

[6. A sequence of nucleotides encoding a modified FIX (Factor IX) polypeptide comprising at least 70% identity to SEQ ID NO: 2 and a leucine at position 338 of SEQ ID NO: 2.]

[7. The sequence of nucleotides according to claim 6, wherein the nucleotide sequence has at least 90% homology with the sequence having accession number K02402 (GenBank).]

8. *A nucleotide sequence encoding a modified FIX (Factor IV) polypeptide comprising 100% identity to SEQ ID NO: 2 except for an alanine at position 148 and a leucine at position 338 of SEQ ID NO: 2 in combination with positions corresponding to positions 34098, 34099 and 34100 of a sequence having accession number K02402 (GenBank) having a triplet selected from the* group consisting of: [TTA, UUA, TTG, UUG, CTT, CUU,] CTC, CUC, [CTA, CUA,] CTG, *and* CUG[, GAT, GAU and GAC].

[9. A nucleic acid comprising the nucleotide sequence according to claim 6.]

[10. The nucleic acid according to claim 9, the nucleic acid comprising a promoter in operational linkage with said nucleotide sequence.]

[11. A vector comprising the nucleic acid according to claim 9.]

[12. A pharmaceutical composition comprising the sequence of nucleotide according to claim 6.]

[13. A method for producing a modified FIX (Factor IX) polypeptide, the method comprising expressing the modified FIX polypeptide by means of a nucleic acid according to claim 9.]

[14. A method to perform gene therapy, the method comprising administering to an individual in need thereof the nucleotide sequence according to claim 6 via a vector configured for gene therapy.]

[15. The method according to claim 14, wherein the administering is performed to treat at least one coagulopathy in the individual.]

*16. The nucleotide sequence of claim 8, wherein the triplet is selected from the group consisting of CTC and CTG.*

*17. The nucleotide sequence of claim 8, wherein the triplet is selected from the group consisting of CUC and CUG.*

*18. The nucleotide sequence of claim 8, wherein the triplet is CTC.*

*19. The nucleotide sequence of claim 8, wherein the triplet is CTG.*

*20. The nucleotide sequence of claim 8, wherein the triplet is CUC.*

*21. The nucleotide sequence of claim 8, wherein the triplet is CUG.*

* * * * *